US012802818B2

(12) United States Patent
Hall et al.

(10) Patent No.: US 12,802,818 B2
(45) Date of Patent: Nov. 17, 2026

(54) ARTIFICIAL INTELLIGENCE (AI) METHOD FOR CLEANING DATA FOR TRAINING AI MODELS

(71) Applicant: PRESAGEN PTY LTD, Adelaide (AU)

(72) Inventors: Jonathan Michael MacGillivray Hall, Adelaide (AU); Donato Perugini, Adelaide (AU); Michelle Perugini, Adelaide (AU); Tuc Van Nguyen, Adelaide (AU); Milad Abou Dakka, Adelaide (AU)

(73) Assignee: PRESAGEN PTY LTD, Adelaide (AU)

( * ) Notice: Subject to any disclaimer, the term of this patent is extended or adjusted under 35 U.S.C. 154(b) by 967 days.

(21) Appl. No.: 17/916,793

(22) PCT Filed: Mar. 30, 2021

(86) PCT No.: PCT/AU2021/000028

§ 371 (c)(1),
(2) Date: Oct. 3, 2022

(87) PCT Pub. No.: WO2021/195688

PCT Pub. Date: Oct. 7, 2021

(65) Prior Publication Data

US 2023/0162049 A1 May 25, 2023

(30) Foreign Application Priority Data

Apr. 3, 2020 (AU) ................................ 2020901043

(51) Int. Cl.
*G06N 5/02* (2023.01)
*G16H 50/20* (2018.01)

(52) U.S. Cl.
CPC ............... *G16H 50/20* (2018.01); *G06N 5/02* (2013.01)

(58) Field of Classification Search
CPC ........ G16H 50/20; G16H 30/40; G16H 50/70; G06N 5/02; G06N 3/0464; G06N 3/098; G06N 3/045; G06N 20/20; G06F 18/28
See application file for complete search history.

(56) References Cited

U.S. PATENT DOCUMENTS 7,225,343 B1 * 5/2007 Honig ..................... G06F 16/13
713/193
9,769,189 B2 * 9/2017 Mohaisen ............ G06F 21/566
(Continued)

OTHER PUBLICATIONS

Xu et al.; Weakly supervised histopathology cancer image segmentation and classification; Feb. 22, 2014; Elsevier; pp. 1-14 (Year: 2014).*
(Continued)

*Primary Examiner* — Phenuel S Salomon
(74) *Attorney, Agent, or Firm* — Seed Intellectual Property Law Group LLP

(57) ABSTRACT

Computational methods and systems for cleaning AI training data are described which clean datasets by dividing a training dataset into a plurality of training subsets. For each training subset we train a plurality of Artificial Intelligence (AI) models on two or more of the remaining plurality of training subsets and using these trained AI models to obtain an estimated label for each sample in the training subset for each AI model. We then remove or relabel samples in the training dataset which are consistently incorrectly predicted by the plurality of AI models and then proceed to generate and deploy a final AI model by training one or more AI models using the cleansed training dataset. A variation of the method may also be used to label a new dataset wherein the new dataset is inserted into the training dataset, and then the training process is itself used to determine the classification of the new dataset using a voting strategy on the estimated labels.

31 Claims, 17 Drawing Sheets

(56) References Cited

U.S. PATENT DOCUMENTS

| | | | | |
|---|---|---|---|---|
| 10,970,589 | B2 * | 4/2021 | Bousmalis | G06F 18/241 |
| 12,315,168 | B2 * | 5/2025 | Liu | G06N 3/08 |
| 2012/0215727 | A1 | 8/2012 | Malik et al. | |
| 2013/0097103 | A1 * | 4/2013 | Chari | G06N 20/10 707/E17.089 |
| 2016/0359886 | A1 * | 12/2016 | Yadav | H04L 63/20 |
| 2019/0132342 | A1 * | 5/2019 | Arlitt | H04L 63/1441 |
| 2019/0147371 | A1 * | 5/2019 | Deo | G06N 20/20 706/12 |
| 2019/0294990 | A1 * | 9/2019 | Lopez De Prado | G06N 20/00 |
| 2019/0305957 | A1 * | 10/2019 | Reddy | G06F 8/60 |
| 2019/0370384 | A1 * | 12/2019 | Dalek | G06F 16/285 |
| 2020/0019884 | A1 * | 1/2020 | McCourt, Jr. | G06N 20/00 |
| 2020/0320335 | A1 | 10/2020 | Shamun et al. | |
| 2021/0383538 | A1 * | 12/2021 | Deasy | A61B 5/055 |

OTHER PUBLICATIONS

Diaz, "Regularization Method: Noise for improving Deep Learning models," Jan. 17, 2020, URL=https://towardsdatascience.com/noise-its-not-always-annoying-1bd5f0f240f, download date Oct. 18, 2022. (19 pages).

Han et al., "Deep Self-Learning From Noisy Labels," *IEEE/CVF International Conference on Computer Vision* (*ICCV*), Seoul, South Korea, Oct. 27, 2019-Nov. 2, 2019, pp. 5138-5147.

Kendall et al., "What Uncertainties Do We Need in Bayesian Deep Learning for Computer Vision," *NIPS'17: Proceedings of the 31st International Conference on Neural Information Processing Systems*, Dec. 4, 2017, pp. 5580-5590.

Natarajan et al., "Learning with Noisy Labels," *NIPS'13: Proceedings of the 26th International Conference on Neural Information Processing Systems*, Dec. 5, 2013, pp. 1196-1204.

Xiao et al., "Learning from Massive Noisy Labeled Data for Image Classification," *IEEE Conference on Computer Vision and Pattern Recognition* (*CVPR*), Boston, MA, United States, Jun. 7-12, 2015, pp. 2691-2699.

Zhang et al., "Online Data Poisoning Attacks," *Proceedings of the 2nd Conference on Learning for Dynamics and Control PMLR 120*, 2020, pp. 1-10.

Verbaeten et al., "Ensemble methods for Noise Elimination in Classification Problems", T. Windeatt and F. Roll (Eds.): MCS 2003, LNCS 2709, pp. 317-325, 2003. (9 pages).

* cited by examiner

200

401

402

403

404

ARTIFICIAL INTELLIGENCE (AI) METHOD FOR CLEANING DATA FOR TRAINING AI MODELS

CROSS-REFERENCE TO RELATED APPLICATION(S)

The present application claims priority from Australian Provisional Patent Application No. 2020901043 titled "ARTIFICIAL INTELLIGENCE (AI) METHOD FOR CLEANING DATA FOR TRAINING AI MODELS" and filed on 3 Apr. 2020, the content of which is hereby incorporated by reference in its entirety.

BACKGROUND

Technical Field

The present disclosure relates to Artificial Intelligence. In a particular form the present disclosure relates to methods for training AI models and classifying data.

Description of the Related Art

Advancements in artificial intelligence (AI) have enabled the development of new products that are restructuring businesses and reshaping the future of many critical industries, including healthcare. Underlying these changes has been the rapid growth of machine learning and deep learning (DL) technologies. In the context of this specification, AI will be used to refer to both machine learning and deep learning methods.

Both machine learning and deep learning are two subsets of Artificial Intelligence (AI). Machine learning is a technique or algorithm that enables machines to self-learn a task (e.g., create predictive models), without human intervention or being explicitly programmed. Supervised machine learning (or supervised learning) is a classification technique that learns patterns in labeled (training) data, where the labels or annotations for each datapoint relates to a set of classes, in order to create (predictive) AI models that can be used to classify new unseen data.

Using identification of embryo viability in IVF as an example, images of an embryo can be labeled "viable" if the embryo led to a pregnancy (viable class) and non-viable if the embryo did not lead to a pregnancy (non-viable class). Supervised learning can be used to train on a large dataset of labeled embryo images in order to learn patterns that are associated with viable and non-viable embryos. These patterns are incorporated in an AI model. The AI model can then be used to classify new unseen images to identify if an embryo (via inferencing on the embryo image) is likely to be viable (and should be transferred to the patient in the IVF treatment) or non-viable (and should not be transferred to the patient).

While deep learning is similar to machine learning in terms of learning objective, it goes beyond statistical machine learning models to better imitate the function of a human neural system. Deep learning models typically consist of artificial "neural networks" that contain numerous intermediate layers between input and output, where each layer is considered a sub-model, each providing a different interpretation of the data. While the machine learning commonly only accepts structured data as its input, deep learning, on the other hand, does not necessarily need structured data as its input. For example, in order to recognize an image of a dog and a cat, a traditional machine learning model needs user-predefined features from those images. Such a machine learning model will learn from certain numeric features as inputs and can then be used to identify features or objects from other unknown images. The raw image is sent through the deep learning network, layer by layer, and each layer would learn to define specific (numeric) features of the input image.

To train a machine learning model (encapsulating also deep learning models), the following steps are normally performed:

a) Exploring the data, in the context of the problem domain and desired AI solution or application. This involves identifying what kind of problem is being solved, e.g., a classification problem or a segmentation problem, and then precisely defining the problem to be solved, e.g., exactly what subset of data is to be used for training the model, and what categories the model will output results into.
b) Cleaning the data, which includes data quality techniques to remove any label noise or bad data (the focus of this patent) and preparing the data so it is ready to be utilized for AI training and validation.
c) Extract features if required by model.
d) Choosing the model configuration, including model architectures and machine learning hyper-parameters.
e) Splitting the data into training dataset, validation dataset and/or test dataset.
f) Training the model by using machine learning and/or deep learning algorithms on the training dataset. Typically, during the training process, many models are produced by adjusting and tuning the machine learning configurations in order to optimize the performance of model (e.g., to increase an accuracy metric) and generalizability (robustness). Each training iteration is referred to as an epoch, with the accuracy estimated and model updated at the end of each epoch.
g) Choosing the best "final" model, or ensemble of models, based on the model's performance on the validation dataset. The model is then applied to the "unseen" test dataset to validate the performance of the final AI model.

In order to effectively train a model, the training data must contain the correct labels or annotations (the correct class label/target in terms of a classification problem). The machine learning or deep learning algorithm finds the patterns in the training data and maps that to the target. The trained model that results from this process is then able to capture these patterns.

As AI-powered technologies have become more prevalent, the demand for quality (e.g., accurate) AI prediction models has become clearer. However the performance of AI models is highly dependent on data quality and the impact of low-quality data for model training can be significant and result in poor quality AI models or AI products, thus leading to poor decision-making outcomes when used in practice (i.e., to classify new data).

Poor quality data may arise in several ways. In some cases data is missing or incomplete for example due to the information being unavailable or due to human error. In other cases data may be biased, for example when the distribution of the training data does not reflect the actual environment in which the machine learning model will be running. For example, in binary classification, this could occur when the number of samples for one class ("class 0") is much greater than that for the other class ("class 1"). A model trained on this dataset would be biased toward class "0" predictions simply because it is trained with more class 0 examples.

Another source of poor data quality is where data is inaccurate—that is, there is label noise such that some class labels are incorrect. This may be a result of data entry errors, uncertainty or subjectivity during the data labeling process, or due to factors beyond the scope of comprehension of the data being collected, such as measurement, clinical or scientific practice. In some cases or problem domains, noisy data may only occur only in a subset of classes. For example some classes can be reliably labeled (correct classes) whereas other classes (noisy classes) comprise higher levels of noise due to uncertainties or subjectively in the labeling process. In exceptional cases, inaccurate or erroneous data may be intentionally added, which is referred to as "adversarial attacks", with the aim of negatively impacting the quality of trained AI.

In healthcare, collecting high quality data can be a challenge. Some examples include:

a) When assessing embryo images for viability in IVF, an embryo can be considered viable if it leads to a pregnancy and non-viable if it does not lead to a pregnancy. The viable class in this case is considered a certain ground-truth outcome because a pregnancy resulted. However, the ground-truth in the non-viable class is uncertain and can be mis-classified or mis-labeled because a perfectly viable embryo may also result in no pregnancy due to other factors unrelated to the intrinsic embryo viability, but rather related to the patient or IVF process.

b) When assessing chest x-rays for pneumonia, radiologists will visually look for white spots in the lungs (called infiltrates) that identify an infection. The assessment can be subjective and prone to error. The image may also be missing required information (or features) for the AI or expert radiologist to make a suitable inference with certainty, which may or may not otherwise be available to medical practitioners with access to a wider range of tests, and not purely assessed from a single image. These images will therefore be missing the key features needed for AI training, and will impact on the quality of the trained AI.

c) When assessing cancer in radiology images, or early glaucoma in retinal images, the presence of cancer or glaucoma may be certain because it was identified and confirmed via relevant medical tests (e.g., a biopsy). However, the absence of cancer or glaucoma may be uncertain because the cancer or glaucoma may be present but has not been identified or detected.

If there is no ground truth or fact, the labeling process would result in noisy data in all classes due to the same reasons as above.

Data cleansing, the process of identifying and addressing poor quality data (such as mis-labeled or "noisy" data) to improve data quality, is thus a critical component for generating predictive models with both high classification accuracy and generalizability. AI companies have made attempts to remove poor quality data from their training datasets or train more robust (noise-tolerant) models. However, this is still an open problem in many areas and many companies are investing significantly into research and development to find techniques to address or mitigate the risk of low-quality data.

Many approaches assume that data labels can be correctly identified/annotated by experts, and that a large dataset may contain identifiably noisy labels. These approaches are considered confident learning approaches. A confident learning approach thus comprises:

a) Estimating the joint probability distribution to characterize class-conditional label noise, b) Filter out noisy examples or change their class labels; and c) Train model with a "cleaned" dataset.

When a small set of data with clean labels is available, this can be exploited to improve the confidence of a neural network using knowledge distillation. Another strategy for a robust (noise-tolerant) model is to introduce synthetic noise into a given dataset to promote noise-tolerant parameters by updating a (student) model to give consistent predictions with a teacher model that is unaffected by synthetic label noise. Another confident learning approach requires the filtering of corrupt ground-truth labels using a mentor model. This is only possible, however, when the definitive ground truth can be obtained. In other words, this type of method requires some measure of supervision to work. Another confident learning method based on Self-Learning (SL) trains an initial classifier on noisy labels in an initial iteration (first epoch). Subsequent iterations (or epochs) use ranked "prototypes" to correct labels and re-train the model on corrected labels. This process continues iteratively until convergence is achieved.

However in many cases it is not possible to accurately or reliably determine ground truth, particularly in real world applications, and thus confident learning methods often break down when applied to real world problems.

For example, there may be multiple data owners each of which provides a set of data samples/images that can be used for model training, validation and testing. However data owners may differ in data collection procedures, data labeling process, data labeling conventions adopted (e.g., when the measurement was taken), and geographical location, and collection mistakes and labeling errors can occur differently with each data owner. Further, for each data owner, labeling errors may occur in all classes, or only in a subset of classes, and the remaining subset of classes contains minimal label noise.

Further it may not always be possible to accurately determine ground truth, or to accurately assess the ground truth in all classes. For example Embryologists are not always correct in assessing the embryo's viability. The confident cases (the sub-class with certain ground truth outcomes) are those associated with images being selected as viable, the embryo transferred to the patient, and after the patient becoming pregnant after 6 weeks. In all other cases, there is low confidence (or high uncertainty) that an embryo associated with an image really leads to successful pregnancy.

There is thus a need to provide methods for cleaning data, or at least providing a useful alternative to existing methods.

BRIEF SUMMARY

According to a first aspect there is provided a computation method for cleaning a dataset for generating an Artificial Intelligence (AI) model, the method comprising:

generating a cleansed training data set comprising:

dividing a training dataset into a plurality (k) of training subsets;

training, for each training subset, a plurality (n) of Artificial Intelligence (AI) models on two or more of the remaining (k−1) training subsets and using the plurality of trained AI models to obtain an estimated label for each sample in the training subset for each trained AI model;

removing or relabeling samples in the training dataset which are consistently incorrectly predicted by the plurality of trained AI models;

generating a final AI model by training one or more AI models using the cleansed training dataset;

deploying the final AI model.

In one form, the plurality of Artificial Intelligence (AI) models comprises a plurality of model architectures.

In one form, training, for each training subset, a plurality of Artificial Intelligence (AI) models on two or more of the remaining (k−1) training subsets comprises:

training, for each training subset, a plurality of Artificial Intelligence (AI) models on all of the remaining (k−1) training subsets.

In one form, removing or relabeling samples in the training dataset comprises:

obtaining a count of the number of times each sample in the training dataset is either correctly predicted, incorrectly predicted or passes a threshold confidence level, by the plurality of trained AI models;

removing or relabeling samples in the training dataset which are consistently wrongly predicted by comparing the predictions with a consistency threshold.

In one form, the consistency threshold is estimated from the distribution of counts.

In one form, the consistency threshold is determined using an optimization method to identify a threshold count that minimizes the cumulative distribution of counts.

In one form, determining a consistency threshold comprises:

generating a histogram of the counts where each bin of the histogram comprises the number of samples in the training dataset with the same count where the number of bins is the number of training subsets multiplied by number of AI models;

generating a cumulative histogram from the histogram;

calculating a weighted difference between each pair of adjacent bins in the cumulative histogram;

setting the consistency threshold as the bin that minimizes the weighted differences.

In one form, method further comprises:

after generating a cleansed training set and prior to generating a final AI model:

iteratively retraining the plurality of trained AI models using the cleansed dataset; and generating an updated cleansed training set until a pre-determined level of performance is achieved or until there are no further samples with a count below the consistency threshold.

In one form, prior to generating the cleansed dataset the training dataset is tested for positive predictive power and the training dataset is only cleaned if the positive predictive power is within a predefined range, wherein estimating the positive predictive power comprises: dividing a training dataset into a plurality of validation subsets;

training, for each validation subset, a plurality of Artificial Intelligence (AI) models on two or more of the remaining (k−1) validation subsets;

obtaining a first count of the number of times each sample in the validation dataset is either correctly predicted, incorrectly predicted, or passes a threshold confidence level, by the plurality of trained AI models;

randomly assigning a label or outcome to each sample;

training, for each validation subset, a plurality of Artificial Intelligence (AI) models on two or more of the remaining (k−1) validation subsets obtaining a second count of the number of times each sample in the validation dataset is either correctly predicted, incorrectly predicted, or passes a threshold confidence level, by the plurality of trained AI models when random assigned labels are used;

estimating the positive predictive power by comparing the first count and the second count.

In one form, the method is repeated for each dataset in a plurality of datasets and the step of generating a final AI model by training one or more AI models using the cleansed training dataset comprises:

generating an aggregated dataset using the plurality of cleaned datasets;

generating a final AI model by training one or more AI models using the aggregated dataset.

In one form, after generating the aggregated dataset the method further comprises cleaning the aggregated dataset according to the method of the first aspect;

In one form, after cleaning the aggregated dataset, the method further comprises:

for each dataset where the positive predictive power is outside the predefined range, adding the untrainable dataset to the aggregated dataset and cleaning the updated aggregated dataset according to the method of the first aspect.

In one form, the method further comprises:

identifying one or more noisy classes and one or more correct classes;

and after training a plurality of Artificial Intelligence (AI) models, the method further comprises selecting a set of models where a model is selected if a metric for each correct class exceeds a first threshold and a metric in each noisy classes is less than a second threshold;

and the step of obtaining a count of the number of times each sample in the training dataset is either correctly predicted or passes a threshold confidence level is performed for each of the selected models;

and the step of removing or relabeling samples in the training dataset with a count below a consistency threshold comprises is performed separately for each noisy class and each correct class, and the consistency threshold is a per-class consistency threshold.

The first metric and the second metric may be a balanced accuracy or a confidence based metric. Multiple metrics could be calculated for each class (e.g. accuracy, balanced accuracy, and log loss), and an ordering defined (for example primary metrics and secondary tie breaker metrics).

In one form, the method further comprises assessing the label noise in a dataset comprising:

splitting the dataset into a training set, validation set and test set;

randomizing the class labels in the training set;

training an AI model on the training set with randomized class labels, and testing the AI model using the validation set and test sets;

estimating a first metric of the validation set and a second metric of the test set;

excluding the dataset if the first metric and the second metric are not within a predefined range.

The first metric and the second metric may be a balanced accuracy or a confidence based metric.

In one form, the method further comprises assessing the transferability of a dataset comprising:

splitting the dataset into a training set, validation set and test set;

training an AI model on the training set, and testing the AI model using the validation set and test sets;

for each epoch in a plurality of epochs, estimating a first metric of the validation set and a second metric of the test set; and estimating the correlation of the first metric and the second metric over the plurality of epochs.

The first metric and the second metric may be a balanced accuracy or a confidence based metric.

According to a second aspect there is provided a computational method for labeling a dataset for generating an Artificial Intelligence (AI) model, the method comprising:

dividing a labeled training dataset into a plurality (k) of training subsets wherein there are C labels;

training, for each training subset, a plurality (n) of Artificial Intelligence (AI) models on two or more of the remaining (k−1) training subsets;

obtaining a plurality of label estimates for each sample in an unlabeled dataset using the plurality of trained AI models;

repeating the dividing, training and obtaining steps C times;

assigning a label for each sample in the unlabeled dataset by using a voting strategy to combine the plurality of estimated labels for the sample.

In one form, the plurality of Artificial Intelligence (AI) models comprises a plurality of model architectures.

In one form, training, for each training subset, a plurality of Artificial Intelligence (AI) models on two or more of the remaining (k−1) training subsets comprises:

training, for each training subset, a plurality of Artificial Intelligence (AI) models on all of the remaining (k−1) training subsets.

In one form, the method further comprises cleaning the labeled training dataset according to the method of the first aspect.

In one form, dividing, training, obtaining and repeating the dividing and training steps C times comprises:

generating C temporary datasets from the unlabeled dataset, wherein each sample in the temporary dataset is assigned a temporary label from the C labels, such that each of the plurality of temporary datasets are distinct datasets, and repeating the dividing, training, and obtaining steps C times comprises performing the dividing, training and obtaining steps for each of the temporary datasets, such that for each temporary datasets the dividing step comprises combining the temporary dataset with the labeled training dataset and then dividing into a plurality (k) of training subsets, and the training and obtaining step comprises training, for each training subset, a plurality (n) of Artificial Intelligence (AI) models on two or more of the remaining (k−1) training subsets and using the plurality of trained AI models to obtain an estimated label for each sample in the training subset for each trained AI model In one form, assigning a temporary label from the C labels is assigned randomly.

In one form, assigning a temporary label from the C labels is estimated by an AI model trained on the training data.

In one form, assigning a temporary label from the C labels is assigned from the set of C labels in random order such that each label occurs once in the set of C temporary datasets.

In one form, the steps of combining the temporary dataset with the labeled training dataset further comprises splitting the temporary dataset into a plurality of subsets, and combining each subset with the labeled training dataset and dividing into a plurality (k) of training subsets and performing the training step.

In one form, the size of each subset is less than the 20% of the size of the training set.

In one form, C is 1 and the voting strategy is a majority inferred strategy.

In one form, C is 1 and the voting strategy is a maximum confidence strategy.

In one form, C is greater than 1, and the voting strategy is a consensus based strategy based on the number of times each label is estimated by plurality of models.

In one form, C is greater than 1 and the voting strategy counts the number of times each label is estimated for a sample, and assigns the label with the highest count that is more than a threshold amount of the second highest count.

In one form, C is greater than 1 and the voting strategy is configured to estimate the label which is reliably estimated by a plurality of models.

In one form, the dataset is a healthcare dataset. In a further form the healthcare dataset comprises a plurality of healthcare images.

According to a third aspect, there is provided a computational system comprising one or more processors, one or more memories, and a communications interface, wherein the one or more memories store instructions for configuring the one or more processors to implement the method of the first or second aspect. According to a fourth aspect there is provided a computational system comprising one or more processors, one or more memories, and a communications interface, wherein the one or more memories are configured to store an AI model trained using the method of any one of claims 1 to 30, and the one or more processors are configured to receive input data via the communications interface, process the input data using the stored AI model to generate a model result, and the communications interface is configured to send the model result to a user interface or data storage device.

BRIEF DESCRIPTION OF THE SEVERAL VIEWS OF THE DRAWINGS

Embodiments of the present disclosure will be discussed with reference to the accompanying drawings wherein.

In the following description, like reference characters designate like or corresponding parts throughout the figures.

DETAILED DESCRIPTION

Embodiments of methods for cleaning a dataset to address the problem of label noise will now be described and will collectively be referred to as "Untrainable Data Cleansing" (UDC). These embodiments may cleanse a dataset by identifying mis-classified or noisy data in a sub-set of classes, or all classes. In the case of classification problems, embodiments of the UDC method enables identification of mislabeled data so that the data can be removed, re-labeled or otherwise handled prior to commencing or during the training of an AI model. Embodiments of the UDC method can also be applied to non-classification problems (i.e., non categorical data or outcomes) such as regression, object detection/segmentation models where the model may give a confidence estimate of the outcome. For example in the case of a model estimating a bounding box in an image, the method will estimate if the box is unacceptable, relatively good, good, very good or with some other confidence level (rather than correct/incorrect). Once mis-classified or noisy data is identified, a decision can then be made to decide how to clean the data (e.g., change the label or delete the data). The cleaned data can then be used to train an AI model which can then be deployed to receive and analyze new data and generate a model result (e.g., a classification, regression, object bounding box, segmentation, etc.). Embodiments of the method may be used on single datasets, or multiple datasets from either the same source or multiple sources.

As will be outlined below, embodiments of the UDC method can be used to identify mis-labeled or hard/impossible to label (incoherent or uninformative) data to a high level of accuracy and confidence, even for "hard" classification problems such as detection of pneumonia from pediatric x-rays. Further variations of the same AI training method can be used for AI inferencing to confidently determine (or 'infer') an unknown label for previously unseen data. This training-based inferencing approach, which we denote Untrainable Data labeling (UDL), can produce more accurate and robust inferencing, particularly for applications which are accuracy-critical but not time or cost critical (e.g., detecting cancer in images). This is particularly the case with healthcare/medical datasets but it will be realized the method has wider application beyond healthcare applications. This training based inferencing is in direct contrast to traditional AI inferencing which is a model-based approach.

Figure 1A:
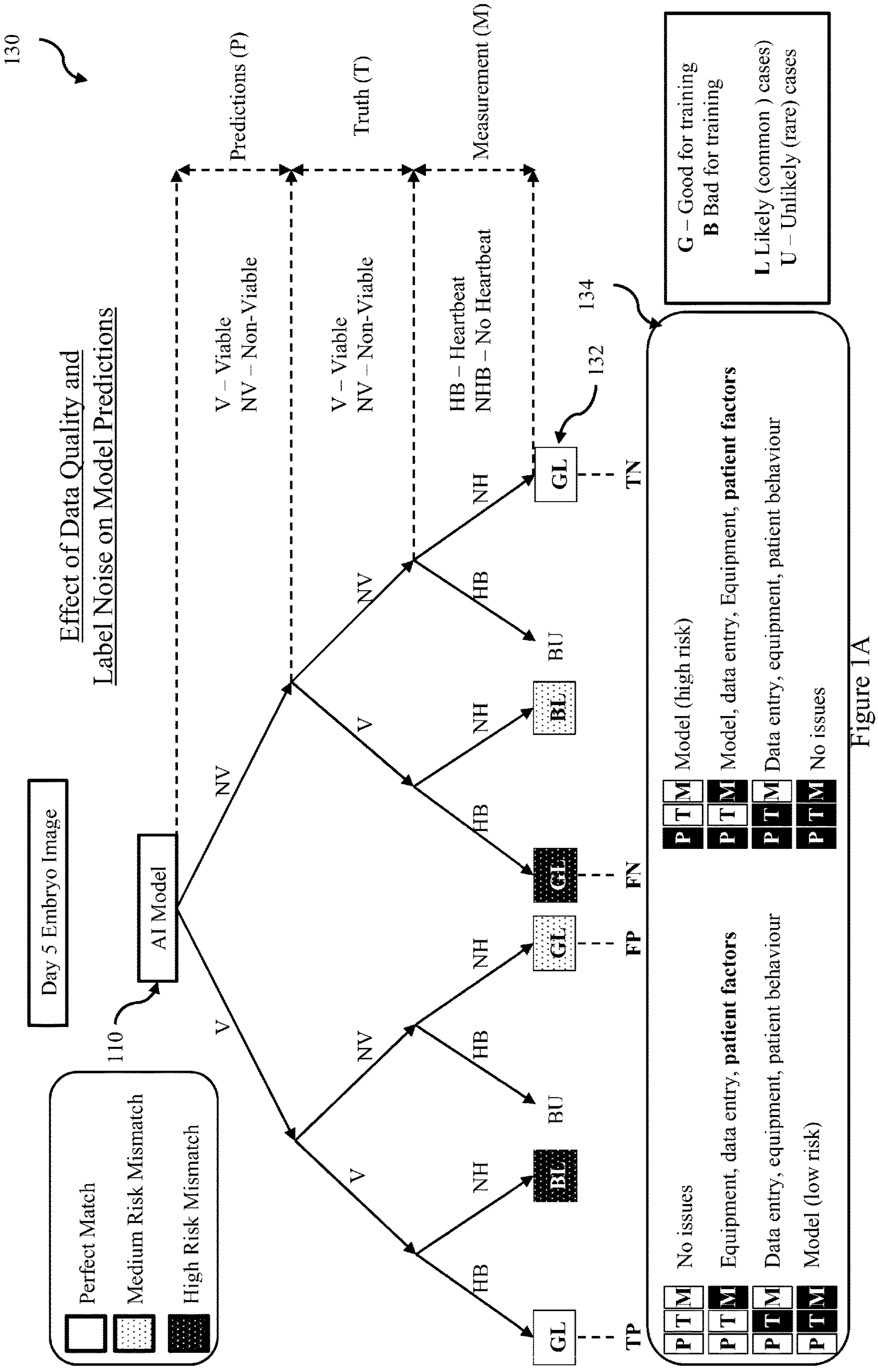
FIG. 1A is a schematic diagram showing the possible combinations of prediction (P), ground-truth (T) and measurement (M) for a binary classification model in which, the binary outcomes are Viable (V) and Non-Viable (NV), along with sources of noise categorized in terms of positive or negative outcomes of prediction, truth and measurement, according to an embodiment.

Before focusing on specific methods for handling noisy data, it is instructive to consider a particular domain-specific example to further explain how where label noise fits into the possible outcomes of model prediction (P), the actual (ground-truth) outcome (T), and the measurement (M) which is recorded as a proxy to the ground-truth (and which can contain noise). FIG. 1A is a schematic diagram 130 summarizing the possible combinations of these three categories in the case of the binary classification problem of Day 5 embryo viability (e.g., to assist in selecting whether to implant an embryo as part of an IVF procedure) by an AI model 110. In this scenario an image of an embryo is assessed by an AI model to estimate the likely viability, and thus whether the embryo should be implanted. Around six weeks after implantation, an attempt is made to measure the heartbeat of the fetus, with detection an indication of a viable embryo and non-detection as an indication of a non-viable embryo. This is a proxy for the ground truth, as it possible for a viable embryo to have been implanted, but subsequently miscarrying for some other reason (e.g., a maternal or external factor). For these three categories, the binary tree has $2^3=8$ combinations, each of which can be associated with a goodness or usefulness for training 132 (i.e., whether the examples represent real cases that do not contain label noise, or whether they are noisy), and the likelihood of them to occur in the dataset. An example (non-exhaustive) summary of the possible sources of noise 134 is also shown in FIG. 1A. The matching or mismatching between the classification model prediction (P) and the measurement (M) is indicated by shading, with medium risk indicated by light shading and heavy black shading indicating the highest risk for this problem domain.

The combinations of prediction, truth and measurement that correspond to True Positives (TP), False Positives (FP), False Negatives (FN) and True Negatives (TN) are also shown in FIG. 1A. In this case, the highest risk for label noise is associated with prediction and truth being positive, and measurement being negative (labeled as bad for training and likely to occur: "BL"). Embodiments of method to distinguish these examples from the False Positives, which generally cannot easily be distinguished in the absence of the absolute ground-truth result will be outlined. The arrows in FIG. 1 indicate that a preponderance of noisy examples as marked, during machine learning, can lead to a larger number of False Negatives, because the model is therefore trained wrongly. Similarly, there are examples with prediction and measurement being negative, and truth being positive (labeled: "BL"), which can lead to a larger number of False Positives during training.

Figure 1B:
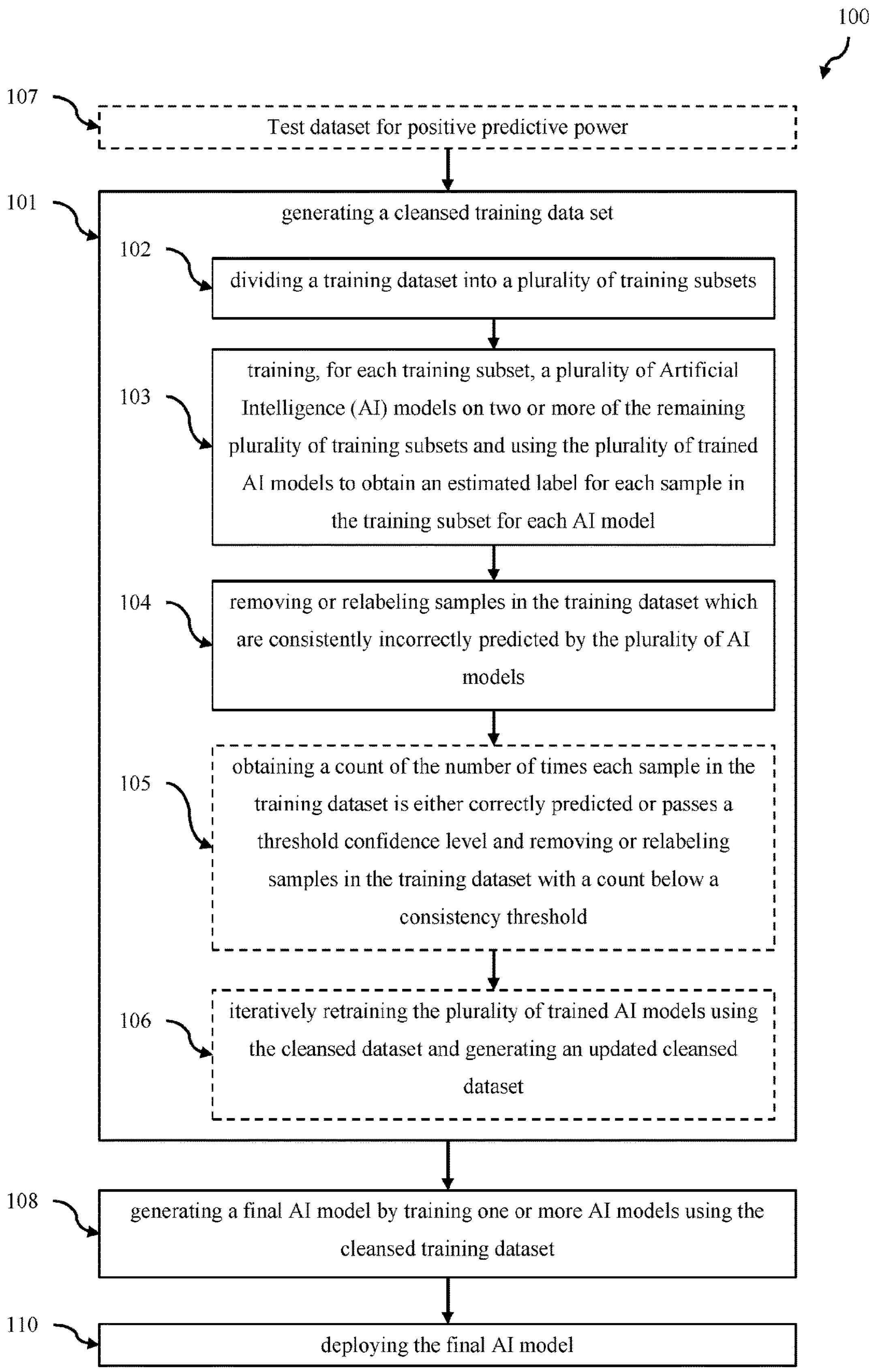
FIG. 1B is a schematic flowchart of a method for cleansing a dataset according to an embodiment.

FIG. 1B is a flowchart of a computation method 100 for cleaning a dataset for generating an Artificial Intelligence (AI) model according to an embodiment. A cleansed training dataset is generated 101 by dividing a training dataset into a plurality of training subsets 102. Then for each training subset we train a plurality of Artificial Intelligence (AI) models on two or more, and typically (but not necessarily) all, of the remaining plurality of training subsets 104 (i.e., a K-fold-cross validation based approach). Each of the AI models may use a different model architecture to create a diversity of AI models (i.e., distinct model architectures), or the same architecture may be used but with different hyper-parameters. The plurality of model architectures may comprise a diversity of general architectures such as Random Forest, Support Vector Machine, Clustering; and Deep Learning/Convolutional neural networks including ResNet, DenseNet, or InceptionNet, as well as the same general architecture but with varying internal configurations, such as a different number of layers and connections between layers, e.g., ResNet-18, ResNet-50, ResNet-101.

We then remove or relabel samples in the training dataset which are consistently incorrectly predicted by the plurality of AI models 104. In some embodiments this may comprise obtaining a count of the number of times each sample in the training dataset is either correctly predicted by the plurality of models, or alternatively incorrectly predicted by the plurality of models. Alternatively we may obtain a count of the number of times each sample in the training dataset passes a threshold confidence level by the plurality of AI models. We then remove or relabel samples in the training dataset which are consistently wrongly predicted by comparing the count with a consistency threshold 105, e.g., below the consistency threshold in the case of counting correct predictions, or over the consistency threshold in the case of counting incorrect predictions. The consistency threshold may be estimated from the distribution of counts, and an optimization method to identify a threshold count that minimizes the cumulative distribution of counts (for example by using a cumulative histogram and calculating a weighted difference between each pair of adjacent bins in the cumulative histogram). The choice of whether to remove low confidence cases or perform label swapping may be determined based on the problem at hand.

In some embodiments this cleaning processes may be repeated by iteratively retraining the plurality of trained AI models using the cleansed dataset and generating an updated cleansed dataset 106. The iterations may be performed until a pre-determined level of performance is achieved. This may be a predetermined number of epochs, after which it is assumed convergence has been achieved (and thus the model after the last epoch is selected). In another embodiment the pre-determined level of performance may be based on a threshold change in one or more metrics such as an accuracy based evaluation metric and/or a confidence based evaluation metric. In the case of multiple metrics, this may be a threshold change in each metric, or a primary metric may be defined, and the secondary metric is used as a tie-breaker, or two (or more) primary metrics are defined, and a third (or further) metric is used as a tiebreaker. In some embodiments prior to cleaning a dataset (101), the positive predictive power of a dataset may be estimated 107, to estimate the amount of label noise presence (i.e., data quality). As will be discussed, this may be used to influence whether or how data cleansing is performed.

Having obtained a cleansed dataset, we then generate a final AI model by training one or more AI models using the cleansed training dataset 108, and we then deploy the final AI model 110 for use on real datasets.

Embodiments of the method may be used on single datasets, or multiple datasets. There may be single or multiple data owners, data-sources and sub-datasets. Each of multiple data owners provides a set of data samples/images that can be used for model training, validation and testing. Data owners may differ in data collection procedures, data labeling process, and geographical location, and collection mistakes and labeling errors can occur differently with each data owner. Further for each data owner, labeling errors may occur in all classes, or only in a subset of classes, and the remaining subset of classes may contain minimal label noise.

Figure 1C:
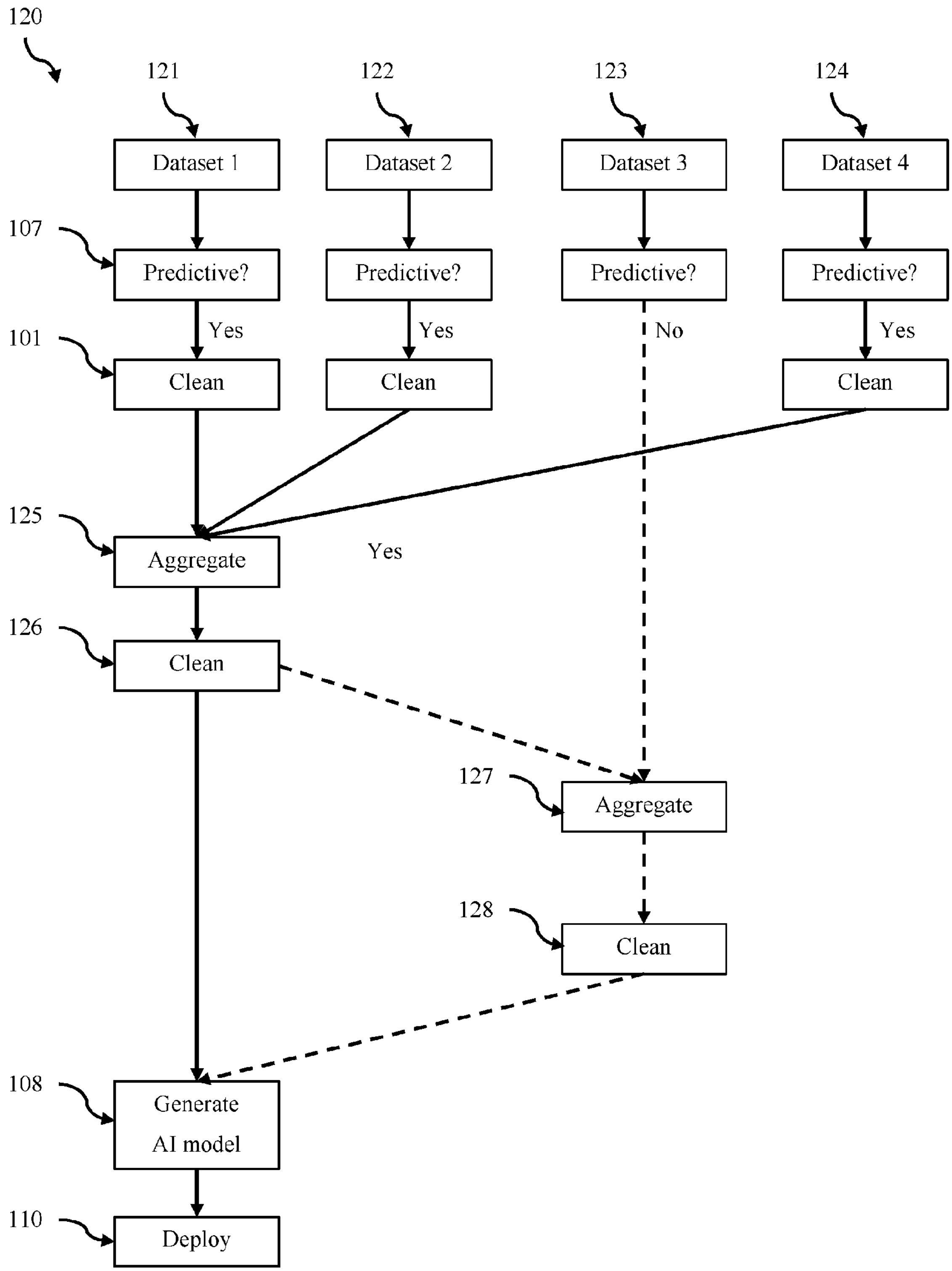
FIG. 1C is a schematic diagram of cleaning multiple datasets according to an embodiment.

FIG. 1C shows an embodiment a method for cleaning multiple datasets 120, based on the method for cleaning a single dataset 100 shown in FIG. 1B. In this embodiment, we have 4 datasets 121, 122, 123, 124. These may be from the same source or multiple data sources. Each dataset is first tested for predictive power 107. Datasets such as Dataset 3 123 which have low predictive power are then set aside. Datasets with sufficient (i.e., positive) predictive power (e.g., exceeding some threshold) are then individually cleaned 101 using the method shown in FIG. 1B. The cleaned datasets are then aggregated 125, and the aggregated dataset are cleaned 126 using the method shown in FIG. 1B. This cleaned aggregated dataset may be used to generate an AI model 108 (and then deployed 110). In another embodiment the dataset's with low predictive power (e.g., Dataset 3 123) are aggregated 127 with the cleaned aggregated dataset 126 and this updated cleaned aggregated dataset is cleaned 128. The final AI model may then be generated 108 and deployed 110.

Figure 1D:
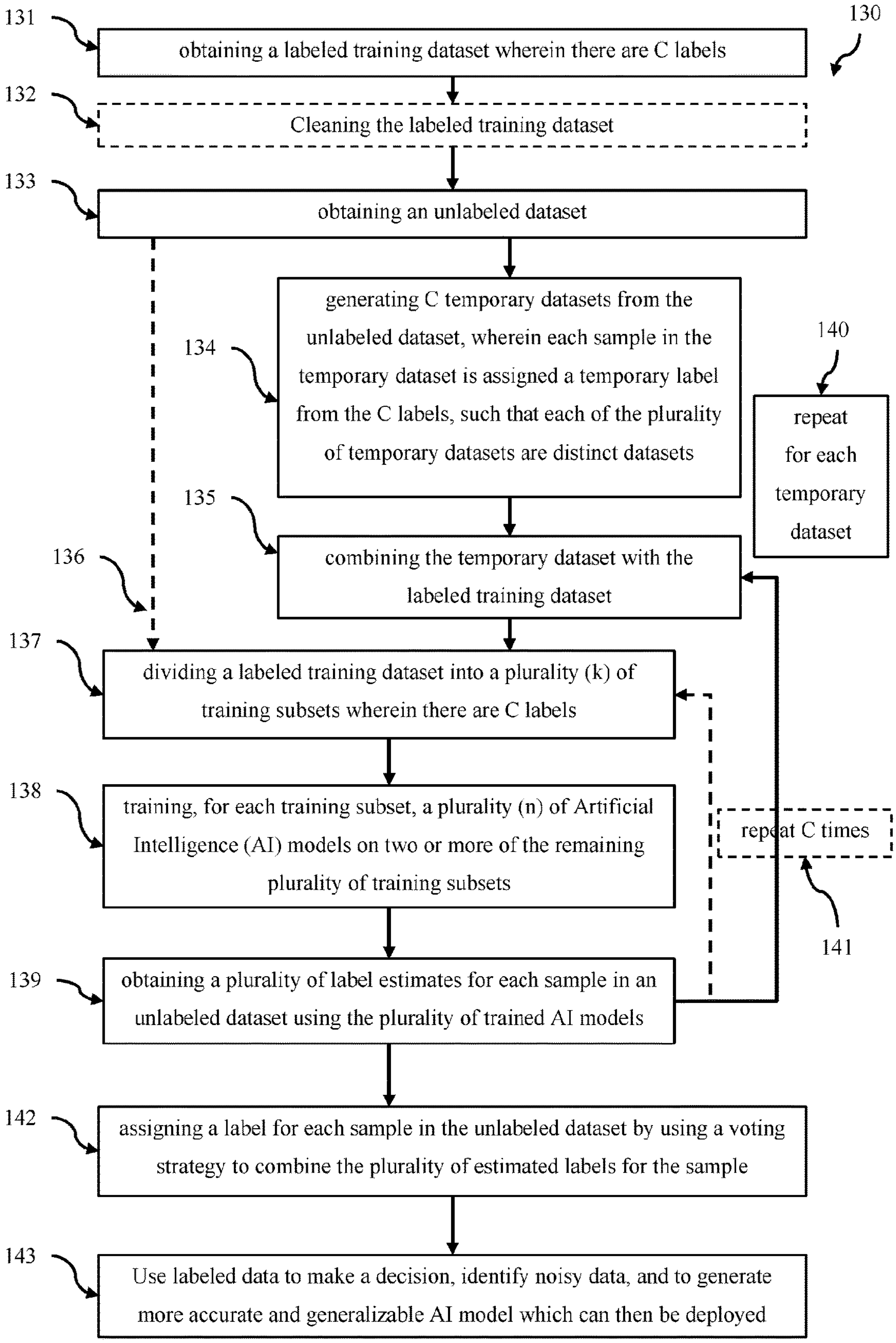
FIG. 1D is a schematic flowchart of a method for labeling a dataset according to an embodiment.

As briefly mentioned above, the UDC method can be varied to infer an unknown label for previously unseen data. FIG. 1D is a flowchart of a method for labeling a dataset 130 according to an embodiment (UDL method). FIG. 1D illustrates two variations of the UDL method a standard UDL method and a fast UDL method which is less computationally intensive than the standard UDL (variations indicated by dashed lines in FIG. 1D). We will first explain standard UDL and then the variation of fast UDL.

UDL is a completely novel approach to AI inferencing. The current approach to AI Inferencing uses a model-based approach, where training data is used to train an AI model, and the AI model is used to inference previously unseen data to classify them (i.e., determine their labels or annotations). The AI model is based on the general patterns or statistically averaged distributions that are learnt from the training data. If the previously unseen data is of a different distribution or an edge case, then misclassification/labeling is more likely, negatively impacting accuracy and generalizability (scalability/robustness). UDL on the other hand is a training-based approach to inferencing. Rather than training an AI model, the AI training process itself is used to determine the classification of previously unseen data.

For both standard and fast UDL we obtain a labeled training dataset wherein there are C labels 131 and an unlabeled dataset 133. In some embodiments the labeled training dataset may be cleaned using an embodiment of the UDC method described and illustrated in FIGS. 1B and 1C.

We then generate C temporary datasets from the unlabeled dataset, wherein each sample in the temporary dataset is assigned a temporary label from the C labels, such that each of the plurality of temporary datasets are distinct datasets 134. That is each unlabeled sample is assigned one label from the list of classes $c \in \{1 \ldots C\}$. These temporary labels can be either a random label or label based on a trained AI model (as per the standard AI model-based inferencing approach). That is we train an AI model, or an ensemble AI model, using the training data, and use the AI model to run a first-pass inference and set a preliminary label for the unseen data. In another embodiment a temporary label is assigned from the set of C labels in random order such that each label occurs once in the set of C temporary datasets. That is we repeat the below UDL method on all/multiple labels in the unseen dataset such that each sample/data-point (e.g., an image) is assigned one label from the list of classes $c \in \{1 \ldots C\}$ in random order to test each class label on each sample/data-point.

For each of the temporary datasets we combine the temporary dataset with the labeled training dataset 135. That is we insert the unseen data into the training data. We then run an embodiment of the UDC method shown in FIG. 1B to determine/infer the actual/final label for the unseen data. this comprises dividing a labeled training dataset into a plurality (k) of training subsets wherein there are C labels 137, and then training, for each training subset, a plurality (n) of Artificial Intelligence (AI) models on two or more, and typically (but not necessarily) all of the remaining plurality of training subsets (i.e., a k-fold Cross validation based approach). Each of the AI models may use a different model architecture. We then obtain a plurality of label (e.g., n×k) estimates for each sample in an unlabeled dataset using the plurality (e.g., n×k) of trained AI models 139. This process is repeated for each temporary dataset 140 (i.e., C times).

We then assign a label for each sample in the unlabeled dataset by using a voting strategy to combine the plurality of estimated labels for the sample 142. For example if we are using a binary classification scheme, then $C_{UDL}=1$, e.g., for classifying an image as a cat or dog we can run UDL once by setting the temporary label in the unseen dataset to either cat or dog, and UDC determines if the label was the correct choice or not to infer the final label. Alternatively, in multi-class classification we run UDL for all possible labels. For example if there are three possible classes (e.g., with labels cats, dogs, bears) then $C_{UDL}=3$, and we run UDL three times where the temporary label is first cat, then dog, and then bear (in shuffled order for each image). The total number of training models is then $R_{UDL}=n \times k \times C_{UDL}$.

In the single class case ($C_{UDL}=1$) then the label can be assigned using a majority inferred label: The chosen label for each unseen datapoint is the label or classification that is inferred by the majority of the $R_{UDL}$ models. In another embodiment a maximum confidence strategy could be used. The chosen label for each unseen datapoint is the label or classification that has the maximum sum of confidence for the label, i.e., the sum of confidence score for label c is $S_c=\Sigma_r \text{conf}_c$, or the sum of the confidence score of label c for all models $r \in \{1 \ldots R_{UDL}\}$. The chosen label is $c_{UDL}=\max(S_c)$, i.e., the label with the maximum confidence score sum.

In the case of multi-class multiple labels ($C_{UDL}>1$), the voting strategy is a consensus based strategy based on the number of times each label is estimated by a plurality of models. That is, we split the inference results for each UDC run by class label c, and for each UDC result compare the number of correct predictions. The class with the highest number of correct predictions is the chosen label for the image. If a label is easily identified as one of the classes from C, then the difference in the number of correct predictions for this class compared to that for other classes is expected to be very high. As this difference approaches the maximum difference (n×k), the confidence of the chosen label is c. The confidence can be estimated based on the difference between the label with the maximum number of successful predictions (say label A) and the second-best label (say label B). Therefore, the confidence of UDL that the label is difference=num(label A)−num(label B). Large differences indicate higher confidence.

The above method inserts the unlabeled data into the training data and the UDC technique is used up to a total of C times to determine which, if any, of the temporary labels is confidently correct (not mis-labeled) or confidently incorrect (was mis-labeled). Ultimately, if the actual label for a new image is knowable (the data in the image is not so noisy or incoherent/uninformative as to contain no discernible features), the UDC can be used to reliably determine (or predict/inference) this label or classification. The labeled data can then be used, for example, to make a decision, identify noisy data, and to generate more accurate and generalizable AI model which can then be deployed 143.

By inserting the unseen data into the training data, the training process itself tries to find specific patterns, correlations and/or statistical distributions in the unseen data in relation to the (clean) training data. The process is thus more targeted and personalized to the unseen data, because the specific unseen data is analyzed and correlated within the context of other data with known outcomes as part of the training process, and the repeated training-based UDC process itself will eventually determine the most likely label for the specific data—potentially boosting both accuracy and generalizability. Even if the unseen data's statistical distribution is different or is an edge case compared to the training data, embedding the data into the training will extract the patterns or correlations with the training data that best classify the unseen data. If an AI model cannot be trained to classify the unseen data with the temporary label, particularly given that the unseen data is contained within the training set itself, then there is high confidence that the label is incorrect and either the alternate label is the correct prediction/inference or the image is so noisy as to contain no discernible features for the AI to learn. Hence, inferencing using UDL (which uses UDC) is likely to produce more accurate and generalizable (robust and scalable) AI inferencing than traditional model-based AI inferencing. However, the time and computational cost will be higher to implement UDL training-based inferencing.

In some embodiments the temporary dataset is split into a plurality of subsets, and each is then combined with the labeled training dataset. This is to ensure size of the new dataset is sufficiently small as not to introduce significant noise into the much larger training dataset, i.e., if the temporary label(s) are incorrect. The optimal dataset size to avoid poisoning the training process is 1 sample, however this can be more costly as each datapoint in the dataset needs to implement a costly and time intensive UDC process to infer their label. In some embodiments the temporary dataset is split such that the size of each subset is less than the 10% or 20% of the size of the training set.

FIG. 1D also illustrates an alternative embodiment referred to as Fast-UDL which is a more computationally efficient approximation to UDL. It uses the standard model-based approach rather than a training-based approach to inferencing, however like UDC and UDL, it considers inferences of many AI models to determine the labels for an unseen dataset. In this embodiment we thus skip the creation of temporary datasets 134 and combining with the training dataset 135, and instead proceed directly (dashed line 136) to create n×k×$C_{UDL}$ diverse AI models using the clean training dataset by performing the dividing 137 and training 138 steps on just the training data (to create n×k models), and then we obtaining a plurality of label estimates 138 by using each of the n×k models to infer the labels in the unseen dataset. The dividing 137, training 138 and obtaining 139 is repeated C times 141. Each datapoint in the unseen dataset will thus now have n×k inferences/labels, and a confidence score and we use this data to assign a label for each sample in the unlabeled dataset 142 in the same way for standard UDL.

Figure 1E:
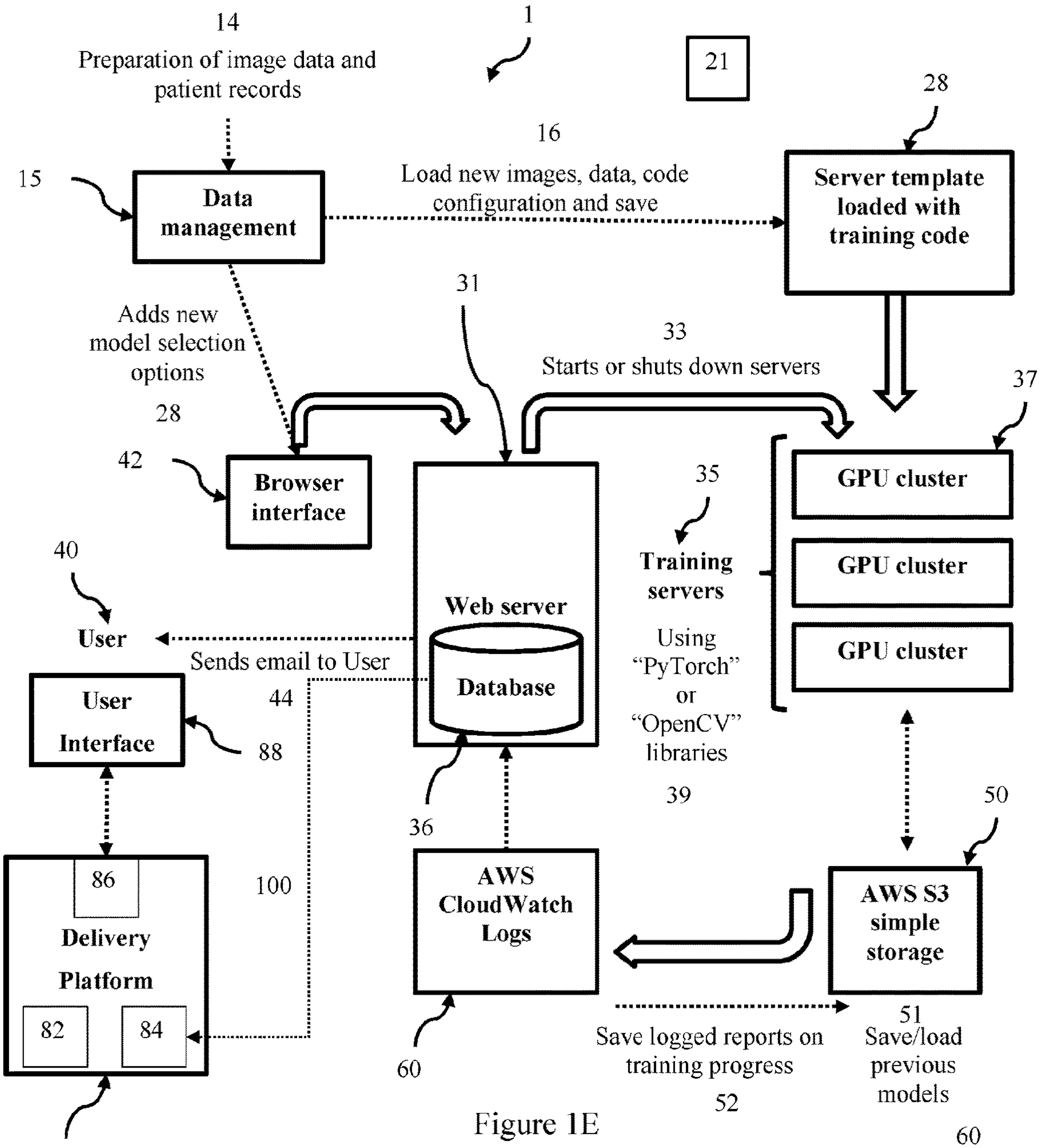
FIG. 1E is schematic architecture diagram of cloud based computation system configured to generate and use an AI model according to an embodiment.
Figure 1F:
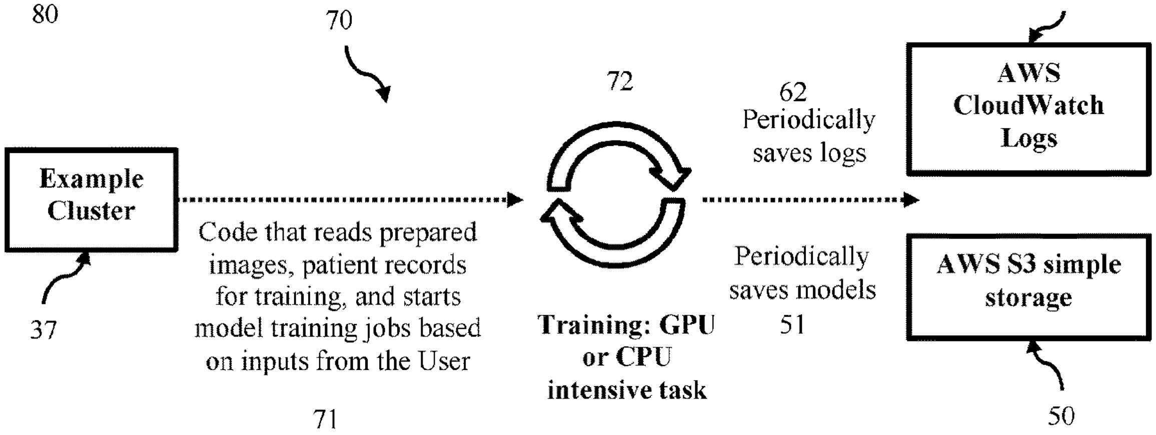
FIG. 1F is a schematic flowchart of a model training process on a training server according to an embodiment.

Embodiments of the method may be implemented in a cloud computational environment or similar server farm or high performance computing environment. FIG. 1E is schematic architecture diagram of cloud based computation system 1 configured to generate and use an AI model according to an embodiment. This is shown in the context of training an AI on healthcare data including a medical/healthcare image and associated patient medical record (including clinical data and/or diagnostic test results). FIG. 1F is a schematic flowchart of a model training process on a training server according to an embodiment.

The AI model generation method is handled by a model monitor 21 tool. The monitor 21 requires a user 40 to provide data (including data items and/or images) and metadata 14 to a data management platform which includes a data repository. A data preparation step is performed, for example to move the data items or image to a specific folder, and to rename and perform pre-processing on any images such as objection detection, segmentation, alpha channel removal, padding, cropping/localizing, normalizing, scaling, etc. Feature descriptors may also be calculated, and augmented images generated in advance. However additional pre-processing including augmentation may also be performed during training (i.e., on the fly). Images may also undergo quality assessment, to allow rejection of clearly poor images and allow capture of replacement images. The data such as patient records or other clinical data is processed (prepared) to extract a classification outcome such as viable or non-viable in binary classification, an output class in a multi-class classification, or other outcome measure in non-classification cases, which is linked or associated with each image or data item to enable use in training the AI models and/or in assessment. The prepared data may be loaded 16 onto a cloud provider (e.g., AWS) template server 28 with the most recent version of the training algorithms. The template server is saved, and multiple copies made across a range of training server clusters 37 (which may be CPU, GPU, ASIC, FPGA, or TPU (Tensor Processing Unit)-based) which form training servers 35.

The model monitor web server 31 then can apply for a training server 37 from a plurality of cloud based training servers 35 for each job submitted by the user 40. Each training server 35 runs the pre-prepared code (from template server 28) for training an AI model, using a library such as PyTorch, Tensorflow or equivalent, and may use a computer vision library such as OpenCV. PyTorch and OpenCV are open-source libraries with low-level commands for constructing CV machine learning models. The AI models may be deep learning models or machine learning models, including CV based machine learning models.

The training servers 37 manage the training process. This may include dividing the data or images in to training, validation, and blind validation sets, for example using a random allocation process. Further during a training-validation cycle the training servers 37 may also randomize the set of images at the start of the cycle so that each cycle a different subset of images are analyzed, or are analyzed in a different ordering. If pre-processing was not performed earlier or was incomplete (e.g., during data management) then additional pre-processing may be performed including object detection, segmentation and generation of masked data sets, calculation/estimation of CV feature descriptors, and generating data augmentations. Pre-processing may also include padding, normalizing, etc. of images as required. Similar processes may be performed on non-image data. That is the pre-processing step 102 may be performed prior to training, during training, or some combination (i.e., distributed pre-processing). The number of training servers 35 being run can be managed from the browser interface. As the training progresses, logging information about the status of the training is recorded 62 onto a distributed logging service such as CloudWatch 60. Metrics are calculated and information is also parsed out of the logs and saved into a relational database 36. The models are also periodically saved 51 to a data storage (e.g., AWS Simple Storage Service (S3) or similar cloud storage service) 50 so they can be retrieved and loaded at a later date (for example to restart in case of an error or other stoppage). The user 40 can be sent email updates 44 regarding the status of the training servers if their jobs are complete, or an error is encountered.

Within each training cluster 37, a number of processes take place. Once a cluster is started via the web server 31, a script is automatically run, which reads the prepared images and patient records, and begins the specific Pytorch/OpenCV training code requested 71. The input parameters for the model training 28 are supplied by the user 40 via the browser interface 42 or via a configuration script. The training process 72 is then initiated for the requested model parameters, and can be a lengthy and intensive task. Therefore, so as not to lose progress while the training is in progress, the logs are periodically saved 62 to the logging (e.g., AWS CloudWatch) service 60, and the current version of the model (while training) is saved 51 to the data (e.g., S3) storage service 51 for later retrieval and use. An embodiment of a schematic flowchart of a model training process on a training server is shown in FIG. 3B. With access to a range of trained AI models on the data storage service, multiple models can be combined together for example using ensemble, distillation or similar approaches in order to incorporate a range of deep learning models (e.g., PyTorch) and/or targeted computer vision models (e.g., OpenCV) to generate a robust AI model 108 which is then deployed to delivery platform 80. The delivery platform may be a cloud based computational system, a server based computational system, or other computational system, and the same computational system used to train the AI model may be used to deploy the AI model A model may be defined by its network weights and deployment may comprise exporting these network weights and loading them onto the delivery platform 80 to execute the final trained AI model 108 on new data. In some embodiments this may involve exporting or saving a checkpoint file or a model file using an appropriate function of the machine learning code/API. The checkpoint file may be a file generated by the machine learning code/library with a defined format which can be exported and then read back in (reloaded) using standard functions supplied as part of the machine learning code/API (e.g., ModelCheckpoint( ) and load_weights( )). The file format may directly sent or copied (e.g., ftp or similar protocols) or it be serialized and send using JSON, YAML or similar data transfer protocols. In some embodiments additional model metadata may be exported/saved and sent along with the network weights, such as model accuracy, number of epochs, etc., that may further characterize the model, or otherwise assist in constructing the model on another computational device (e.g., cloud platform, server or user computing device). In some embodiments the same computational system used to train the AI model may be used to deploy the AI model, and thus deployment comprises storing the trained AI model, for example in a memory of webserver 31, or exporting the model weights for loading onto a delivery server.

The delivery platform 80 is a computational system comprising one or more processors 82, one or more memories 84, and a communications interface 86. The memories 84 are configured to store the trained AI model, which may be received from the model monitor web server 31 via the communications interface 86 or loaded from an export of the model stored on an electronic storage device. The processors 82 are configured to receive input data via the communications interface (e.g., an image for classification from user 40) and process the input data using the stored AI model to generate a model result (e.g., a classification), and the communications interface 84 is configured to send or the model result to a user interface 88 or export to a data storage device or electronic report, the processors are configured to receive input data and process the input data using the stored trained AI model to generate a model result. A communications module 86 is configured to receive the input data and send or store the model result. The communications module may communicate with a user interface 88, such as a web application to receive the input data and to display the model result, e.g., a classification, object bounding box, segmentation boundary etc. The user interface 88 may be executed on a user computing device and is configured to allows user(s) 40 to drag and drop data or images directly onto user interface (or other local application) 88, which triggers the system to perform any pre-processing (if required) of data or image and passes the data or image to the trained/validated AI model 108 to obtain a classification or model result (e.g., objecting bounding box, segmentation boundary, etc.) which can be immediately returned to the user in a report and/or displayed in the user interface 88. The user interface (or local application) 88 also allows users to store data such as images and patient information in data storage device such as a database, create a variety of reports on the data, create audit reports on the usage of the tool for their organization, group or specific users, as well as billing and user accounts (e.g., create users, delete users, reset passwords, change access levels, etc.). The delivery platform 80 may be cloud based and may also enable product admin to access the system to create new customer accounts and users, reset passwords, as well as access to customer/user accounts (including data and screens) to facilitate technical support.

In the case of multiple data owners, AI/machine learning models may be trained that use the whole training set as a combination of individual sub-datasets. In these embodiments the trained prediction model would be able to produce accurate results on individual sub-datasets specifically and on the overall test set which is a combination of data/images from different data owners. The data owners, in practice, may be in different geographical locations. The sub-datasets from different owners can be collectively stored at a central location/server or may be distributed and kept locally at each owner's location/server to meet data privacy regulations. Embodiments of the method may be used regardless of data location or privacy restrictions.

Embodiments of the method may be used for a range of data types, including input data types (numerical, graphical, textual, visual and temporal data) and output data types (e.g., binary classification problems and multiple class (multiple labels) classification problems. In particular, numerical, graphical and textual structured data are popular data types for general machine learning models, with Deep Learning being more common for graphical, visual and temporal (audio, video) data. Output data types may include binary and multi-class data, and embodiments of the method may be used for binary classification problems as well as multiple class (multiple labels) classification problems.

Embodiments of the method may use a range of model types (e.g., classification, regression, object detection, etc.) each of which use typically use a different architecture, and within each type there is typically a range of architectures that may be used. The choice of AI model type may be based on the type of the input and the target that one wants to predict (e.g., outcome). Embodiments of the method are particularly suited to (but not limited to) supervised/classification models, and healthcare datasets such as classification of healthcare images and/or diagnostic test data (although again the use is not limited only to healthcare datasets). Models can be trained using centralized (in which the training data is stored in one geographical location) or decentralized (in which the training data is stored in multiple geographical locations separately) data sources depending on the data location and data privacy issues described above. In the case of decentralized training, the choices of model architectures and model hyper-parameters are the same as the centralized training, however the training mechanism must ensure the private data is kept privately and locally at each data owner's location.

Model outputs may be categorical (e.g., class/label) in the case of classification models or non-categorical in the case of regression, object detection/segmentation models. Embodiments of the method may be used for either classification problems, with the method may identify an incorrect label, as well as more general regression, object detection and segmentation problems, where the method may give a confidence estimate of the outcome. For example in the case of a the model estimating a bounding box, the method will estimate if the box is unacceptable, relatively good, good, very good or with some other confidence level (rather than correct/incorrect). These can then be used to decide how to clean the data. Different kinds of labels may be sensitive to different kinds of noise with respect to the image, depending on the use case for the model intended to be trained.

The choice of the AI model type (e.g., binary classification, multi-class classification, regression, object detection, etc.) will typically depend upon the specific problem the AI is to be trained/used for. The plurality of AI models trained may use a plurality of model architecture to provide a diversity of models. The plurality of model architectures may comprise a diversity of general architectures such as Random Forest, Support Vector Machine, clustering; Deep Learning/Convolutional neural network including ResNet, DenseNet, or InceptionNet), as well as the same general architecture, e.g., ResNet, but with varying internal configurations, such as a different number of layers and connections between layers, e.g., ResNet-18, ResNet-50, ResNet-101. Additional diversity can be generated by using the same model type/configuration but with different combinations of model hyper-parameters.

The AI models may include machine learning models such as computer vision models as well as deep learning and neural nets. Computer vision models rely on identifying key features of the image and expressing them in terms of descriptors. These descriptors may encode qualities such as pixel variation, gray level, roughness of texture, fixed corner points or orientation of image gradients, which are implemented in the OpenCV or similar libraries. By selection on such feature to search for in each image, a model can be built by finding which arrangement of the features is a good indicator for a desired class (e.g., embryo viability). This procedure is best carried out by machine learning processes such as Random Forest or Support Vector Machines, which are able to separate the images in terms of their descriptions from the computer vision analysis.

Deep Learning and neural networks 'learn' features rather than relying on hand designed feature descriptors like machine learning models. This allows them to learn 'feature representations' that are tailored to the desired task. These methods are suitable for image analysis, as they are able to pick up both small details and overall morphological shapes in order to arrive at an overall classification A variety of deep learning models are available each with different architectures (i.e., different number of layers and connections between layers) such as residual networks (e.g., ResNet-18, ResNet-50 and ResNet-101), densely connected networks (e.g., DenseNet-121 and DenseNet-161), and other variations (e.g., InceptionV4 and Inception-ResNetV2). Training involves trying different combinations of model parameters and hyper-parameters, including input image resolution, choice of optimizer, learning rate value and scheduling, momentum value, dropout, and initialization of the weights (pre-training). A loss function may be defined to assess performing of a model, and during training a Deep Learning model is optimized by varying learning rates to drive the update mechanism for the network's weight parameters to minimize an objective/loss function. The plurality of AI models may comprise a plurality of model architectures including similar architectures with different hyper-parameters.

Commonly, machine learning algorithms require an objective/loss function and several evaluation metrics may be used to assess the accuracy of the model being trained (which is assessed at the end of each epoch). The common loss function for a binary classification problem is binary cross-entropy (although other loss functions may be used). The loss function fundamentally measures the difference between the target (actual output label) and the model outcome (predicted output label). Other metrics that may be used to rank model epochs include the following:

Cross-entropy (log) loss CE: is a measure of the average number of bits needed (or extra information required) to identify an event drawn from a set if a coding scheme used for the set is optimized for an estimated probability distribution q rather than the true distribution p. In classification problems, the calculation of the cross entropy loss, which compares a one-hot encoded (true) probability $$p_j^{(c)}$$

distribution over classes c∈{1 . . . . C} to the estimated probability distribution $$q_j^{(c)}$$

for each element j∈{1 . . . . N}. The result is averaged over all elements (or observations) to give:

$$CE = -\frac{1}{N}\sum_{j=1}^{N}\sum_{c=1}^{C} p_j^{(c)}\log\left(q_j^{(c)}\right) \tag{1}$$

(Mean) accuracy A: is the proportion of predictions for which the model was correct (NT) compared with the total number of predictions (N). Formally, accuracy has the following definition:

$$A = N_T / N \tag{2}$$

Class-based accuracy $A^{(c)}$: is valuable when one would like to see the correct prediction rate per class $$\left(N_T^{(c)}\right).$$

The calculation is like the accuracy, but we only consider images of one class (c) at a time:

$$A^{(c)} = N_T^{(c)} / N^{(c)} \tag{3}$$

Balanced accuracy (or F1 Score) $A_{bal}$: is more suitable in cases where the data class distribution is unbalanced. Balanced accuracy is calculated as the average of the class-based accuracy for all classes c∈{1 . . . . C}:

$$A_{bal} = \frac{1}{C}\sum_{c=1}^{C} N_T^{(c)}/N^{(c)} \tag{4}$$

In general, following several epochs of training (to ensure that a model explores the solution space), cross-entropy is used as the deciding factor because it naturally expresses the confidence in a model's predictions q compared to the ground truth p. Accuracy metrics are also used secondary factors to determine tiebreaks.

Accuracy based metrics include accuracy, mean class accuracy, sensitivity, specificity, a confusion matrix, Sensitivity-to-specificity ratio, precision, negative predictive value, and balanced accuracy, typically used for classification model types, as well as mean of square error (MSE), root MSE, mean of average error, mean average precision (mAP) typically used for regression and object detection model types. Confidence based metrics include Log loss, combined class Log loss, combined data-source Log loss, combined class and data-source Log loss. Other metrics include epoch number, Area-Under-the-Curve (AUC) thresholds, Receiver Operating Characteristic (ROC) curve thresholds, and Precision-Recall curves which are indicative of stability and transferability.

The evaluation metrics can be varied depending on types of problems. For binary classification problems these may include overall accuracy, balanced accuracy, log loss, sensitivity, specificity, F1-score, Area Under Curve (AUC) including Receiver Operating Characteristic (ROC) curves, and Precision-Recall (PR) curves. For regression and object detection models these may include mean-squared-error (MSE), root MSE, mean of average error, mean average precision (mAP), confidence score and recall.

Embodiments of the methods will now be described in further detail and several examples illustrated.

In some embodiments the predictive power of the dataset 107 is first performed to explore the level of label noise in the dataset for each data source, and thus assess the data quality and in particular the label noise. If there is high label noise (i.e., low predictive power and thus implies low quality data) then embodiments of the UDC can be used to address/minimize the label noise and improve the data quality of the dataset. Alternatively, if the dataset is part of a larger collective dataset from multiple sources, it can be removed altogether (if practicable).

In one embodiment we perform a basic test to confirm that the model is working properly by splitting the dataset into train-validation-test sets and then randomizing the class labels in the training dataset. A model is then trained on the training set and tested on the validation and test sets. The balanced accuracy should be approximately 50% for both validation and test set, i.e., no predictive power because the labels in the training dataset were randomized. In this case, both the data and model are in the right order and one can implement further cleansing approaches if required. Otherwise there may exist problems with model's configuration, training algorithm or severely skewed training data. In this embodiment the balanced accuracy metric is used rather than overall accuracy because in some cases the skewed class distribution on a dataset can be associated with very high overall accuracy even though the balanced accuracy is only around 50% (see an example of this below in the experimental results section). However other metrics may be used including confidence metrics such as Log Loss.

We then proceed to test model positive predictive power: For each data source, using the original dataset with the original (non-randomized) labels, we split data into training and test set. A model is trained on the training set and tested on the test set. The balanced accuracy on the test set is considered (although other metrics such as Log Loss could be used). The closer the accuracy is to 100% (or some maximum benchmark accuracy for the specific problem domain), which is an indicator of high predictive power, then the lower the label noise in the data and the higher the data quality. The closer the accuracy is to 50% (or the accuracy calculated above when training on a randomly labeled dataset), which is an indicator of no predictive power, then the higher the label noise in the data and the lower the data quality. In one embodiment testing for positive predictive power is performed by applying a k-fold cross validation approach to the training set. That is we split the training set into k folds and for each fold train a plurality of AI models. We then obtain a first count of the number of times each sample in the validation dataset is either correctly predicted, incorrectly predicted, or passes a threshold confidence level, by the plurality of AI models. We then randomly assign a label or outcome to each sample and repeat the k-fold cross validation approach. i.e., split the randomized training set into k folds and for each fold train a plurality of AI models. We then obtain a second count of the number of times each sample in the validation dataset is either correctly predicted, incorrectly predicted, or passes a threshold confidence level, by the plurality of AI models. We can then estimate the positive predictive power by comparing the first count with the second count. If the two counts are similar the datasets has poor predictive power. If the difference is large (i.e., more than threshold count difference), and, based on what was counted, indicates that the nonrandomized data is correctly predicting labels, then the positive prediction power is high (or sufficient).

Additionally we can test model transferability: Investigate the model transferability to the validation dataset (optional) and to the test dataset. The common behavior in model training may be compromised because of bad quality training data with high label noise. Split the data into train-(optional) validation-test datasets. Train a model using the training dataset and calculate a metric such as balanced accuracy or Log Loss, and the outcome of the validation and test datasets are considered. The test and the validation accuracy results are taken at the same training epoch. Good quality data would have high correlation (or accuracy consistency) between the validation and the test datasets.

Datasets with reasonable or high label noise are candidates for embodiments of UDC described herein to reduce label noise and mitigate against poor quality data, and ultimately improve the resulting trained AI model. In this case, the following steps below will be conducted.

Embodiments of the UDC method can be used to address noisy data that appears in a sub-set of classes or in all classes within a dataset (we denote these classes Noisy Classes). We assume the remaining classes in the dataset have no or minimal noise (we denote these classes Correct Classes). In the case that the noisy labels appear in all classes, the number of Correct Classes is zero and the technique may still be employed if the level of label noise is lower than 50% in any of the classes. For simplicity, we call "incorrect" those predictions for samples (or data/datapoints within a dataset) we want to remove (or re-label) from training data:

In one embodiment we remove or re-label input samples from the training dataset that are consistently being predicted incorrectly, i.e., are "untrainable", by a plurality of models trained using k-fold cross-validation on the same training dataset (see Algorithm 1 below), and where a metric such as accuracy in the validation and/or test datasets for each model is preferred to be biased towards the Correct Classes in the cases there exist at least one Correct Class (there is no class-specific bias in the cases that all classes are Noisy Classes). It is proposed that the best chance for an AI model to learn patterns associated with the classification (or label) for each sample is in the training dataset itself which is used to train the AI model. This cannot be guaranteed in the validation and test datasets because there may not be a representative sample in the training dataset. The reason mis-labeled samples are untrainable in the training dataset is because they belong to an alternative class that we know (or are confident) is a Correct Class.

If the AI model correctly trains and classifies samples in the Correct Class (which is the case if we bias the accuracy in the validation/test datasets towards the Correct Classes), then the model is unlikely to be able to correctly classify mis-labeled samples in the Noisy Class (because it would look like a sample from the Correct Class and result in an incorrect prediction or classification). There is one case where this argument may not hold, which is when the AI model is overtrained or over-fitted to the dataset. However, this case can be easily detected by a drop in accuracy in the validation and/or test dataset, and thus these models can be excluded from the analysis. The steps in this embodiment are as follows.

The aggregated dataset ($\mathbb{S}$) contains data from d different data owners (individual datasets $(\mathbb{D}^{s})^{S}$). Each dataset ($\mathbb{D}^{s}$) is divided into training and validation sets (a test set is optional) using k-fold cross-validation (KFXV). A set of n model architectures ($\mathbb{M}$) are trained using KFXV (a total of n×k models) on the training dataset. Classes may be identified (or predetermined) as Correct Classes or Noisy Classes based on the specific problem. In cases that at least one Correct Class exists, the set of learned models ($\mathbb{F}^{S}$) is selected where, for each model, both the accuracy for the Correct Classes (first priority) and balanced accuracy (second priority) are high, with confidence metrics such as cross-entropy loss used as tiebreakers. However other combinations or priority ordering of metrics may be used such as a confidence based metric as a primary metric. Models where the Noisy Classes have high accuracy should be avoided because it implies that the AI model has trained to mis-classify data. In the cases that there are no Correct Classes, models with highest balanced accuracy (again, using cross-entropy loss as a tiebreaker) are selected. That is we can define one or more thresholds for the Correct Classes and a threshold for the Noisy Classes. Further, whilst the above example uses accuracy and balanced accuracy, but a single metric may be used or other combinations or priority ordering of metrics. The metrics may also be a confidence based metric such as Log Loss (which may be used as a primary metric).

For each dataset in ($\mathbb{S}$), run each AI model in $\mathbb{F}^{S}$ over the entire training dataset $(\mathbb{D}^{S})^{S}$. The AI model's classification (or prediction) for each sample $$(z_j^s)$$

in the training dataset can be compared with its assigned label/class to determine if the sample was correctly or incorrectly classified.

List all the samples in the Noisy Classes that are consistently predicted as incorrect by multiple selected models, using a heuristic guide to determine an optimal value or window of values of a so-called consistency threshold ($l^{opt}$), where $l^{opt}$ is calculated using Algorithm 2 below and defines a cut-off threshold of the number of successful predictions below which an image is deemed to be mis-labeled or "untrainable". A second supporting measure for identifying mis-labeled data is to give priority to samples that the model got "really wrong", i.e., the model gave the sample a high incorrect AI score (e.g., when the model should have given the sample a score of 1 for the class, it gave it a score of 0 because it was confident that the sample was from a different class).

Ignore repeated incorrect predictions from samples in the Correct Classes because it is unclear whether the sample in the Correct Class is mis-labeled; or whether the AI models have persistently trained to correctly classify mis-labeled data forcing the correctly labeled data to be persistently incorrect.

Remove or re-label these samples and re-train these models with the "cleansed dataset" using the same network architectures and configurations. Check that the re-trained AI models have improved their performance (e.g., accuracy and generalizability) on the same validation and test dataset, indicating an improvement in both data quality and resulting trained AI models.

In the case where there are multiple datasets from multiple data-sources (or data owners), perform the data cleansing in (a) above to each sub-dataset, enabling the removal or re-labeling of mis-labeled samples from each sub-dataset. Aggregate the multiple sub-datasets for machine learning training. An optional step is to perform the data cleansing in (a) above again on the aggregated dataset to remove any remaining mis-labeled samples. Finally train machine learning models on the aggregated and cleansed dataset.

In order to represent the above methodology in a more algorithmic way, the following will show how it works, first in a centralized manner, and then for a de-centralized case. Users can choose a suitable cleaning function specific to the problem at hand.

A dataset can be tested for predictive power (recommended before applying the UDC method described in Algorithms 2 and 3) using Algorithm 1 as outlined below. Either a single model or a plurality of models is first trained on each dataset $\mathbb{D}$ containing samples $z_j=(x_j, \hat{y}_j)$, with images $x_j$ and (noisy) target labels $\hat{y}_j$. If models trained on this data score no better than when trained with the same data but using random labels $$\hat{y}_j^{(rand)},$$

the label noise in the data is so high as to make the dataset untrainable. Such a dataset is a candidate for UDC.

Algorithm 1 can, in a slightly different form, be used to determine model transferability of an individual dataset $\mathbb{D}$ from a single data source by splitting it into training, validation and test sets, and comparing the results of the validation and test sets using confidence metrics such as CE loss or accuracy scores such as balanced accuracy. If there is very low correlation or consistency in results between the validation and test datasets, the dataset $\mathbb{D}$ can be marked as containing low quality data. The UDC method can then be applied individually on $\mathbb{D}$ to address the suspected high label noise. If the label noise is so high as to render even the UDC method impracticable, for instance when about 50% of labels in each class are incorrect, consider removing $\mathbb{D}$ altogether. In such a case, $\mathbb{D}$ would be an untrainable dataset.

The UDC algorithm for a single data source (with dataset $\mathbb{D}$) is shown in the pseudo-code in Algorithms 2 and 3. The technique is based on k-fold cross-validation (KFXV), using multiple model architectures to identify noisy labels by exploiting the fact that a noisy label is more likely to be classified as wrong by multiple models. The use of the KFXV ensures that all samples are given the same number of passes through the UDC algorithm. Algorithm 2 counts and returns the number of successful predictions $s_j$ per element $z_j$, which is used as an input to Algorithm 3.

Using Algorithm 3, a histogram is generated that bins together images with the same number of successful predictions $\hbar_l \leftarrow \|\{s_j|s_j=l\}\|_0$, where bin l contains images that were successfully predicted by l models (0<l<n×k). A cumulative histogram $$\mathcal{H}_l \leftarrow \sum_{i=0}^{l} \hbar_i$$

is then used to calculate a percentage difference operator $$\Delta\tilde{\mathcal{H}}_{l-1} \leftarrow 2\frac{h_l}{\mathcal{H}_l + \mathcal{H}_{l-1}} (l \neq 0).$$

When the number of models is large enough, this measure acts as a good differentiator between good labels, which are unlikely to be identified incorrectly and will thus cluster in bins with higher values of l, and bad labels, which are very likely to be identified incorrectly and will thus cluster in bins with lower values of l. The denominator acts as a filter, biasing the measure toward larger bins and avoiding those containing very few images. Therefore, a heuristic measure of the consistency threshold $l^{opt} \leftarrow \text{argmin}_l(\Delta\tilde{\mathcal{H}}_l)$ is used as a rough guide to differentiate good labels from bad ones.

This consistency threshold is used to identify all elements $z_j$ for which $s_j<l^{opt}$, which represents images that are "consistently" incorrectly predicted. These elements are then removed from the original dataset $\mathbb{D}$ to produce a new, cleansed dataset, $\tilde{\mathbb{D}}$.. The procedures in Algorithms 2 and 3 can then be repeated multiple times until either a predetermined performance threshold is met, or until model performance is optimized.

The UDC algorithm is extended for multiple data sources (UDC-M) in the Algorithm 4, based on the same algorithms as for a single data source (k-fold cross-validation), where the predictive power of the various datasets must first be considered. This algorithm takes as input a set $\mathbb{S}$ made up of d individual datasets $\mathbb{D}^{(s)}$,, where s∈{1 . . . d}. Before applying the UDC method from Algorithm 2 and 3, each dataset is tested for predictive power using Algorithm 1 to determine those datasets that are untrainable. Such datasets $$\mathbb{D}_{UDC}^{(s)}$$

are candidates for UDC-M, as the remaining trainable datasets $$\mathbb{S} \backslash \mathbb{D}_{UDC}^{(s)}$$

can be used to cleanse $$\mathbb{D}_{UDC}^{(s)}$$

as described below.

Algorithm 1

Algorithm 1 - A given dataset $\mathbb{D}$ with N elements $z_j = (x_j, \hat{y}_j)$ can be tested for predictive power by first training a plurality of models to learn the mapping between images $x_j$ and (noisy) target labels $\hat{y}_j$. Then, the learned mappings are tested and scored using the training data as the test data. If these learned mappings perform no better than when the same procedure is followed but with (random) target labels $\hat{y}_j^{(rand)}$, the dataset $\mathbb{D}$ is untrainable.

Define predictive_power($\mathbb{D}$, k, $\mathbb{M}$, A, ϵ):
Require: $\mathbb{D}$, the given dataset with N elements $z_j = (x_j, \hat{y}_j)$; image $x_j$, noisy target label $\hat{y}_j$
Require: k, the number of folds used to split dataset $\mathbb{D}$ in k mutually exclusive subsets $\mathbb{D}^{(i)}$
Require: $\mathbb{M}$, a set of n model architectures with elements $M^{(m)} \in \mathbb{M}$, where m ∈ {1, . . . , n}
Require: A, the learning algorithm, maps a dataset and a model into a learned function $f^{(i,m)}$
Require: ϵ, a threshold percentage value used to determine predictive power
Initialize: predictive ← False, c ← 0, r ← 0
  Split $\mathbb{D}$ into k mutually exclusive validation subsets $\mathbb{D}^{(i)}$, whose union is $\mathbb{D}$
  for m from 1 to n do
  for i from 1 to k do
    $f^{(i,m)} \leftarrow A(M^{(m)}, \mathbb{D} \backslash \mathbb{D}^{(i)})$
    for $z^{(j)}$ in $\mathbb{D}$ do
      if $\hat{y}_j = \overline{y}_j^{(i,m)} \leftarrow f^{(i,m)}(x_j)$ do
      c ← c + 1
      end if
      if $\hat{y}_j = \hat{y}_j^{(rand)}$ do
    r ← r + 1
      end if
    end for
  end for
end for
if $\frac{100}{n \times k}\left|\frac{c}{N} - \frac{r}{N}\right| > \epsilon$ do
predictive ← True
end if
Return predictive

Algorithm 2

A given dataset $\mathbb{D}$ contains a set of N elements $z_j = (x_j, \hat{y}_j)$ with each image $x_j$ paired with its corresponding (noisy) target label $\hat{y}_j$ (e.g., $\hat{y}_j \in \{0, 1\}$ for binary classification problem), where j ∈ {1 . . N}. $\mathbb{D}$ (excluding a subset used as a blind test set) is split into k mutually exclusive validation datasets $\mathbb{D}^{(i)}$ with training sets $\mathbb{D} \backslash \mathbb{D}^{(i)}$, where i ∈ {1 . . k} is the cross-validation phase index. A set of model architectures $\mathbb{M}$ with n elements $M^{(m)} \in \mathbb{M}$, where m ∈ {1, .. , n}, is trained on each dataset $\mathbb{D} \backslash \mathbb{D}^{(i)}$. Algorithm A is used to produce a set of learned mappings $\mathbb{F} \ni f^{(i,m)} \leftarrow A(M^{(m)}, \mathbb{D} \backslash \mathbb{D}^{(i)})$, which are chosen using confidence metrics described above. Phase index i is included in the learned mapping since each model is trained on a different dataset $\mathbb{D} \backslash \mathbb{D}^{(i)}$), and because dropout is used during training. These learned mappings can then be tested against the entire dataset $\mathbb{D}$ to generate predicted outcomes $\overline{y}^{(i,m)} \leftarrow f^{(i,m)}(x_j)$, which can be used to find a per-element successful prediction count $\mathcal{S}_j = {}^{(k,n)}_{(i=1,m=1)}\Sigma\Sigma\, \mathcal{S}_j^{(i,m)}$, where $\mathcal{S}_j^{(i,m)}$ is 1 if the model prediction equals the noisy target label, or $\hat{y}_j = \overline{y}_j^{(i,m)} \leftarrow f^{(i,m)}(x_j)$, and 0 otherwise. The vector s containing all -continued

Algorithm 2 elements $s_j \in \{0 \,..\, n \times k\}$ is returned.
Define generate_UDC_samples($\mathbb{D}$, k, $\mathbb{M}$, A):
Require: $\mathbb{D}$, the given dataset with N elements $z_j = (x_j, \hat{y}_j)$; image $x_j$, noisy target label $\hat{y}_j$
Require: k, the number of folds used to split dataset $\mathbb{D}$ in k mutually exclusive subsets $\mathbb{D}^{(i)}$
Require: $\mathbb{M}$, a set of n model architectures with elements $M^{(m)} \in \mathbb{M}$, where $m \in \{1, \ldots, n\}$
Require: A, the learning algorithm, maps a dataset and a model into a learned function $f^{(i,m)}$
Initialize: $s \leftarrow 0_N$
  Split $\mathbb{D}$ into k mutually exclusive validation subsets $\mathbb{D}^{(i)}$, whose union is $\mathbb{D}$
  for m from 1 to n do
  for i from 1 to k do
    $f^{(i,m)} \leftarrow A(M^{(m)}, D \backslash D^{(i)})$
    for $z^{(i)}$ in D do
      if $\hat{y}_j = \overline{y}_j^{(i,m)} \leftarrow f^{(i,m)}(x_j)$ do
      $s_j \leftarrow s_j + 1$
      end if
    end for
  end for
end for
Return $s$

Algorithm 3

Given the vector s containing all elements $s_j$, a histogram $h_l$ is generated that counts the number of elements $s_j$; that fall into a bin l, where $l \in \{0 \,..\, L\}$ represents the number of successful predictions, and $L = n \times k$ is the total number of models used in the UDC algorithm (Algorithm 2). In other words, the operation used to generate the histogram $h_l \leftarrow \|\{s_j | s_j = l\}\|_0$ calculates the total number of elements in s for which $s_j = l$, where $\|\mathbb{A}\|_0$ returns the size of the set $\mathbb{A}$. The cumulative histogram $\mathcal{H}_l = \sum_{i=0}^{l} h_i$ is then calculated, and a weighted difference operator $\Delta\tilde{\mathcal{H}}_l$ minimised to determine the optimal strictness threshold, $l^{opt} = \mathrm{argmin}_l(\Delta\tilde{\mathcal{H}}_l)$. The algorithm then returns the list of good labels $z \backslash z_{UDC}$, where $z_{UDC}$ are identified as bad labels as they do not meet the threshold $\{s_j | s_j < l^{opt}\}$. Once these labels are identified, the new cleansed dataset $\tilde{\mathbb{D}}$ containing elements $z \backslash z_{UDC}$ can be used to re-train models with better performance. This process can be repeated iteratively until a pre-determined level of performance is achieved or until the UDC procedure yields no further improvements.
Define good_labels($\mathbb{D}$, k, $\mathbb{M}$, A):
Require: $\mathbb{D}$, the given dataset with N elements $z_j = (x_j, \hat{y}_j)$; image $x_j$, noisy target label $\hat{y}_j$
Require: k, the number of folds used to split dataset $\mathbb{M}$ in k mutually exclusive subsets $\mathbb{D}^{(i)}$
Require: $\mathbb{M}$, a set of n model architectures with elements $M^{(m)} \in \mathbb{M}$, where $m \in \{1, \ldots, n\}$
Require: A, the learning algorithm, maps a dataset and a model into a learned function $f^{(i,m)}$
Initialize: $h \leftarrow 0_{n \times k}$
  s ← generate_UDC_samples($\mathbb{D}$, k, $\mathbb{M}$, A)
  $h_0 \leftarrow \|\{s_j | s_j = 0\}\|_0$
  $\mathcal{H}_0 \leftarrow h_0$
  $L \leftarrow n \times k$
  for l from 1 to L do
  $h_l \leftarrow \|\{s_j | s_j = l\}\|_0$
  $\mathcal{H}_l \leftarrow \sum_{i=0}^{l} h_i$
    $\Delta\tilde{\mathcal{H}}_{l-1} \leftarrow 2h_l(\mathcal{H}_l + \mathcal{H}_{l-1})^{-1}$
  end for
  $l^{opt} \leftarrow \mathrm{argmin}_l(\Delta\tilde{\mathcal{H}}_l)$ -continued

Algorithm 3

$z_{UDC} \leftarrow \{z_j | s_j < l^{opt}\}$
  $\tilde{\mathbb{D}} \leftarrow z \backslash z_{UDC}$
  Return $\tilde{\mathbb{D}}$

Algorithm 4

Given a set $\mathbb{S}$ of d individual datasets $\mathbb{D}^{(s)}$, first determine using Algorithm 3 the set of data sources in in $\mathbb{S}$ that have predictive power ($\tilde{\mathbb{S}}$ & $\mathbb{S} \backslash \mathbb{S}_{UDC}$), where $\mathbb{S}_{UPC}$ is a set of datasets that do not have predictive power and are thus deemed to be untrainable on their own. The UDC method is then applied to remove untrainable samples from each of the trainable datasets $\tilde{\mathbb{D}}^{(s)}$ in $\tilde{\mathbb{S}}$. These individually cleansed datasets are then aggregated into a larger dataset containing only the trainable datasets $\mathbb{D}_{agg} \ni \tilde{\mathbb{D}}^{(s)}$.The UDC method can optionally be applied on the aggregated dataset producing a final cleansed aggregate dataset $\tilde{\mathbb{D}}_{agg}$ Finally, untrainable datasets can be combined with Dagg to perform a final round of cleansing to remove the noisy samples from the otherwise untrainable datasets in $\mathbb{S}_{UDC}$.
Define UDC_M($\mathbb{S}$, k, $\mathbb{M}$, A, $\epsilon$):
Require: S, the given set S of d individual datasets $\mathbb{D}^{(s)}$
Require: k, the number of folds used to split dataset D in k mutually exclusive subsets $\mathbb{D}^{(i)}$
Require: $\mathbb{M}$, a set of n model architectures with elements $M^{(m)} \in \mathbb{M}$, where $m \in \{1, \ldots, n\}$
Require: A, the learning algorithm, maps a dataset and a model into a learned function $f^{(i,m)}$
Require: $\epsilon$, a threshold percentage value used to determine predictive power
Initialize: $\mathbb{S}_{UDC} \leftarrow \{\emptyset\}$, $\mathbb{D}$agg ← $\{\emptyset\}$, u ← 1
  for s from 1 to d do
    if predictive_power($\mathbb{D}^{(s)}$, k, $\mathbb{M}$, A, $\epsilon$) = True do
    $\tilde{\mathbb{D}}$(s) <- good_labels($\mathbb{D}$)(s), k, $\mathbb{M}$, A)
    $\mathbb{D}_{agg} \leftarrow \mathbb{D}_{agg} \cup \tilde{\mathbb{D}}^{(s)}$
    else do
    $\mathbb{D}^{(u)} \leftarrow \mathbb{D}^{(s)}$
    u ← u + 1
    end if-else
  end for
  $\tilde{\mathbb{D}}_{agg} \leftarrow$ good_labels($\mathbb{D}_{agg}$, k, $\mathbb{M}$, A)
  (optional) for i from 1 to u do
    $\overline{\mathbb{D}}_{agg}^{(i)} \leftarrow \mathrm{good\_labels}(\mathbb{D}_{agg} \cup \mathbb{D}^{(i)}, k, \mathbb{M}, A)$
    $\mathbb{S}_{UDC} \leftarrow \mathbb{S}_{UDC} \cup (\overline{\mathbb{D}}_{agg}^{(i)} \backslash \mathbb{D}_{agg})$
  end for
  Return $\tilde{\mathbb{D}}$agg, $\mathbb{S}_{UDC}$

Algorithm 5

A given dataset $\mathbb{D}$ contains a (labeled) training dataset $\mathbb{D}^{(train)}$ and another unlabeled dataset $\mathbb{D}^{(UDL)} = \mathbb{D} \backslash \mathbb{D}^{(train)}$ for labeling via the UDL method. Similar in nature to the UDC method, the UDL method inserts data into the training process and uses training-based inference to confidently determine labels for unlabeled data.
Define UDL($\mathbb{D}$, k, $\mathbb{M}$, A, C, $\mathcal{L}$, $\epsilon$):
Require: $\mathbb{D}$, the given dataset including $\mathbb{D}^{(train)}$ and $\mathbb{D}^{(UDL)} = \mathbb{D} \backslash \mathbb{D}^{(train)}$
Require: k, the number of folds used to split dataset D in k mutually e xclusive subsets $\mathbb{D}^{(i)}$
Require: $\mathbb{M}$, a set of n model architectures with elements $M^{(m)} \in \mathbb{M}$, where $m \in \{1, \ldots, n\}$
Require: A, the learning algorithm, maps a dataset and a model into a learned function $f^{(i,m)}$
Require: C, the number of labels to be used (depending on inferencing approach)

-continued

Algorithm 5

Require: $\mathcal{L}$, the labeling method (random or inference-based) to initialize unseen labels
Initialize: $\boldsymbol{s}^{(c)} \leftarrow O_N$
for c in C do
for $z^{(c,j)}$ in $\mathbb{D}^{(UDL)}$ do $\hat{y}_j^{(c)} = \mathcal{L}(x^{(c,j)})$ end for
$\boldsymbol{s}^{(c)} \leftarrow$ generate_UDC_samples($\mathbb{D}$, k, $\mathbb{M}$, A)
end for
for $z^{(j)}$ in $\mathbb{D}^{(UDL)}$ do
if C = 1 do if $\mathcal{S}_j^{(c)} > 1^{UDL}$ do $\hat{y}_j = c$
else do
$\hat{y}_j = \bar{c}$ (i.e., all that can be said in this case is that the label is "not" c)
end if-else
else do $\hat{y}_j \leftarrow \text{argmax}_c(\mathcal{S}_j^{(c)})$ end if-else
end for
Return $\boldsymbol{s}$ A series of cases studies will now be described. The datasets used for the following experiments are image-based and used within the context of binary classification. In these cases balanced accuracy is used as the assessment metric, however it is to be understood that other metrics could have been used including confidence based metrics such as log loss. Results are split into three types of datasets:

Cats versus dogs: A benchmark (Kaggle) dataset of 24,916 cat and dog images is used to establish certain useful relationships since the ground truth is discernible to the human eye and models with high confidence and accuracies near and even above 99% can be achieved. Synthetic noise is added to this dataset to test the merits of the UDC method under various noise and consistency threshold levels. The heuristic algorithm shown in Algorithm 3 is shown to act a useful guide for the selection of consistency thresholds. The UDC method is shown to be resilient to even extreme levels of noise (up to 50% label noise in one class while the remaining class is relatively clean), and even significant symmetric noise (30% label noise) in both classes. The UDC method does fail, however, when the label noise in both classes is 50%. In this case, model training is impossible as the model is pulled away from convergence by an equal number of true/false positives/negatives, making such data uncleansable.

Pediatric chest x-rays: Another benchmark (Kaggle) dataset of 5,856 chest x-ray images (split into 5,232 training and 624 test images) is used to classify images as "Normal" or "Pneumonia" of children from 1 to 5 years old. This dataset is shown to behave differently for the training and test sets, where the accuracy of the training set decreases sharply when the test set is included. For this reason, we treat the test set as a separate "data source" and use Algorithm 4 to clean the test set. Performance improvements are shown when removing even modest amounts of UDC-identified noisy labels. Furthermore, even while leaving the test set as a blind set, significant improvement in the test set is achieved when cleaning only the training set.

Embryo (at day 5) images: Images of embryos can be labeled "Non-Viable" or "Viable" (Non-Viable and Viable classes, respectively). Due to the complicated factors involved in determining embryo viability (see FIG. 1), where the ground truth can never be known, a proxy for the ground truth must be used. In this work, "Viable" embryos are those embryos that have been transferred to a patient and have led to a pregnancy (heartbeat after 6 weeks). "Non-Viable" embryos are those that have been transferred to a patient and did not lead to a pregnancy (no heartbeat after 6 weeks). Using domain knowledge of the problem, we know that "Viable" embryos are an accurate ground truth outcome-because a pregnancy has resulted, regardless of the impact of any other variables on the outcome, so there is negligible label noise in the Viable class. However, non-viable embryos may not have an accurate ground truth because other factors (patient, medical or IVF process factors) may result in a non-pregnancy. Therefore, there is potential for significant label noise in the Non-Viable class.

Case Study 1: Cats and Dogs

The approach to first test the effect and removal of synthetic noise on a dataset of cat and dog images is done for a very important reason. This "easy problem" can act as a baseline since it is possible to manually confirm ground truth for each image, whereas in more "difficult problems" such as classification of diseases via medical imaging, this is often impossible. The idea is to use findings derived from this "easy problem" that can translate usefully to more "difficult problems". In later sections, the findings found from this "easy problem" are used to improve the performance for difficult recognition tasks such as detection of pneumonia in chest x-ray images, and classification of embryo viability from (day 5) embryo images.

Preprocessing

In order to ensure a proper baseline for the experiment, the datasets are preprocessed in two ways. First, images are manually filtered to remove image data noise (clear outliers such as images of houses, etc., i.e., not containing cats or dogs). Second, images are identified by a unique hash key and any duplicates are removed from the entire dataset to avoid biased results. The size of the dataset after these preprocessing steps is 24,916 images in the training set and 12,349 images in the test set.

Case Study 1A: Effect of Synthetic Label Noise on Model Performance

To characterize the effect of label noise on model performance, the addition of synthetic noise (flipped labels) is performed in a systematic fashion as follows:

The (preprocessed) dataset is split into three subsets:

Training set, $\mathcal{T}^{train}$—total of 24,916 images (12,453 cats, 12463 dogs).

Test set, $\mathcal{T}^{test}$—total of 12,349 images (6,143 cats, 6,206 dogs)

Two kinds of label noise are introduced:

Uniform (labels flipped in equal proportion in both classes)

Asymmetric (labels flipped in one class only-when class distributions between classes are similar, either class can be chosen as the noisy class)

Flip level, $n_i$ (percentage of labels flipped per class i) is varied from 0% to 70%:

In the training set only $$(n_i^{test} = 0)$$

In the test set only $$\left(n_i^{train}=0\right)$$

In both training and test sets $$\left(n_i^{test}=n_i^{train}\right)$$

Figure 2:
FIG. 2 is an example of an image of a dog that is easily confused as a cat by otherwise very accurate models.

In order to compare results, the baseline accuracy is first determined by training an AI model (using a pre-trained ResNet18 architecture) on a cleansed training set (i.e., $\mathcal{T}^{train}$ with $n^{train}$=0). This model, when tested on a cleansed test set (i.e., $\mathcal{T}^{test}$ with $n^{test}$=0), reaches a balanced accuracy of about 99.2%, where the remaining 0.8% (about 200 images) is due to hard-to-classify images such as that shown in FIG. 2 which is an image 200 of a dog 292 that is easily confused as a cat by otherwise very accurate models.

Figure 3A:
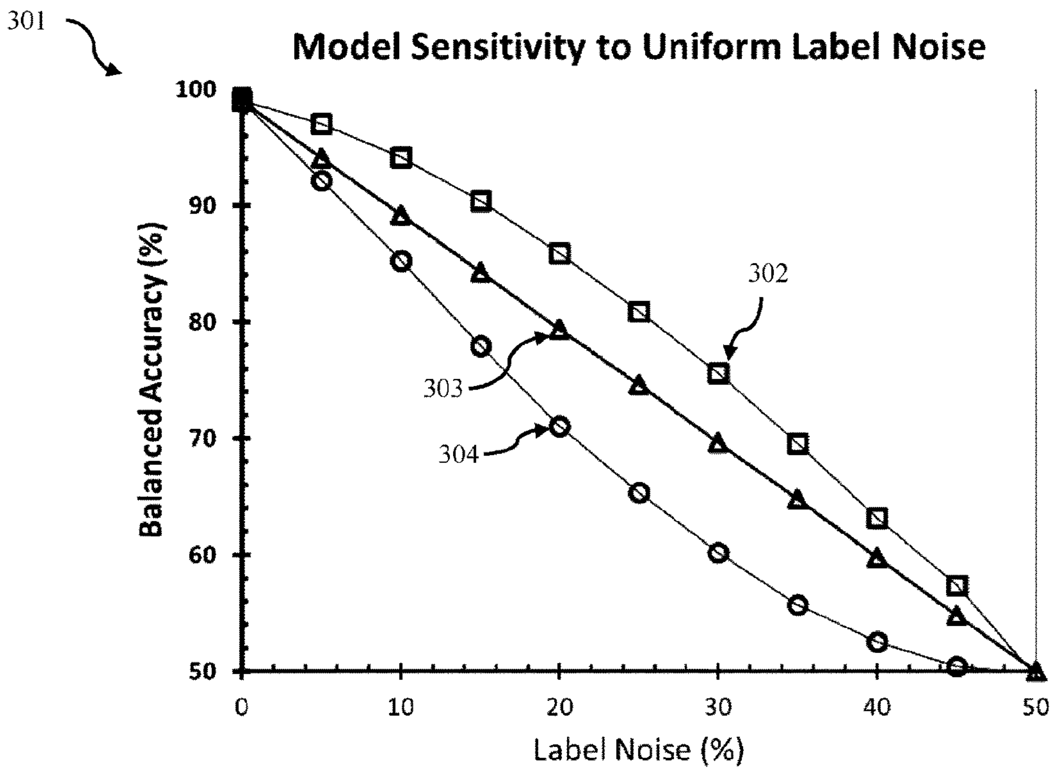
FIG. 3A is a plot of Balanced accuracy for trained models measured against a test set $\mathcal{T}^{test\ test}$ with uniform label noise in the training data only (■), in the test set only (▲) and in both sets equally (●) according to an embodiment.
Figure 3B:
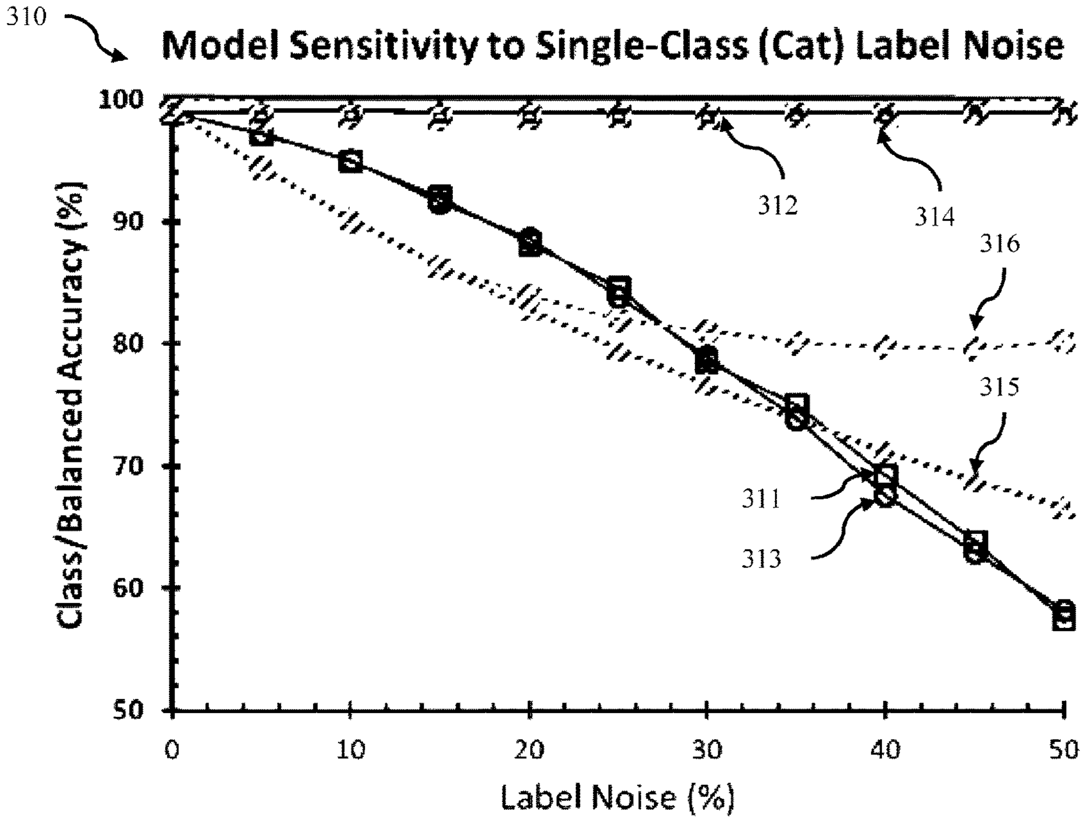
FIG. 3B is a plot of Balanced accuracy for trained models measured against a test set $\mathcal{T}^{test\ test}$ with single class noise in the training data only (■), in the test set only (▲) and in both sets equally (●) for cat class (dark line) and dog class (dashed line) according to an embodiment.

FIG. 3A is a plot of balanced accuracy for trained models measured against a test set $\mathcal{T}^{test}$ with uniform label noise in the training data only (■) 302, in the test set only (▲) 303 and in both sets equally (●) 304 according to an embodiment. FIG. 3B is a plot of Balanced accuracy (for trained models measured against a test set $\mathcal{T}^{test}$ with single class noise in the training data only (■) (solid 311 for cat, dashed 314 for dog), in the test set only (▲) (solid line 313 for cat, dashed line 315 for dog) and in both sets equally (●) (solid line 313 for cat, dashed line 316 for dog) according to an embodiment. In the uniform noise case (a) the balanced accuracy is the same as class accuracy (solid line for cat, dashed line for dog) so in this case, class accuracy is not shown, whereas when noise is symmetric (b) class accuracy shows much more useful information, with the effect of noise in the training set only resulting in opposite behavior to that in the test set only.

The results in FIGS. 3A and 3B show how the generalization error varies as $n^{train}$ and $n^{test}$ are varied; whether the noise is in the training set only, test set only (to check that the introduction of synthetic noise results in the expected linear behavior seen below), or both sets, and whether the noise is uniformly distributed between classes (FIG. 3A) or in one class only (FIG. 3B), where a percentage $n_{cat}$ of cat (Correct Class) images have their labels flipped, increasing the label noise in the dog (Noisy Class) images. Since the class distributions are similar, the cat class was arbitrarily chosen as the Correct Class for the purposes of this experiment. In the case asymmetric label noise experiment (FIG. 3B), it is interesting to note how class-based accuracy depends on the location of label noise. For instance, if the label noise is only in the training set, the model's concept of a cat becomes confused so it will incorrectly classify some cats as dogs, whereas when the label noise is only in the test set, the "dog" class will now contain images of cats, which the model will of course get wrong.

Case Study 1B: Identification and Removal of Label Noise Using UDC

To test the UDC algorithm, we add synthetic label noise to the training dataset of 24,916 images (the test set is not used in this experiment), which is split 80/20 into training and validation sets with the following parameters used for each study t, where $$n^{(t)}=\left(n_{cat}^{(t)},n_{dog}^{(t)}\right)$$

contains the fractional level of flipped labels for cat and dog classes, respectively, and where 0≤$n$ (%)≤100:

TABLE 1

Parameters used to test Untrainable Data Cleansing (Algorithms 1 and 2)

| k | n | $M^{(1)}$ | $M^{(2)}$ | $M^{(3)}$ | $n^{(1)}$ |
|---|---|---|---|---|---|
| 5 | 3 | DN-121 | RN-50 | RN-18 | (35, 5) |

| $n^{(2)}$ | $n^{(3)}$ | $n^{(4)}$ | $n^{(5)}$ |
|---|---|---|---|
| (50, 5) | (30, 30) | (70, 70) | (50, 50) |

Figure 4A:
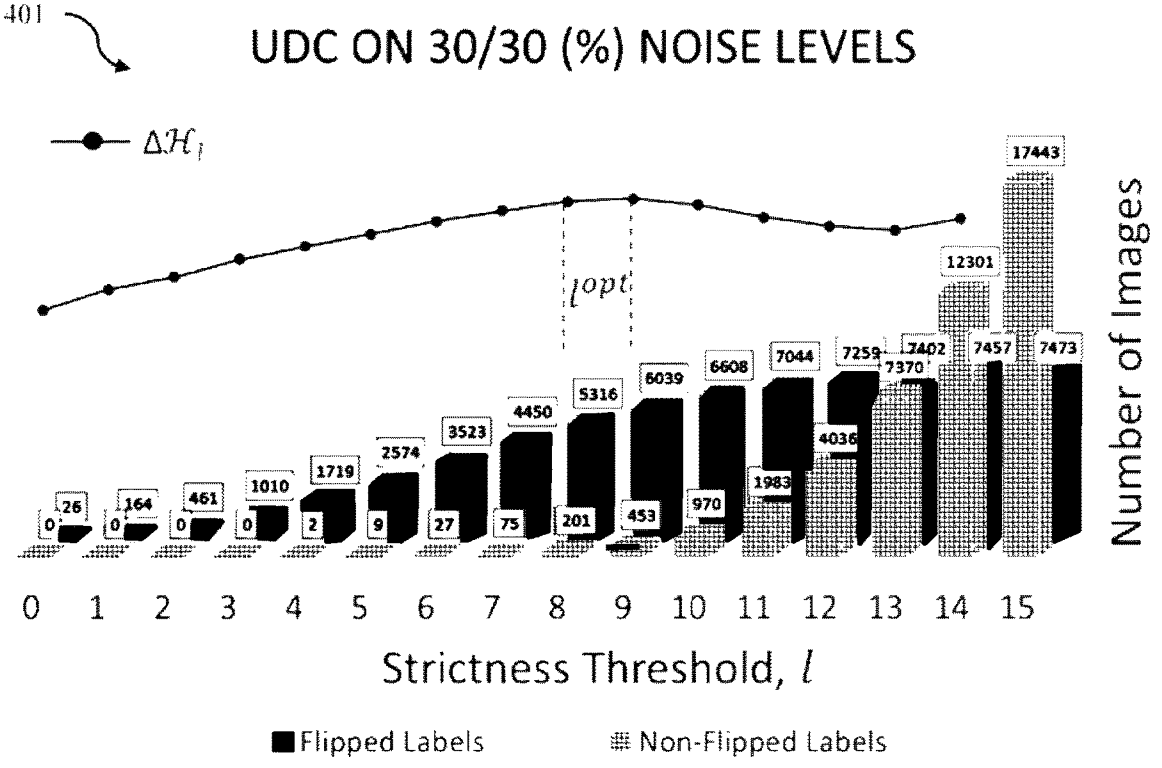
FIG. 4A is a plot of the cumulative histogram $\mathcal{H}_{l\ 1}$ at various strictness levels, l for uniform noise levels for the 30/30 case according to an embodiment.
Figure 4B:
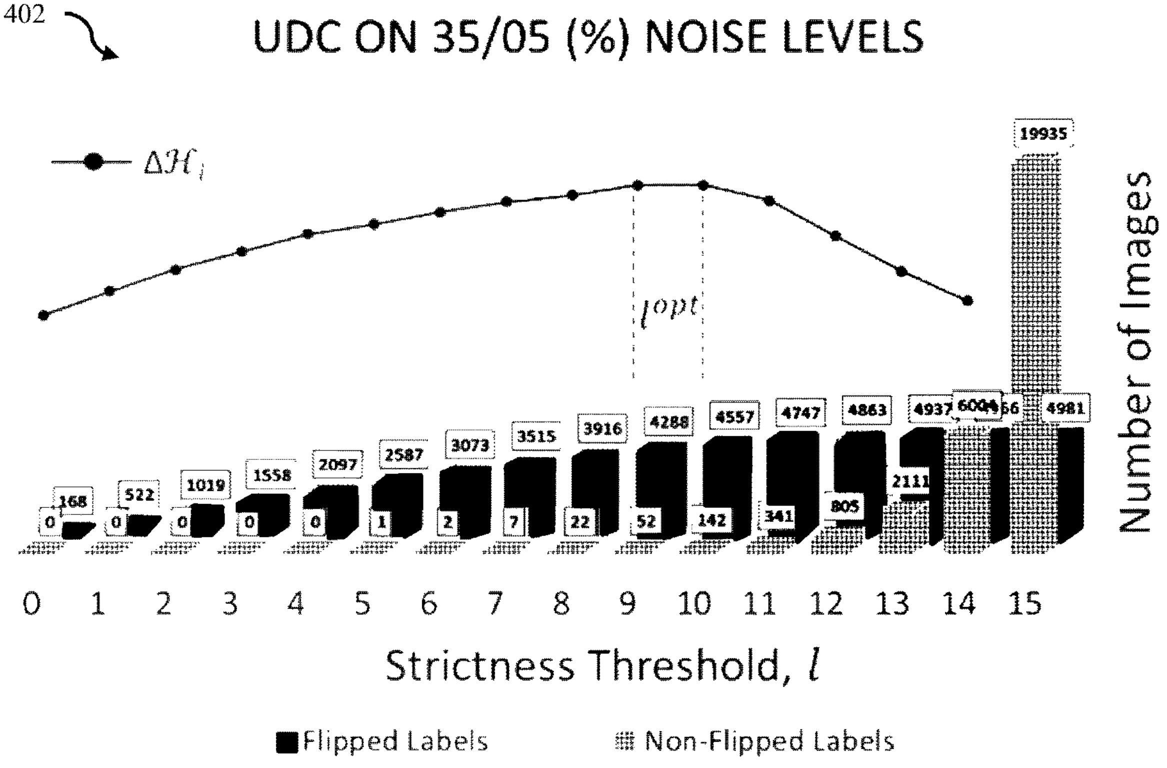
FIG. 4B is a plot of the cumulative histogram $\mathcal{H}_{l\ 1}$ at various strictness levels, l for asymmetric noise levels for the 35/05% case according to an embodiment.
Figure 4C:
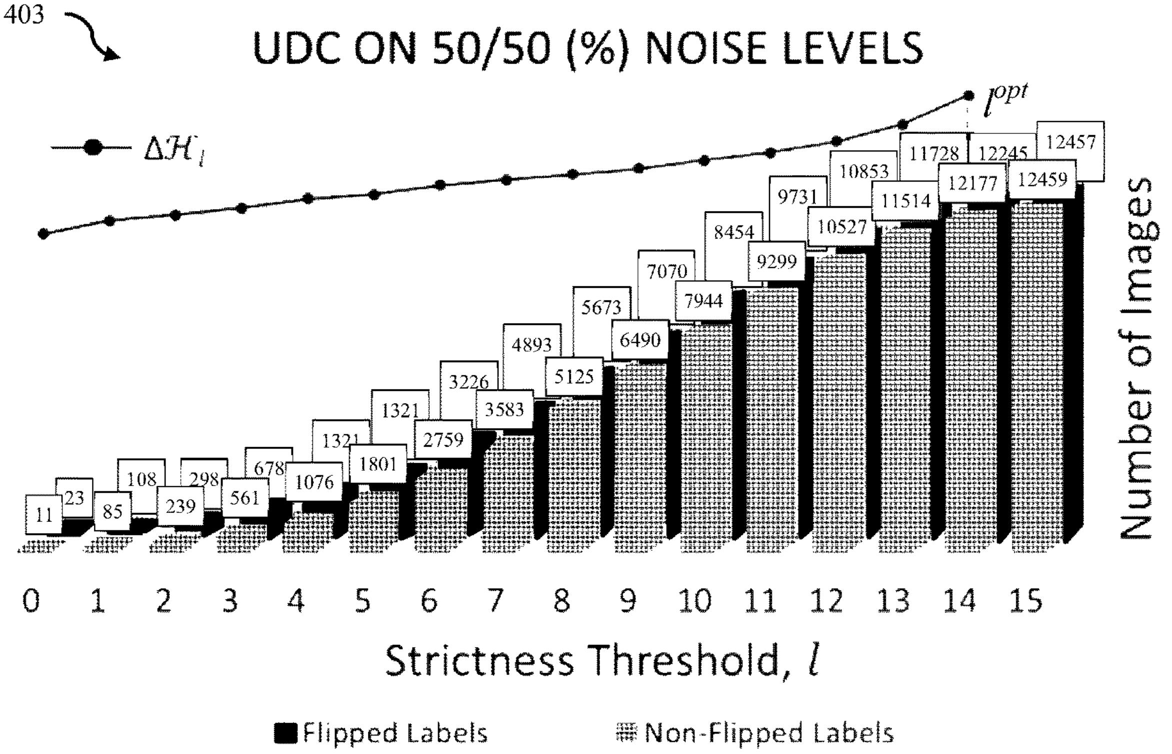
FIG. 4C is a plot of the cumulative histogram $\mathcal{H}_{l\ 1}$ at various strictness levels, l for uniform noise levels for the 50/50 case according to an embodiment.
Figure 4D:
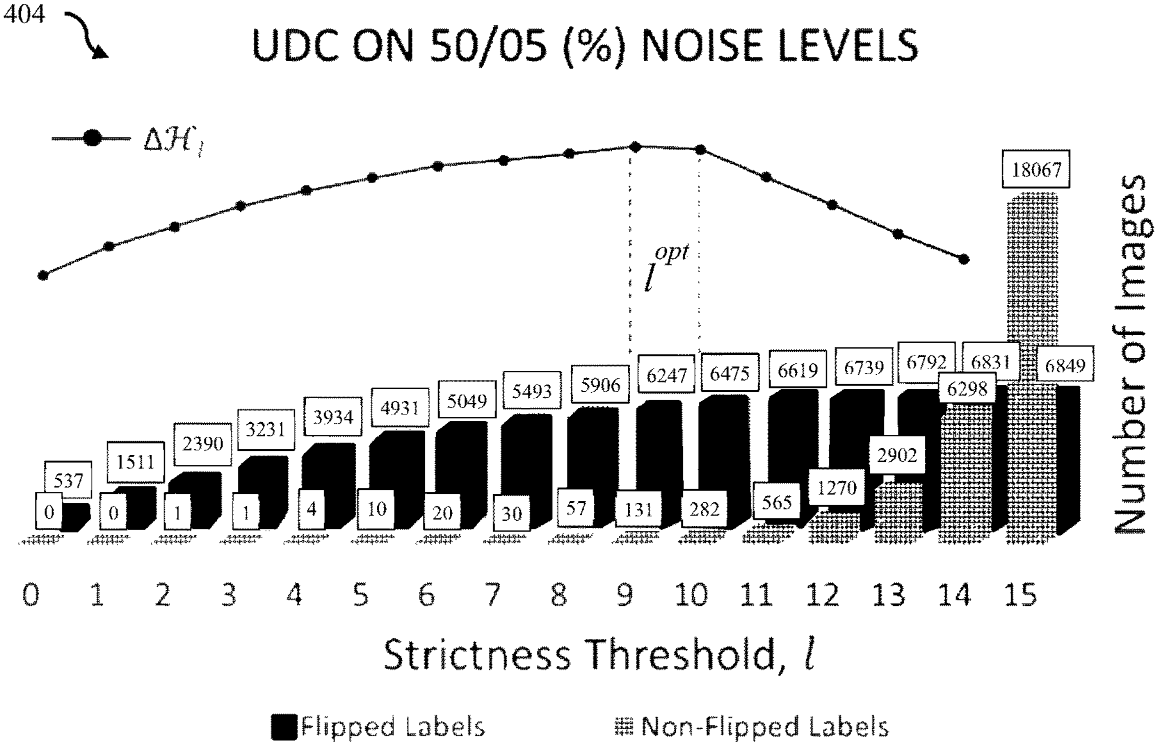
FIG. 4D is a plot of the cumulative histogram $\mathcal{H}_{l\ 1}$ at various strictness levels, l for asymmetric noise levels for the 50/05% case according to an embodiment.

Representative cumulative histograms produced using Algorithm 2 are shown in FIGS. 4A to 4D, with the results tabulated in Table 2, where flipped and non-flipped labels are shown explicitly. The cumulative histogram $\mathcal{H}_l$ at various strictness levels, l for uniform and asymmetric noise levels are shown in FIGS. 4A to 4D. FIG. 4A shows $\mathcal{H}_l$ for uniform noise levels for the 30/30 case, FIG. 4B shows $\mathcal{H}_l$ for asymmetric noise levels for the 35/05% case, FIG. 4C shows $\mathcal{H}_l$ for uniform noise levels for the 50/50 case and FIG. 4D show $\mathcal{H}_l$ for asymmetric noise levels for the 50/05% case according to an embodiment. Shown in columns filled with vertical lines and columns filled with hatched lines are noisy labels and correct labels, respectively, while the yellow line shows the percentage error (logarithmic scale and inverted to show maximization instead of minimization). The idea behind finding a good threshold is to maximize the number of flipped labels (rear vertical columns) while minimizing the number of non-flipped labels. The distribution of the non-flipped labels (front hatched columns) is similar between the two asymmetric cases, where a similar strictness threshold can be used, while for the (30,30) case, the distribution of non-flipped labels is wider, resulting in the lower strictness threshold chosen for this case. The diagram for the (50, 50) case shows clearly that the optimization of the threshold using the heuristic of Algorithm 3 is not possible, or at least unreliable or performs very poorly.

TABLE 2

Results from UDC applied to various noise levels.

| Experiment Set | | $n^{(0)}$ | $n^{(1)}$ | $n^{(2)}$ | $n^{(3)}$ | $n^{(4)}$ |
|---|---|---|---|---|---|---|
| Flip Levels (%, %) | | (0, 0) | (35, 5) | (50, 5) | (30, 30) | (70, 70) |
| Average Noise Level (%) | | 0 | 20 | 27.5 | 30 | 70 |
| Original Balanced Accuracy (%) | | 99.2 | 77.9 | 72.6 | 63.1 | 63.7 |
| Balanced Accuracy After UDC (%) | | — | 98.3 | 98.7 | 94.7 | 94.7 |
| Improvement After UDC (%) | | — | 20.4 | 26.1 | 31.6 | 31.0 |
| Images Removed UDC | Total Number | — | 4,699 | 6,757 | 7,578 | 7,442 |
| | Percentage (%) | — | 18.9 | 27.1 | 30.4 | 29.9 |

Table 2 shows the percentage improvement for several experimental cases after only a single round of application of the UDC method, with improvements greater than 20% achieved in all cases. Compared with the uniform noise cases $\{n^{(3)}, n^{(4)}\}$, the asymmetric noise cases $\{n^{(1)}, n^{(2)}\}$ achieve a higher balanced accuracy after one round of UDC. This is expected, since in the asymmetric cases, one class remains as a true Correct Class, allowing the UDC method to become more confident when identifying incorrectly labeled samples. Although the amount of improvement is higher in the uniform cases, this is because the asymmetric cases reach very high accuracies (>98%) after only one round of UDC, while in the uniform cases only 94.7% accuracy is achieved. This indicates that some amount of noise is left in the uniform case after one round of UDC. After one more round of UDC applied to the uniform cases, even better accuracy was achieved (99.7%) than the baseline accuracy (99.2%). This is suspected to happen because the UDC filters out "hard-to-identify" images, which may be incorrectly predicted by many models, helping to surpass the accuracy of the baseline. As seen in Table 2, the $n^{(4)}$=(70, 70) case is identical to the $n^{(3)}$=(30, 30) case, except the labels have been inverted by the model. For the $n^{(5)}$=(50, 50) case, the method simply learns to treat one entire class as incorrect and the other as correct, thereby throwing out all samples from the opposite noisy class. As such, and as might be expected, FIG. 4D shows that UDC fails when noise levels in both classes are 50%.

Case Study 2: Chest X-Rays

In this section, the UDC method is tested on a relatively "hard problem" of binary classification of pediatric chest x-rays. In the results to follow, the "Normal" class is the negative class with label 0 and "Pneumonia" class is the positive class with label 1. This dataset is split into a training set and a test set, which seem to have varying levels of noise. The results show that the UDC algorithms (Algorithms 1 to 3) can be used to identify and remove bad samples, and improve model performance (using both confidence and accuracy metrics) on a never-before-seen dataset suspected of having significant levels of (asymmetric) label noise.

Preprocessing

The dataset in this Case Study is manually filtered in the same way as in Case Study 1. No images were identified that were clear outliers, but several duplicates were found and deleted to avoid biased results. The size of the dataset after pre-processing is 5,856 images, with 5,232 and 624 images in the test.

Case Study 2A: Model Performance Enhancement on Blind Test Set

In this study label noise is not synthetically added to the dataset, instead the performance of trained models before and after UDC on a blind test set is compared. The metrics used to define performance are cross-entropy loss (CE) and balanced accuracy ($A_{bal}$).

Figure 5:
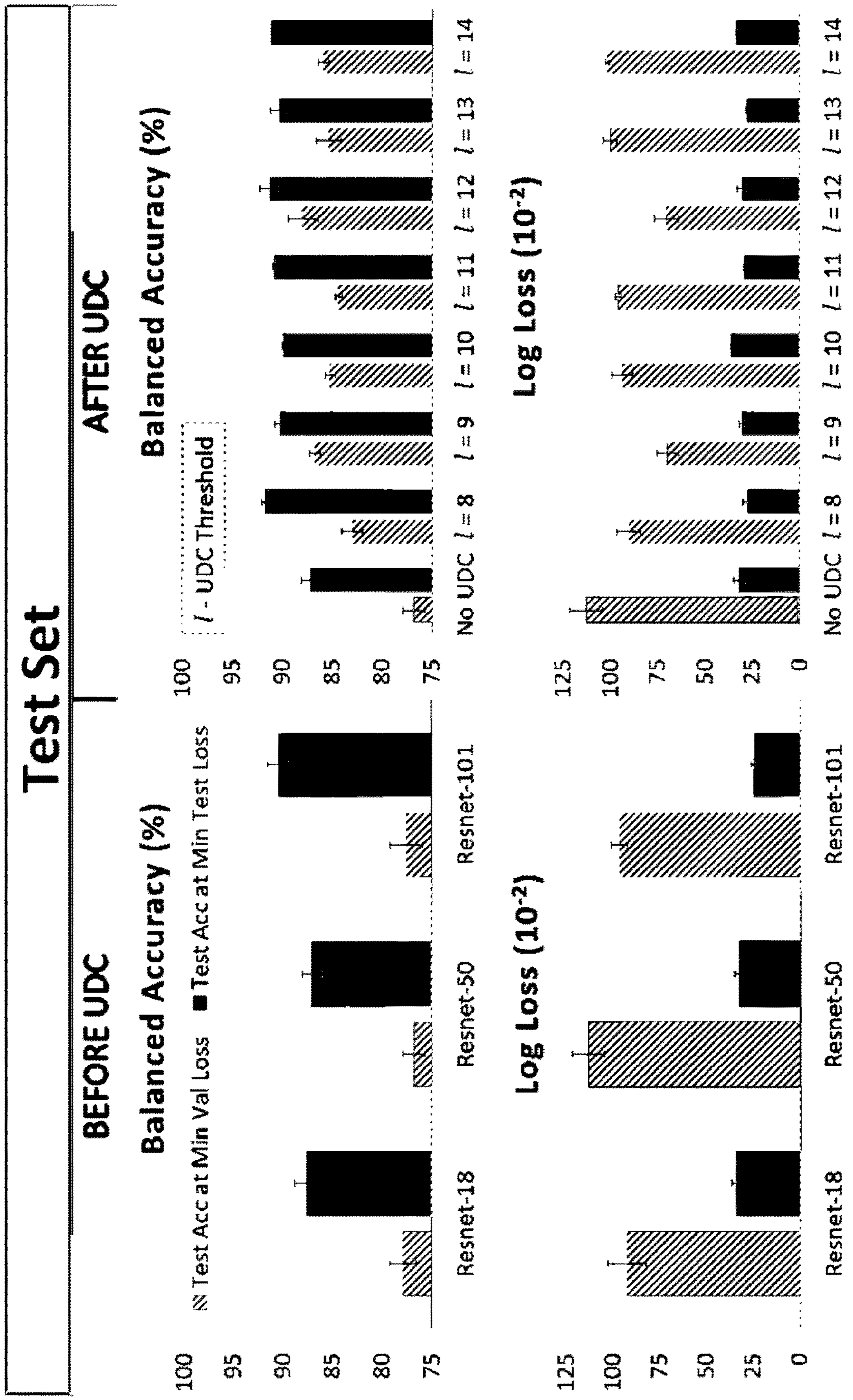
FIG. 5 is a set of histogram plots showing balanced accuracy (top) and cross-entropy, or log loss, (bottom) (left) for various model architectures before UDC and (right) for the ResNet-50 architecture after UDC for varying strictness thresholds I according to an embodiment.

FIG. 5 shows the balanced accuracy (top) and cross-entropy, or log loss, (bottom) (left) for various model architectures before UDC and (right) for the ResNet-50 architecture after UDC for varying strictness thresholds l for the test set. The shading of the bars represent the performance of the model on the test set if the epoch (or model) chosen is that which resulted in the lowest log loss as measured against (diagonal lines) the test set and (black) the validation ("val") set. The discrepancy between these two values is indicative of the generalizability of the model; i.e., models that perform well one but not the other are not expected to generalize well. This discrepancy is shown to improve with UDC.

Case Study 2B: Test Set Treated as Additional Data Source

Case Study 2A shows that UDC improves model performance even on a blind test set, which is a measure of the power of the UDC method. In this section, the effect of treating the test set as a different data source is investigated. To this end, the test set is included (or "injected") into the training set and the resulting effect on model performance is noted.

Figure 6:
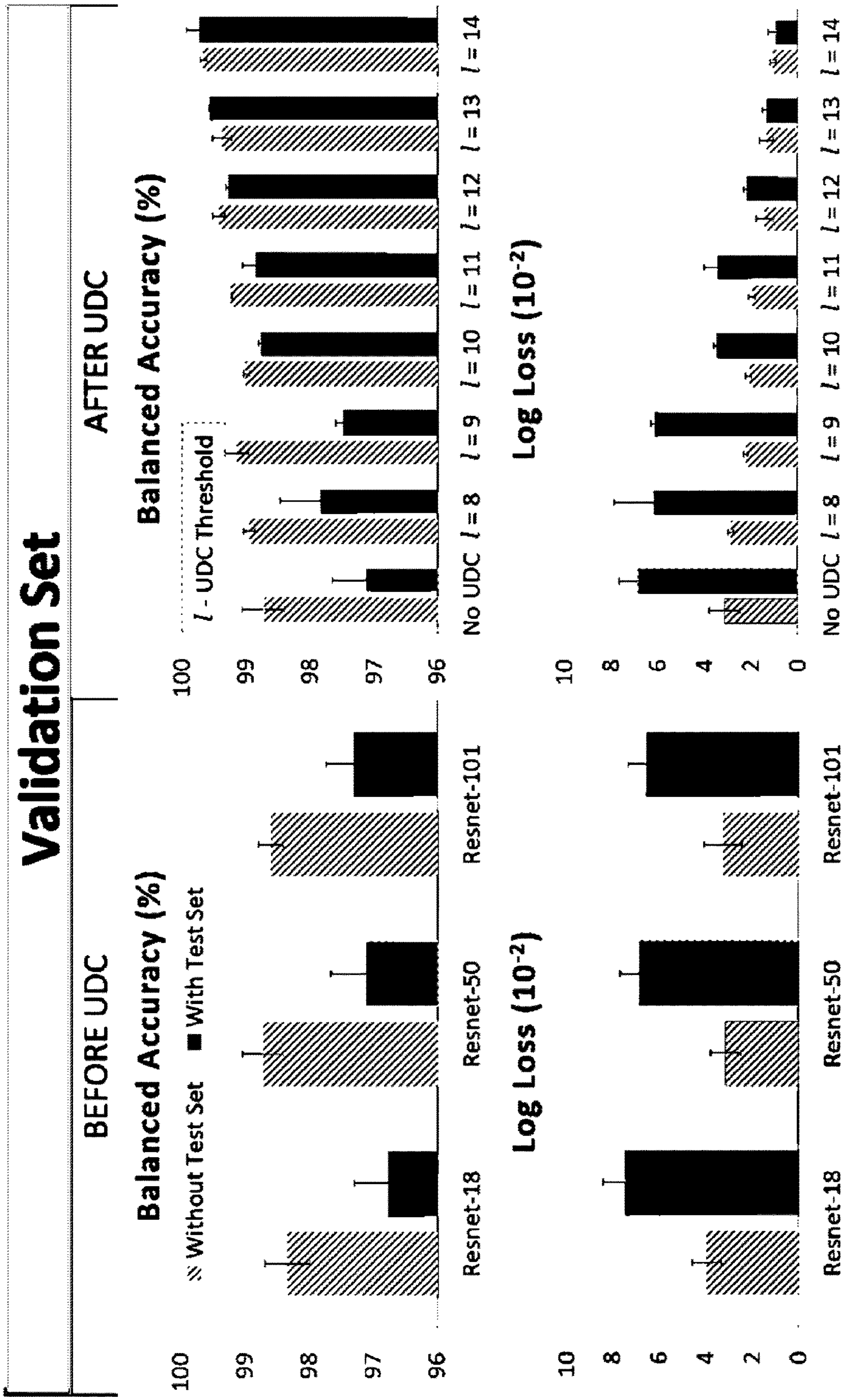
FIG. 6 is a set of histogram plots showing balanced accuracy (top) and cross-entropy, or log loss, (bottom) (left) for various model architectures before UDC and (right) after UDC for varying strictness thresholds l according to an embodiment.

FIG. 6 is a set of histogram plots showing balanced accuracy (top) and cross-entropy, or log loss, (bottom) (left) for various model architectures before UDC and (right) after UDC for varying strictness thresholds l for the validation set. The colour of the bars represent the performance of the model on the validation set, chosen as the epoch (or model) with minimum log loss on the validation set (diagonal lines) with and (black) without the test set included in the training set. The performance is seen to be drop considerably with the test set included, indicating that the level of label noise in the test set is severe.

Figure 7:
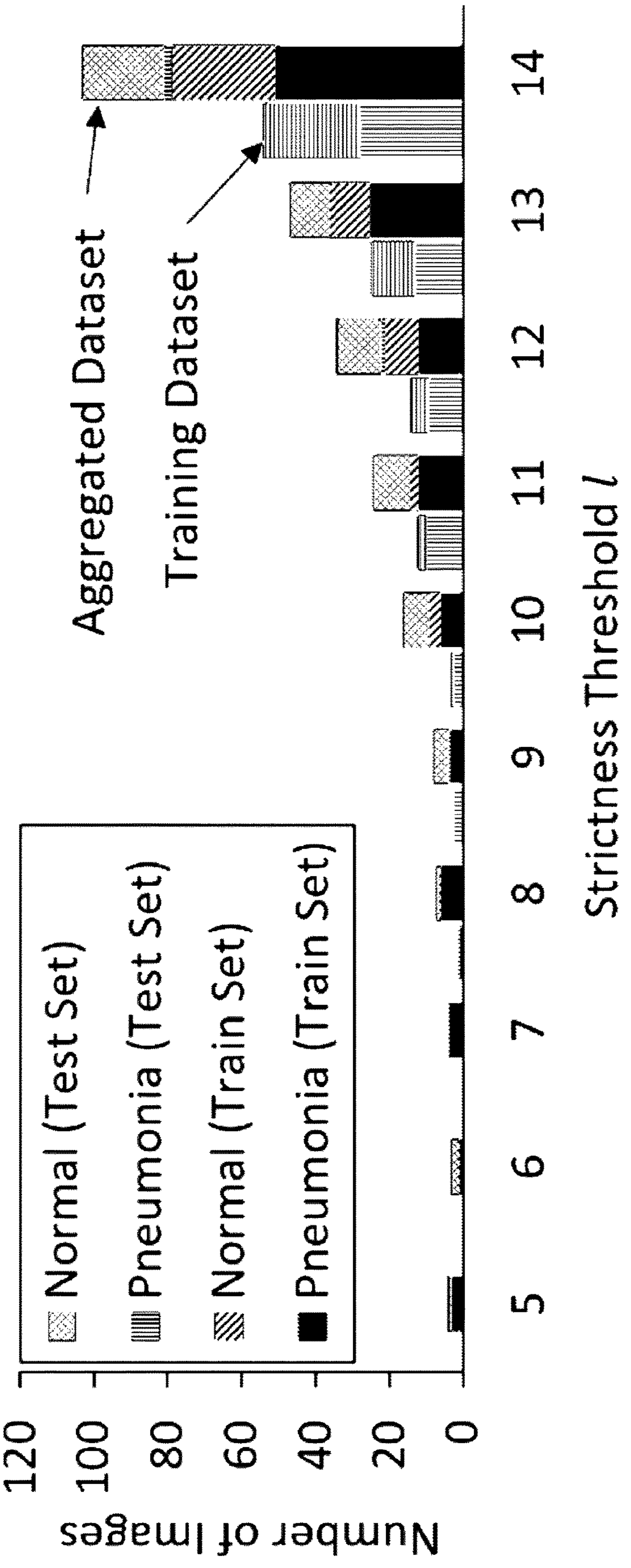
FIG. 7 is a histogram of the number of images per strictness threshold for test and train sets in normal and pneumonia labeled images according to an embodiment.

FIG. 7 is a histogram of the number of images per strictness threshold for test and train sets in normal and pneumonia labeled images according to an embodiment. FIG. 7 highlights two important effects of label noise in the set. 1) Though representing only 12% of the aggregated dataset, the test set increases the number of noisy labels identified by 100% when compared with the number for the training set alone, underlining the knock-on effect that label noise can have on model performance. 2) This shows how false negatives added to a training set "confuses" the model, causing a counter-intuitive increase in the number of false positives.

FIG. 6 shows the drastically reduced performance on the aggregated dataset compared with the training set. FIG. 7 betrays the suspected asymmetric label noise in the test set, where high label noise in the "Normal" class (in the test set) drives more errors in the opposite "Pneumonia" class (in the training set), similar to the phenomenon highlighted in FIGS. 1A and 3B.

Case Study 2C: Expert Radiologist Annotation of Clean Vs. Noisy Labels

A radiologist assessed 200 x-ray images, 100 that were identified by the UDC as Noisy, and 100 as "Clean" with the correct label. The radiologist was only provided the image, and not the image label nor the UDC label (Noisy or Clean). The images were assessed in random order, and the radiologist's assessment of the label and confidence (certainty) in the label for each image recorded.

Results show that the level of agreement between the radiologist's label and the original label was significantly higher with the Clean images compared with the Noisy images. Similarly, the radiologist's confidence with labels for Clean images was higher compared with the Noisy images. This demonstrates that for Noisy images, there may be insufficient information in the image alone to conclusively (or easily) make an assessment for pneumonia with certainty by either the radiologist or the AI.

Dataset and Methodology

A publicly available dataset of pediatric chest x-ray images (with associated Pneumonia/Normal labels) was obtained from Kaggle with 5,232 images in the training set and 624 images in the test set. In the AI training process, the training set is used to train or create the AI, and the test set is used as a separate dataset to test how well the AI performs on classifying new "unseen" dataset (i.e., data which was not used in the AI training process). The UDC method was applied on all 5,856 images in the dataset, and approximately 200 images were identified as Noisy.

The above results suggest that images identified by the UDC method to have Noisy labels are suspected to have inconsistencies that render their annotation (or labeling) more difficult. As such, we expect the level of agreement of Pneumonia/Normal assessments between different radiologists to be lower for images with Noisy labels than for those with Clean labels that are easily identified by the AI model and for which we expect a relatively high level of agreement between radiologists. The following two hypotheses are formulated and can be directly tested using the (Cohen's) kappa test:

$$H_0^{(1)}:$$

The level of agreement between radiologists for Noisy labels is different from random chance.

$$H_a^{(1)}:$$

The level of agreement between radiologists for Noisy labels is no different from random chance.

$$H_0^{(2)}:$$

The level of agreement between radiologists for Clean labels is no greater than random chance.

$$H_a^{(2)}:$$

The level of agreement between radiologists for Clean labels is greater than random chance.

We prepared an experimental dataset by splitting the data into Clean and Noisy labels as follows, where the two subsets are used in a clinical study to test the above hypotheses and validate the UDC method.

A dataset ($\mathbb{D}^S$) with 200 elements $z_j=(x_j, \hat{y}_j)$ has images $x_j$ and (noisy) annotated labels $\hat{y}_j$. This dataset is split into two equal subsets of 100 images each:

$(\mathbb{D}^S)_{clean}$—labels identified as Clean by UDC, with the following breakdown:
- 48 Normal
- 52 Pneumonia (39 Bacterial/13 Viral)

$(\mathbb{D}^S)_{noisy}$—labels identified as Noisy by UDC, with the following breakdown:
- 51 Normal
- 49 Pneumonia (14 Bacterial, 35 Viral)

The dataset $\mathbb{D}$ is randomized to create a new dataset $\hat{\mathbb{D}}$ given to an expert radiologist who is asked to label the images, and to indicate a level of confidence or certainty in those labels (Low, Medium and High). This randomization is done in order to address fatigue bias and any bias related to the ordering of the images.

The level of agreement between the expert radiologist and original labels is calculated using Cohen's kappa test and is compared between datasets $\mathbb{D}_{clean}$ vs. $\mathbb{D}_{noisy}$.

Results—Level of Agreement

Figure 8:
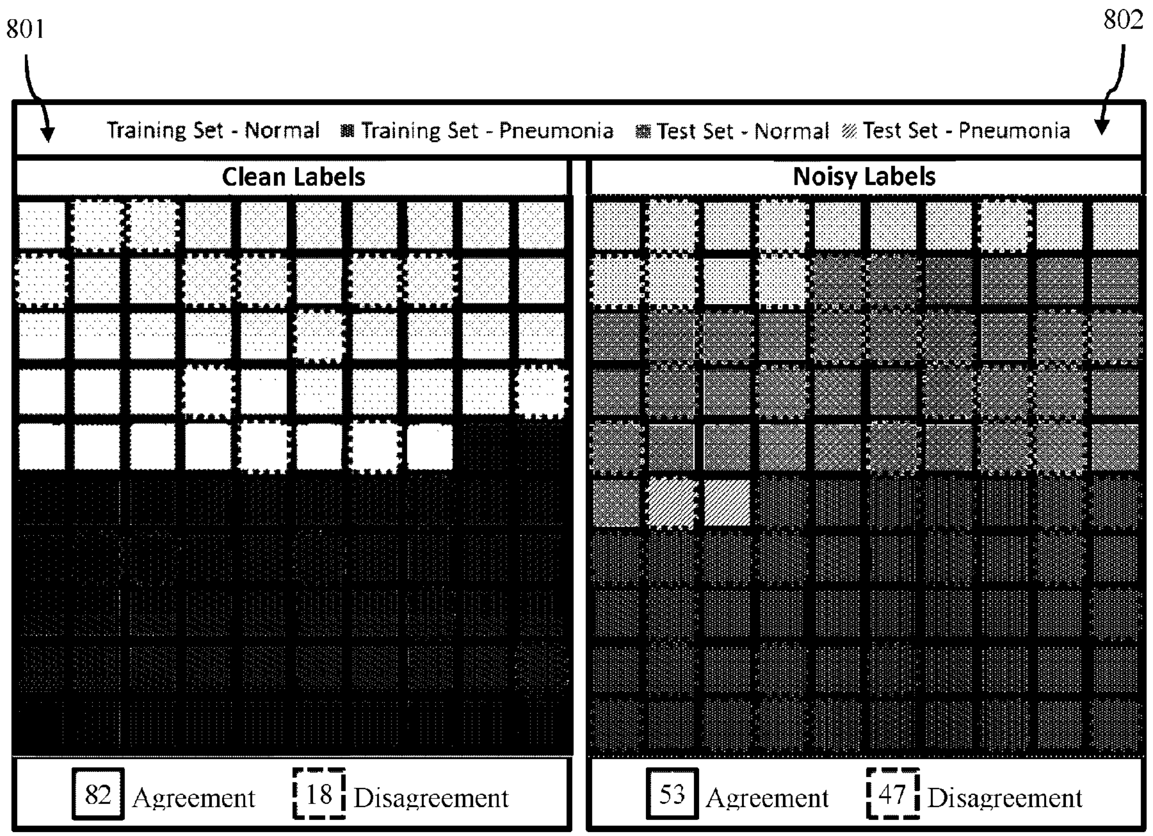
FIG. 8 is a plot of images divided into those with Clean labels and Noisy labels, and further subdivided into images sourced from the training set and test set and again into Normal and Pneumonia classes showing the agreement and disagreement for the clean labels and noisy labels according to an embodiment.

The results from the experiment are shown in FIG. 8 which is a plot of images divided into those with Clean labels and Noisy labels, and further subdivided into images sourced from the training set and test set and again into Normal and Pneumonia classes. Images are surrounded by solid and dashed lines for Agreements and Disagreements, respectively, between the original and expert radiologist's assessments. The prevalence of agreement is not significantly skewed between classes or dataset sources, suggesting label type (Clean vs. Noisy) is the most important factor of variation.

Figure 9:
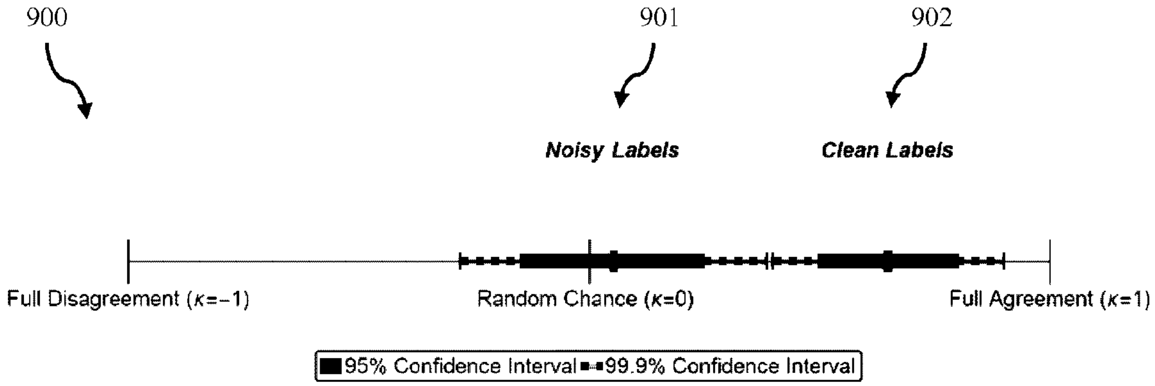
FIG. 9 is a plot of the calculation of Cohen's kappa for Noisy and Clean labels according to an embodiment.

Applying Cohen's kappa test on the results gives levels of agreement for Noisy ($\kappa\approx0.05$) and Clean ($\kappa\approx0.65$) labels. FIG. 9 is a plot of the calculation of Cohen's kappa for Noisy and Clean labels according to an embodiment and provides visual evidence showing that both null hypotheses, $$H_0^{(1)}$$

and $$H_0^{(2)},$$

are rejected with very high confidence (>99.9%) and effect size (>0.85). Therefore, both alternate hypotheses are accepted:

$$H_a^{(1)},$$

stating that labels identified as Noisy have levels of agreement no different from random chance, and $$H_a^{(2)},$$

stating that labels identified by the UDC as Clean have levels of agreement greater than random chance, and also significantly higher than those with Noisy labels.

Analysis—Level of Confidence

Regarding the results displayed above, it is interesting to look at yet another level of granularity: i.e., the level of confidence (Low, Medium, High) with which labels were assessed by the expert radiologist. These levels of confidence were judged from the notes given by the radiologist; assessments with comments that indicated severe radiographic issues or other confounding variables were labeled Low Confidence, assessments with comments such as "likely", "possible", "not excluded" were treated as Medium Confidence, and finally those assessments made with relative certainty were labeled High Confidence.

Figure 10:
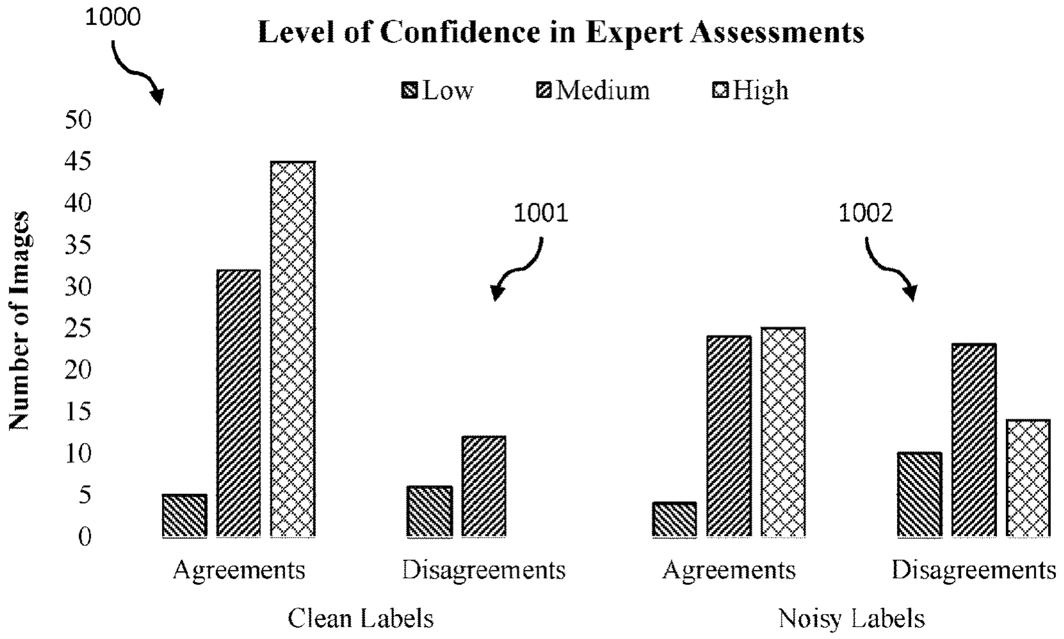
FIG. 10 is a histogram plot of the level of the agreement and disagreement for both clean label images and noisy label images according to an embodiment.

FIG. 10 is a histogram plot of the level of the agreement and disagreement for both clean label images and noisy label images according to an embodiment. FIG. 10 shows that all 18 disagreements for Clean labels were of either Low or Medium Confidence, suggesting yet again that Clean labels are indeed more easily or consistently classified and that both the UDC and the expert radiologist are confident that these labels, in general, are reflective of the ground truth. Also shown is that of the 47 disagreements for Noisy labels, 14 were of High Confidence, indicating that disagreements for Noisy labels are not only more frequent but also more assertive. FIG. 10 shows a breakdown of the level of confidence in the expert radiologist's assessments shows that for Clean labels, even for those few images where the radiologist disagreed with the label provided in the original dataset, the assessment was confounded by certain variables that reduced its confidence. This is in stark contrast with Noisy labels, for which both agreements and disagreements have similar distributions of assessment confidence.

It is important to state that chest x-rays can have many confounding variables, and it is very common for some x-rays to be rather uninformative for radiologists to make confident assessments. It is also important to put the number of Noisy labels in context. While for the sake of the study conducted here it was important to keep a balanced number of labels in both Pneumonia and Normal classes as well as in Clean and Noisy categories, there was over an order of magnitude more Clean labels (over 5,700) than Noisy ones (under 200), suggesting the dataset as a whole is, in large part and with the exception of Noisy labels, very likely to be self-consistent.

Finally, the type of pneumonia (bacterial, viral or other) was not investigated as this level of detail, and was not relevant and goes beyond the scope of the study. Significantly, this shows an embodiment of the UDC method is able to identify those image-label pairs that are likely to be difficult to assess and hence that may need more attention. This kind of method could be very useful as a screening tool for radiologists and could help radiology clinics with triaging and focusing more on suspicious (noisy) images than those likely to be easier to assess.

AI Performance Increase Using a UDC-Cleaned Dataset

Figure 11A:
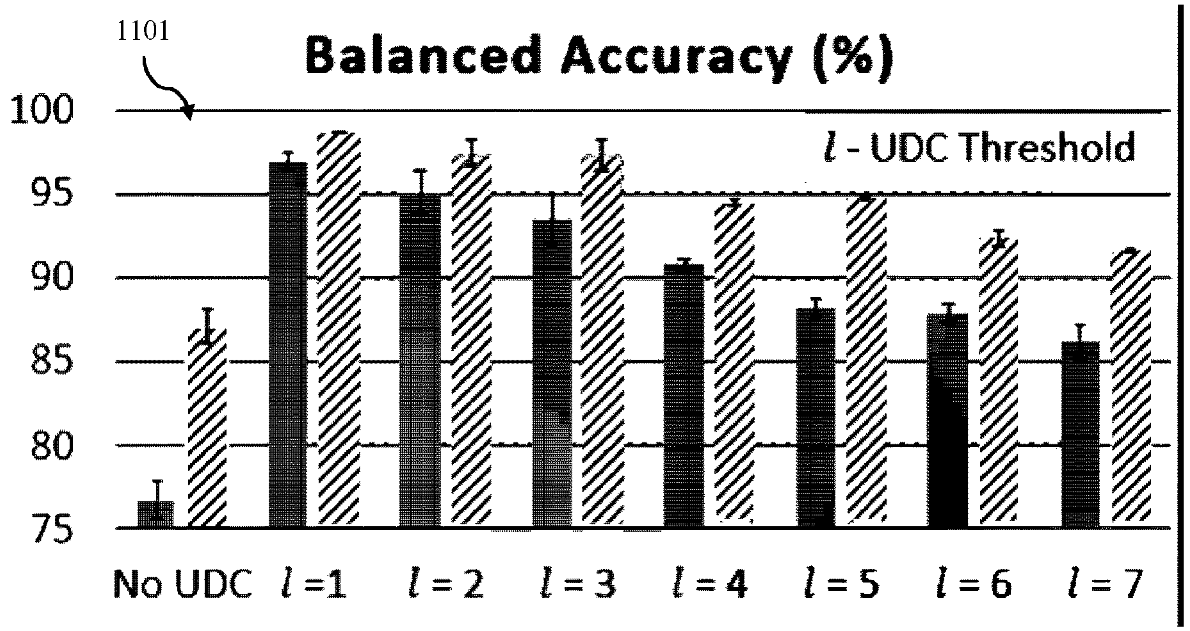
FIG. 11A is a histogram plot of balanced accuracy before and after UDC (cleaned data) for varying strictness thresholds I according to an embodiment.

In this study we compared the performance of the AI when trained using the original (un-clean) X-ray dataset (no UDC) versus the UDC-cleaned X-ray dataset (after UDC). The results are shown in FIG. 11A which is a histogram plot of balanced accuracy before and after UDC (cleaned data) for varying strictness thresholds 1 according to an embodiment. FIG. 11A shows that training the AI on a UDC cleaned dataset increases both the accuracy of the AI and the generalizability (and thus scalability and robustness) of the AI.

FIG. 11A shows two accuracy results on the test dataset. The bar filled with diagonal lines represents a theoretical maximum accuracy possible on the test dataset using AI. It is obtained by testing every trained AI model on the test dataset to find the maximum accuracy that can be achieved. The solid black bar on the other hand is the actual accuracy of the AI obtained using the standard practice of training and selecting an AI model. The standard practice involves training many AI models using the training dataset (using different architectures and parameters), and selecting the best AI based on the AI model's performance on a validation dataset. Only when the AI is selected is the final AI applied to the test dataset to assess the performance of the AI. This process ensures that the AI is not selected or "cherry-picked" to maximize the test dataset accuracy, and is representative of what will occur in practice when the AI will need to be blindly and independently applied to other unseen data. Additionally, the difference in accuracy between the diagonal line bars (theoretical maximum accuracy of the AI) and solid black bar (actual AI accuracy) is an indicator of the generalizability of the AI, i.e., the ability of the AI to reliability work on other unseen data (x-ray images).

A very important feature highlighted in FIG. 11A is the deviation between choosing an AI model during training that performs best on the test dataset (in diagonal line bars), which can be seen as "cherry-picking" the best result, compared with choosing a model that performs best on the validation set (in solid black bar), which is the method used in practice to choose a model which is expected to generalize better on new data. This shrinking of this deviation for varying levels of UDC applied to the training set shows not only that the overall accuracy is improved for the "best validation" AI model, but also that the UDC makes the AI training process more robust (i.e., generalizable and this scalable). This is evidence that a model trained on cleaned data can perform significantly better (>10%) on a blind dataset than one trained on an unclean dataset.

FIG. 11A also shows the accuracy given different UDC thresholds. Thresholds relate to how aggressive the UDC labels data as "bad" (Noisy or Dirty). A higher threshold results in more potentially bad data being removed from the dataset, and potentially a cleaner dataset. However, setting the threshold too high may result in clean data being incorrectly identified as bad data and removed from the clean dataset. Results in FIG. 11A show that increasing the UDC threshold from 8 to 9 increases the accuracy of the AI, indicating more bad data is being removed from the clean dataset used to train the AI. However, FIG. 11A shows diminishing returns as the threshold is increased further.

Dangers of Using an Un-Clean Test Dataset for Reporting AI Performance

The final part of this example is to use the UDC to investigate if the test dataset is clean, or if it comprises bad data. This is vital because the test dataset is used by AI practitioners to assess and report on the performance (e.g., accuracy) of the AI to be able to assess x-ray images for pneumonia. Too much bad data means that the AI accuracy result is not a true representation of the AI performance.

UDC results show that the level of bad data in the test dataset is significant. To validate this, we injected the test dataset into the training dataset used to train the AI to determine what is the maximum accuracy that could be obtained on the validation dataset.

Figure 11B:
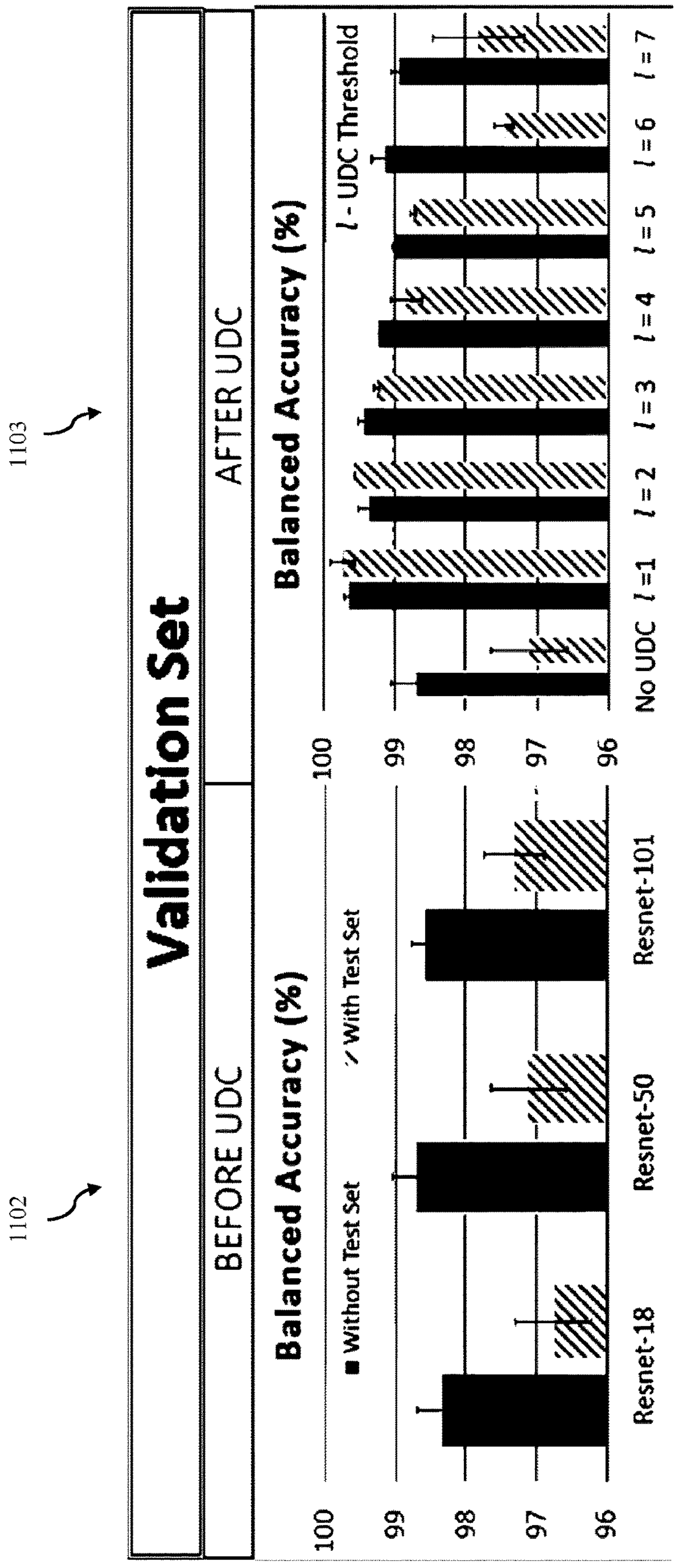
FIG. 11B is a set of histogram plots showing balanced accuracy (left) for various model architectures before UDC and (right) after UDC for varying strictness thresholds 1 according to an embodiment.

FIG. 11B is a set of histogram plots showing balanced accuracy (left) for various model architectures before UDC and (right) after UDC for varying strictness thresholds 1 according to an embodiment. The color of the bars represent the performance of the model on the validation set, (solid black bar) with and (diagonal lines) without the test set included in the training set. FIG. 11B shows the drastically reduced performance of AI trained using the aggregated dataset (training dataset plus the test dataset) compared with the AI trained only using the training set. This suggests that the level of bad data in the test dataset is significant. This also suggests an upper limit on the accuracy that even a good (generalizable) model can achieve. This is a critical point, since there is literature that reports high accuracy (~92%) on this chest x-ray dataset. Unless novel AI algorithms or AI targeting using medical domain knowledge was used, the high accuracy is likely a case of "cherry-picking" the best possible result, rather than training a generalizable model.

In other words, it is very difficult (or impossible) to get a model to perform well on both the validation (or training) and test datasets simultaneously using a standard AI training approach, without additional novel techniques to extract this information from the Noisy images. Our results show that with minimal bad data removal from the training, more generalizable performance on the test dataset reaches ~87% (refer FIG. 11A), and by removal of a few (<100) images from the test dataset, accuracies beyond 95% are achievable on a UDC cleaned test dataset.

Case Study 3: Embryos

In this case study, the UDC-M algorithm is tested on a "hard problem" which also includes data from multiple sources. Images of human embryos at Day 5 after IVF, imaged on an optical microscope, and matched labels of clinical pregnancy data, is vulnerable to label noise in a manner as described in FIG. 1A. Recall, that reasonable supporting evidence indicates that embryos that are measured as "non-viable", via an ultrasound scan 6 weeks after implantation (non-detection of fetal heart beat), are more likely to contain label noise e.g., due to patient factors as a major contributor, which is bad for training, compared to those that are measured as "viable" via ultrasound scan (detection of fetal heart beat).

Supporting evidence from a demographic cross-section of a dataset compiled across multiple clinic sources, can be obtained by examining the False Positive (FP) count of both embryologist ranking, and the results of a trained AI model on a blind or double-blind set.

The summary below shows a higher FP count naturally occurs in younger demographics, e.g., i) patients of age under 35 years, compared to ii) patients of all ages, and iii) patients of age equal to or over 35 years. The interpretation of this fact is that patients of younger age are more likely to require IVF due to a disease or patient factor compared to the case of poor embryo viability. The FP count of embryologist and AI have been shown in previous studies to be confident about viability, as shown by the cross-entropy loss from the model being high. This confidence in the embryos that are viable can be naturally explained by preponderance of noise in the non-viable class, e.g., due to patient factors.

i) Patients of age under 35 years
- 38.7% of all embryos are non-viable. For images with patient records available, 63.6% of patients had various patient factors reported in the clinical database.
- 78.5% of non-viable blind/double-blind embryos are predicted as False Positives by the trained AI.
- 83.7% of non-viable blind/double-blind embryos are predicted as False Positives by embryologists, showing consistency with the AI that the embryos appear viable, despite the contradictory label from the 6 week measurement of clinical pregnancy.

ii) Patients of all ages
- 42.2% of embryos are non-viable. For images with patient records, 57.4% of patients had various patient factors reported in the clinical database.
- 71.2% of non-viable blind/double-blind embryos are predicted as False Positives by the AI.
- 83.5% of non-viable blind/double-blind embryos are predicted as False Positives by embryologists, showing consistency with the AI that the embryos appear viable.

iii) Patients of age equal to or over 35 years
- 50.3% of embryos are non-viable. For images with patient records, 49.1% of patients had various patient factors reported in the clinical database.
- 58.6% of non-viable blind/double-blind embryos are predicted as False Positives by the AI.
- 83.0% of non-viable blind/double-blind embryos are predicted as False Positives by embryologists, showing consistency with the AI that the embryos appear viable.

These results indicate that there is a systematic increase in the reports of patient factors, using a rough proxy measurement of total False Positives as the patient age is reduced. This is a significant effect held for scores obtained from a trained AI model on a blind/double-blind set of multiple clinics, and also (to a lesser extent) for embryologists. This consistency of False Positives between the AI and embryologist, suggests that both the AI and the embryologists consistently viewed certain embryos as viable despite a non-viable label, and hence the non-viable embryos may actually be viable, and were recorded wrongly due to label noise. In order to confirm this evidence, a UDC-M algorithm is carried out on multiple datasets as follows.

Clinical Embryo Viability Data

There were 7 independent clinics as data owners who provided datasets. The data from each owner is called clinic-data while the combination of all data sources is denoted the aggregated dataset (or simply the dataset). Each clinic-data can be divided into training, validation and test sets for training and evaluation purposes, where the subdivided datasets are named uniquely so as to differentiate with the remaining sets. The aggregated dataset can be also divided into training, validation and testing sets for model training and evaluation purposes. In this case, one might call the aggregated data's training set, or simply call the training set.

For simplicity, the names of clinic-datasets are denoted as clinic-data 1, clinic-data 2 and so forth. Table 3 summarizes the class size and total size of 7 clinic-datasets, where it can be seen that class distributions vary significantly between datasets. In total, there are 3,987 images for model training and evaluation purposes.

TABLE 3

| Dataset description | | | |
|---|---|---|---|
| Sub-dataset | Class non-viable size | Class viable size | Total size |
| Clinic-data 1 | 106 | 180 | 286 |
| Clinic-data 2 | 335 | 317 | 652 |
| Clinic-data 3 | 129 | 202 | 331 |
| Clinic-data 4 | 191 | 218 | 409 |
| Clinic-data 5 | 491 | 475 | 966 |
| Clinic-data 6 | 780 | 337 | 1117 |
| Clinic-data 7 | 121 | 105 | 226 |
| Total | 2153 | 1834 | 3987 |

Case Study 3A: Predictive Power and Transferability Tests for A Single Clinic

In this study, we selected the largest clinic-data (most representative one) which is clinic-data 6 for the class-label randomization and transferability tests. The following steps were conducted:
- Randomly split the clinic-data 6 dataset into training, validation and testing sets.
- Randomly assign class label for all images in the training set while leaving the validation and testing sets untouched.
- Training deep learning models on the original training set of clinic-data 6 and explore the validation results and how the best validation results translate to the test results.
- Report the results in 4 different metrics: overall accuracy, balanced accuracy, class "non-viable" accuracy and class "viable" accuracy.

Table 4 presents the prediction results of the deep learning model being trained and evaluated on clinic-data 6 (trained either with random class label training set or the original training set of clinic-data 6). It should be noted that the clinic-data 6 has skewed class distribution in which the size of class "non-viable" is more than twice as large as that of class "viable". The first two rows of this table show the best validation results (the second row is regarded with the case of randomized training class labels) while the last two rows present the best test results. Some observations include:

If training image labels are randomized, the balanced accuracy on both validation and test datasets are around 53%, close to the 50% accuracy expected from a randomized dataset (i.e., 50:50 chance or coin toss of getting each sample in the dataset correct). However, the total accuracies are a bit higher which are about 60% for both validation and testing datasets. The rationale is because there are more images of class "non-viable" than in class "viable", and thus the model was trained better on images of the class "non-viable". Hence the class "non-viable" accuracy is much higher than class "viable" accuracy for both validation and testing sets, resulting in an overall higher accuracy. One can probably draw a point here that the prediction model is working properly, and the distribution of the training, validation and testing sets are similar.

The predictive capability of this clinic-data 6 is confirmed, with balanced accuracies are ~76% and ~70% for validation and testing sets, respectively. However, there is potential to improve the accuracy by cleansing the dataset and removing any mis-labeled or noisy data. The transferability tests are shown in Table 4 with two middle rows which are the corresponding test results translated from the best validation result (say, running the trained model, with the same epoch number, on both validation and test sets). The translated result on the test set (~68% in balanced accuracy) is similar to the best test result. This means that transferability is observable with this clinic-data. After Case Study 3A, one can confirm that the training model is in working order and the clinic-data is a candidate for further data cleansing using the Untrainable Data Cleansing technique. In the following Case Study 3B, we implement predictive power tests for the remaining clinics in the original dataset.

TABLE 4

The prediction results for clinic-data 6

| Data | Accuracy | Balanced accuracy | Class non-viable accuracy | Class viable accuracy |
|---|---|---|---|---|
| Best validation result | 75.000 | 75.590 | 73.223 | 77.957 |
| Best validation results with random train class labels | 59.821 | 53.724 | 74.495 | 32.954 |
| Test result (translated from the best validation result) | 68.005 | 68.126 | 67.912 | 68.341 |
| Test result (translated from the best validation result with random train class labels) | 62.500 | 51.591 | 76.384 | 26.799 |
| Best Test result | 69.494 | 70.167 | 68.758 | 71.576 |
| Best test result with random train class labels | 60.416 | 53.473 | 69.693 | 37.253 |

Case Study 3B: Predictive Power Tests for Remaining Clinics.

In this experiment, the predictive power test is repeated for each remaining clinic (clinic-data). For simplicity, each clinic-data is randomly divided into the training and validation set. There is no need to create a testing set because we are not performing the transferability test. The predictive power is represented via the balanced accuracy on the validation set. Several deep learning configurations are used to learn on each training set and tested separately on each test set. The evaluation metrics for reporting include overall accuracy, balanced accuracy, class "non-viable" accuracy and class "viable" accuracy, with balanced accuracy was considered as the most important (primary) metric to rank the predictive power of each dataset. In this case the class-based accuracy is used to sense check if the accuracy is balanced across different classes. However other metrics such confidence based metrics could have been used.

Table 5 presents the results to assess predictive power of 7 clinic-datasets. Clinic-data 3 and 4 have lowest predictive powers while the clinic-data 1 and 7 express the best self-prediction capability. As discussed in the previous section, accuracy close to 50% is considered having very low predictive power, which is likely due to high label noise in the dataset. These datasets are candidates for data cleansing. The individual predictive power report (Table 5) may indicate how much data should be removed from each clinic-data, i.e., the lower the predictive power the greater the number of mis-labeled data that may need to be removed from the dataset.

TABLE 5

Self-consistency testing results to assess predictive power

| Individual sub-data | Accuracy | Balanced accuracy | Class non-viable accuracy | Class viable accuracy |
|---|---|---|---|---|
| Clinic-data 1 | 72.605 | 70.328 | 62.975 | 77.682 |
| Clinic-data 2 | 57.930 | 57.306 | 54.543 | 60.070 |
| Clinic-data 3 | 55.783 | 54.732 | 50.628 | 58.836 |
| Clinic-data 4 | 54.878 | 55.365 | 57.294 | 53.436 |
| Clinic-data 5 | 61.840 | 61.783 | 56.715 | 66.852 |
| Clinic-data 6 | 68.005 | 68.126 | 67.912 | 68.341 |
| Clinic-data 7 | 70.869 | 70.686 | 67.666 | 73.706 |

Case Study 3C: UDC Applied on the Aggregated Dataset

In this experiment, all the clinic-datasets are combined and then randomly divided into training, validation and testing set. Different deep learning configurations were used to train on each training set. The following steps have been conducted: The best models were selected based on the both the accuracy of the viable class and the balanced accuracy on the validation dataset. Amongst multiple trained models using different configurations (various network architectures and hyper-parameter settings), the best 5 models were selected. However other metrics, such as confidence based metrics (e.g., Log Loss) could have been used.

The 5 selected models were run on the aggregated training set to produce 5 output files containing the per-images (or per-sample) accuracy results. The output consists of predicted score, predicted class label and the actual class label for every image in the training set.

Accumulate the 5 output files, and only include images from the Noisy Class (as these are the only images that are assumed to be potentially mis-labeled), to produce a single output file which contains for each (non-viable) image in the dataset: (1) the number of models that produce incorrect results (maximum of 5); and (2) the mean incorrect prediction score of these models. The mean prediction score indicates how far these models are getting wrong predictions.

A short list of images was created that included (non-viable) images that were misclassified by multiple models, say 4 or 5 models, with high incorrect prediction scores. These images are considered as the mis-labeled data and are candidates for removal or re-labeling.

The "mis-labeled" images in the list were removed from the aggregated training set in order to cleanse the dataset.

The following experiment was used to compare the validation and test results of models which were trained on the original training set and on the cleaned training set (removed list of mis-labeled images as described above). The metric used to assess the results was balanced accuracy, but other metrics, such as confidence based metrics (e.g., Log Loss) could have been used. In order to make the results more representative, multiple model types and hyper-parameter settings were used. There are multiple options for the deep learning architectures. Popular approaches include DenseNet, ResNet and Inception (-ResNet) net. In Table 6, we use several settings: setting 1 uses the same seed value, DenseNet-121 architecture and training set-based normalization approach, other hyper-parameters were changed for each model run; similarly, setting 2 uses the uniform normalization method instead of the training set-based normalization; and setting 3 fixes the network architecture as ResNet.

It can be seen from Table 6 that the cleaned training set shows an improvement in accuracy over the baseline which comprises the noisy data. In overall, a 1%-2% improvement was achieved for the validation and testing set, respectively. It should be noted that this is only preliminary results. Significant accuracy improvement could be expected if the failed images selection process is done meticulously.

TABLE 6

Remove images that multiple models consistently produce incorrect prediction

| Hyper-parameter settings | Data | Baseline | Remove images |
|---|---|---|---|
| Setting 1 | Validation set | 56.313 | 58.6022 |
| Setting 2 | Validation set | 55.845 | 58.602 |
| Setting 3 | Validation set | 62.073 | 62.903 |
| Average | | 58.077 | 60.0357 |
| Setting 1 | Testing set | 66.117 | 66.985 |
| Setting 2 | Testing set | 68.034 | 68.684 |
| Setting 3 | Testing set | 63.625 | 65.323 |
| Average | | 65.925 | 66.997 |

Case Study 3C: UDC Applied on Individual Clinic-Data's Training Set

In cases where data owners would want to keep their data private and secure, and not allow the data to be moved (leave their local storage system) and aggregated in a centralized location the Untrainable Data Cleansing Technique can be deployed locally on each individual data owner's dataset (i.e., on their local server). It should be noted that this approach can also be applied in cases where there is no data restriction or privacy issue.

In this experiment, clinic-datasets are processed individually. Each is randomly divided into training, validation and testing set. Different deep learning configurations were used and trained on each clinic's training datasets. The following was performed:

Multiple models were trained and the best models were selected for each clinic data using the accuracy results on the validation set. For this embryo prediction problem, the model that has high balanced accuracy and high misclassification rate on non-viable embryo images was selected. The reason is that we would want to capture as many noisy label images as possible from the non-viable class.

Run these models on their associated training dataset to produce the per-image result files that contain the predicted score, predicted class label and target.

Create a short list of images (only in the Noisy Class, i.e., the non-viable class) that were misclassified in each file. The predicted scores can be used for a thresholding filter purpose.

Remove these images from the training dataset and then aggregate all the datasets and re-train the best models on the new cleaned aggregated dataset.

TABLE 7

Compare the results on original testing set and the cleaned testing set when training models respectively on original training data and cleaned training data.

| Data | Accuracy | Balanced Accuracy | Class non-viable accuracy | Class viable accuracy |
|---|---|---|---|---|
| Original testing set | 63.912 | 61.524 | 51.930 | 71.118 |
| Cleaned testing set | 73.434 | 70.550 | 60.425 | 80.674 |

It can be seen from Table 7 that the improvement is significant across 4 different metrics when we train and test the model on the cleaned dataset.

The improvement in data quality and significance of using the Untrainable Data Cleansing technique can be observed in the training graphs of a single deep learning training run across multiple epochs.

Figure 12:
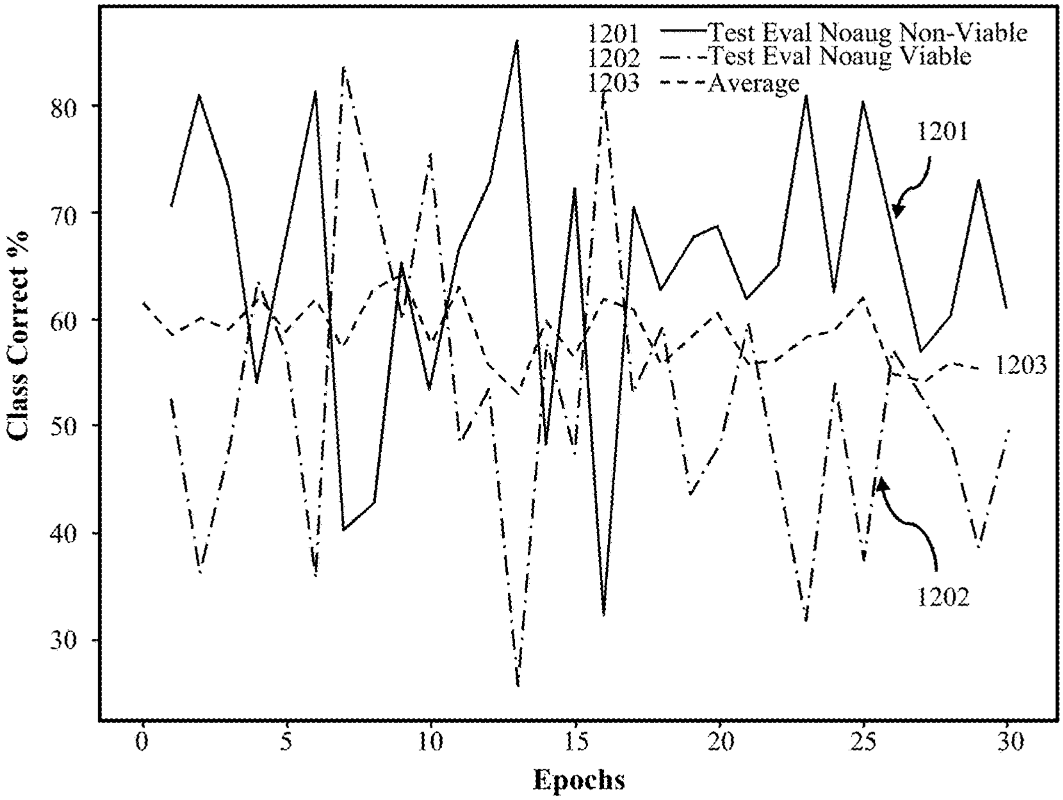
FIG. 12 is a plot of testing curves when an embodiment of an AI model is trained on uncleaned data, for non-viable and viable classes in dotted line and solid line respectively and the average curve of the two in dash line.
Figure 13:
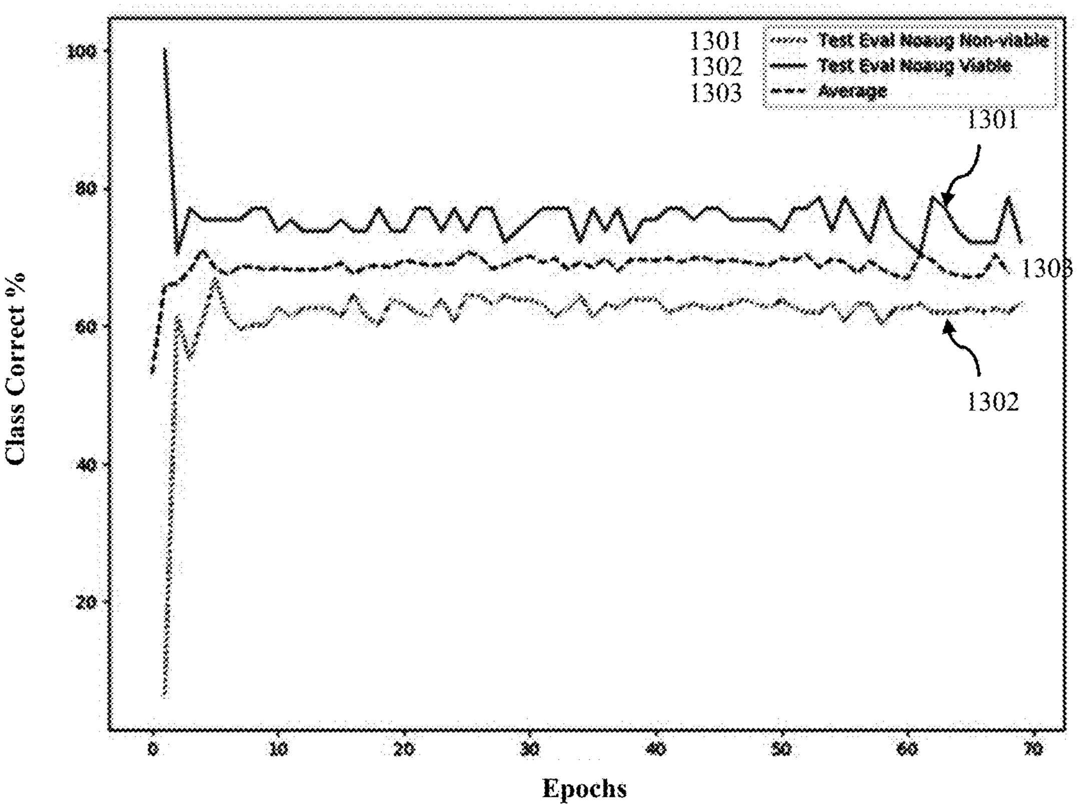
FIG. 13 is a plot of testing curves for an embodiment of an AI model when trained on cleaned data, for non-viable and viable classes in dotted line and solid line respectively and the average curve of the two in dash line.

FIG. 12 is a plot of testing curves when an embodiment of an AI model is trained on uncleaned data, for non-viable and viable classes in dotted line 1201 and solid line 1202 respectively and the average curve 1203 of the two in dash line. FIG. 13 is a plot of testing curves for an embodiment of an AI model when trained on cleaned data, for non-viable and viable classes in dotted line 1301 and solid 1302 respectively and the average curve 1303 of the two in dash line.

FIGS. 12 and 13 show the accuracy of the test dataset for non-viable and viable classes, and their average, for a single training run across multiple epochs for the original dataset and cleansed dataset, respectively. When we consider the training for the original dataset with the noisy (low quality) dataset (FIG. 12), it can be observed that the training is unstable and the class with the highest accuracy keeps switching between the viable and non-viable classes. This is observed in the strong 'sawtooth' pattern that occurs for the accuracy in both classes, from epoch to epoch. Note that even if the noise occurs predominantly in one class, in the case of a binary classification problem such as this case, difficulty in identifying correct examples in one class affects the model's ability to identify correct examples in the other class. As a result, there are a number of data points which cannot easily be classified, as their labels are in conflict with the majority of the other examples the model has been trained on. Minute changes to the model weights can thus have a large effect on these marginal examples.

Therefore, it is contended that with a noisy dataset (for the non-viable class) as the training progresses, the model switches between: (1) learning to correctly classify the "correctly labeled" viable class, resulting in the noisy and mis-labeled non-viable class dropping in accuracy; and (2) learning to correctly classify the mis-labeled non-viable class, resulting in the "correctly labeled" viable class dropping in accuracy. Given that the correct viable and mis-labeled non-viable images are actually from the same class, and thus will likely have the same classification patterns/characteristics, it is understandable that the training becomes unstable as the model decides to classify these images to either one of the classes-resulting in all the images in the alternative class becoming incorrect and switching the accuracy between the classes.

When we consider the training for the cleansed dataset (FIG. 13), it can be observed that the training is much more stable. In the binary classification case, the class that obtains the higher accuracy does not switch between the two classes from epoch to epoch, and the overall average accuracy (at each epoch, and across epochs) is higher. While there is still a certain number of noisy examples in the training, validation and test sets, which is difficult to remove with 100% certainty that the right images have been removed, the improved cleaned dataset begins to expose which class is the easier to classify, with the improved stability. In this case, the viable class now consistently obtains a higher accuracy, after a single cleansing pass has been performed, and therefore, the viable class is considered likely to be the cleaner class overall, and that further cleansing can be focused on the non-viable class.

This indicates that the Untrainable Data Cleansing technique has in fact removed the mid-labeled and noisy data from the dataset, ultimately improving the data quality and thus the AI model performance.

Case Study 4—UDL on Chest X-Rays

In further test the UDL algorithm described above we show here the results of an experimental design based on the chest X-ray dataset where the 200 images selected for expert annotation are considered further here. Using the same 200 images from the experimental results described above, we ignore their original labels to perform a multiple-label UDL algorithm as follows. The 200-image dataset is inserted into the larger (~5000 image) training set to form two separate datasets:

- one with random labels assigned to each image (e.g., "Normal" for a particular image), and
- another with each of these labels flipped (i.e., said image now labeled "Pneumonia").

Note: the remainder of the test set was ignored for this experiment, which would be expected to slightly affect outcomes compared with original UDC results.

Figure 14:
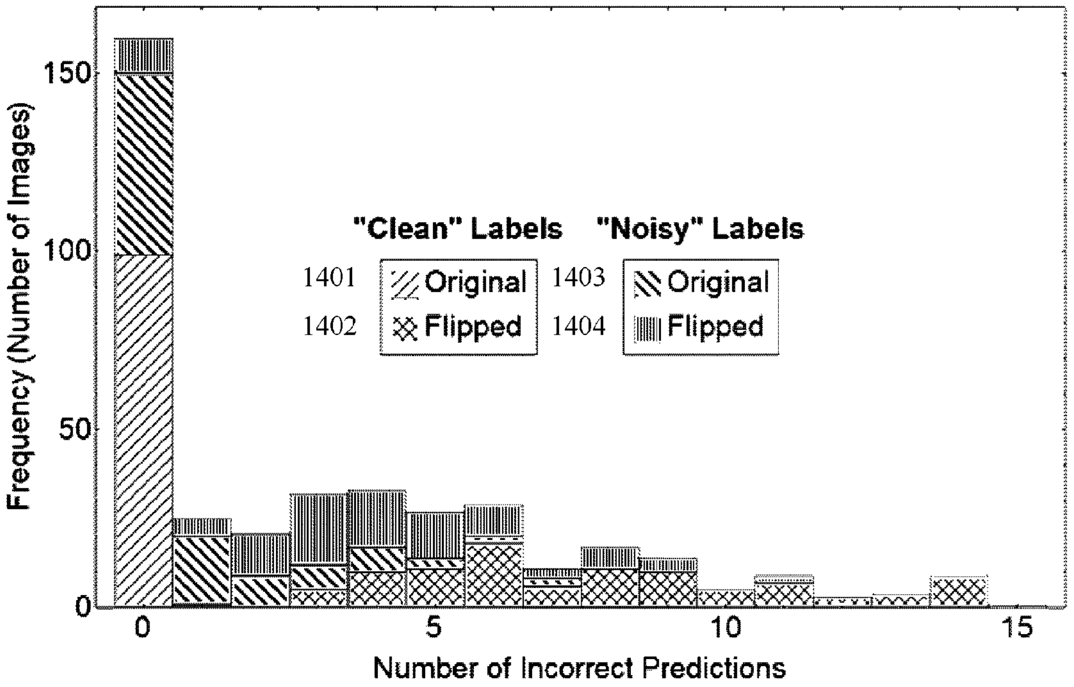
FIG. 14 is plot of the frequency vs the number of incorrect predictions when UDL according to an embodiment is applied to set of 200 chest x-ray images inserted into a larger training set of over 5000 images showing clean Labels are highly sensitive to their being labelled correctly, while Noisy Labels are less sensitive.

UDC was performed for both datasets, and the results are presented in FIG. 14 which shows a plot of the frequency vs the number of incorrect predictions:

Clean Labels:

- with correct (original) labels 1401 are correctly predicted by all AI models, while those
- with incorrect (flipped) labels 1402, are incorrectly predicted by a plurality of AI models (not a single Clean label with flipped label is ever correctly predicted by all models)

Noisy Labels:

- with correct (original) labels 1403, are only slightly more correctly predicted by a plurality of AI models than those
- with incorrect (flipped) labels 1404, which are only slightly less correctly predicted by a plurality of AI models.

While a rather significant fraction (50%) of Noisy labels are "correctly predicted" by all AI models with their original labels, this might not be so unexpected as the AI is trained to learn even from noisy data. The main takeaway is that the difference in number of incorrect predictions for Noisy images does not change much when their labels are flipped (an average difference of 2.7 for Noisy labels compared with 8.0 for Clean labels), which suggests that these images are only correctly predicted due to over-fitting, and that their original labels are not as certain as those images identified as having Clean labels. In addition, an analysis of the levels of agreement between even "correctly predicted" Noisy labels found no significant level of agreement with either the expert radiologist nor original annotations, with only 35 of 61 of these images in agreement with the original label and X of 61 in agreement with the expert radiologist. In conclusion, these results show that the UDL technique can be used to confidently label an unseen dataset and can also be useful to identify images with Noisy characteristics.

Various embodiments of UDC methods have been described. In particular the embodiments of the UDC method have been shown to address mis-classified or noisy data in a sub-set of classes or all classes of datasets. In the UDC method we use an approach based on k-fold cross validation in which we a divide a dataset into a multiple training subsets (i.e., k folds), and then for each of the subsets (k folds) train a plurality of AI models with different model architectures (e.g., to generate n×k AI models). The estimated labels can be compared to the known labels, and samples which are consistently incorrectly predicted by the AI models are then identified as bad data (or bad labels) and these samples can then be relabeled or excluded. In the case of medical data which is excluded (for example because the quality of the information is poor) this can be flagged for detailed analysis by an expert, including possibly recollecting the data (e.g., taking another X-ray). Embodiments of the method can be used on a datasets from single sources or multiple sources, and for binary classification, multi-class classification as well as regression and object detection problems. The method can thus be used in healthcare data, and in particular healthcare datasets comprising images captured from a wide range of devices such as microscopes, cameras, X-ray, MRI, etc. However it will be understood that the methods can also be used outside of the healthcare environment.

Further the UDL method extends the UDC approach to perform training-based approach to inferencing to enable inference of an unknown label for previously unseen data. Rather than training an AI model, the AI training process itself is used to determine the classification of previously unseen data. In these embodiments multiple copies of unlabeled data are formed (one for each of the total number of classes) and each sample in assigned a temporary label. These temporary labels, which can be either random or based on a trained AI model (as per the standard AI model-based inferencing approach). This new data is then inserted into a set of (clean) training data and the UDC technique is used up to a total of C times to determine which, if any, of the temporary labels is confidently correct (not mis-labeled) or confidently incorrect (was mis-labeled). Ultimately, if the actual label for a new image is knowable (the data in the image is not so noisy as to contain no discernible features), the UDC can be used to reliably determine (or predict/inference) this label or classification. By inserting the unseen data into the training data, the training process itself tries to find specific patterns, correlations and/or statistical distributions in the unseen data in relation to the (clean) training data. The process is thus more targeted and personalized to the unseen data, because the specific unseen data is analyzed and correlated within the context of other data with known outcomes as part of the training process, and the repeated training-based UDC process itself will eventually determine the most likely label for the specific data—potentially boosting both accuracy and generalizability.

A series of case studies applying the UDC method were also shown. The first case study was an easy case study in which an AI was trained to identify cats and dogs, and bad data was intentionally "injected" into the dataset by randomly flipping the labels of a certain proportion of the images. This study found that images with flipped (incorrect) labels were easily identified as incorrectly labeled dates (dirty labels). For this problem there were relatively few cases of noisy labels in which images are of low quality and indistinguishable, for, say, images of dogs with cat-like features, or where an image of a cat is not in-focus or high enough resolution to be recognizable as a cat, or where only non-specific portions of a cat are visible in an image.

The second case study was a harder classification problem of identifying pneumonia from chest x-rays (second case study), which is more susceptible to subtle and hidden confounding variables. In this study UDC was able to identify bad data, we further found that the dominant source of bad data was Noisy labels, where the images themselves and alone do not comprise sufficient information to identify the labels with certainty. This means that the images have a greater chance of being mis-labeled, and in extreme cases, the image does not contain sufficient information for any assessment (AI or human) to be able determine a label at all.

The results were verified using an expert radiologist. The radiologist assessed 200 x-ray images, 100 that were identified by the UDC as Noisy, and 100 as "Clean" with the correct label. The radiologist was only provided the image, and not the image label nor the UDC label (Noisy or Clean). The images were assessed in random order, and the radiologist's assessment of the label and confidence (certainty) in the label for each image recorded. Results show that the level of agreement between the radiologist's label and the original label was significantly higher for the Clean images compared with the Noisy images. Similarly, the radiologist's confidence with labels for Clean images was higher compared with the Noisy images. This demonstrates that for Noisy images, there is insufficient information in the image alone to conclusively (or easily) make an assessment for pneumonia with certainty by either the radiologist or the AI.

It was further shown that when the Noisy labels are removed from the dataset to create a "Clean" dataset for AI training, the performance of the AI for detecting pneumonia improves in accuracy and generalizability. This suggests that training AI using Noisy data, which either does not contain enough information to classify (label) the data or have a greater chance for being mis-labeled, can confuse the AI and result in the AI learning the wrong features that relate to a pneumonia or normal x-ray. This highlights the challenges in the AI healthcare industry where datasets are being used that are assumed to be perfect or clean, and are not due to a range of factors including bad quality data, or incorrect labels as a result of subjectivity, uncertainty, human error, or intentional (adversarial) attacks. Medical datasets that contain Dirty or Noisy labels can negatively impact on both the accuracy and scalability (generalizability) of the AI, and ultimately the clinic or patient that may depend on a reliable AI assessment. Thus by using embodiments of UDC, datasets can be cleaned and noisy data can be excluded to improve the performance of AI models.

It was also shown that embodiments of the UDC method identified a high level of Noise in the test dataset of x-ray images. A test dataset is a separate blind "unseen" dataset that is not used in the AI training process for which the performance of the final trained AI is tested. The test dataset is used by AI practitioners to report the accuracy of their AI for detecting pneumonia from x-ray images. Noise in the test dataset means that the reported accuracy of the AI for this dataset may not be a true representation of the AI's accuracy. Some research groups have reported a very high level of accuracy for their AI on this dataset. It is thus an open question as to whether their AI is actually able to extract the right information from the Noisy images to better label them (which may be possible using novel AI algorithms or targeting the AI by incorporating additional medical domain knowledge), or whether the higher accuracy was a result of luck or "cherry-picking" AI that was able to achieve better accuracy result for this specific dataset. Regardless, accuracy results using an un-clean test dataset has the potential to mis-lead researchers or clinicians on the true performance and reliability of the AI, with potentially real-world consequences for clinicians and patients that may rely on the AI if it is ever used in practice.

The above case studies demonstrated that embodiments of the UDC method can be used to effectively identify bad data (or bad labels) even for "hard" classification problems such as detection of pneumonia from pediatric x-rays. The removal of the bad data was used to create a clean training dataset for AI training and resulted in an improvement in the AI performance for identifying pneumonia in x-rays. Additionally, UDC found bad data present in the test dataset used by AI practitioners to test and report on their AI performance for analyzing x-ray images for pneumonia. This means that the AI performance that is reported may not be the true performance of the AI, and potentially (unintentionally) misleading. Lastly, bad data that was identified by UDC for this particular problem was of the Noisy category, which both the AI and radiologist found difficult to label with confidence using the available x-ray image. This suggests that these images alone contain limited information to make a conclusive diagnosis with certainty, and thus have a higher probability of being mis-labeled or mis-diagnosed.

Finally the third case study showed the application of the UDC method on a hard problem, namely estimation of embryo viability for IVF, which included data from multiple sources (multiple clinics). The UDC method was able to identify and remove the mid-labeled and noisy data from the dataset, ultimately improving the data quality and thus the AI model performance.

The results in this specification demonstrate that embodiments of the UDC method have the potential to have a profound impact on the industrial use of AI for hard problems, such as in AI healthcare. Medical data is often inherently "unclean", and embodiments of the UDC method can be used to effectively clean and used to train AI that is of higher performance, and in turn, ensure accurate, scalable (generalizable) and enabling more reliable use for clinicians and patients around the world.

Further embodiments of UDC also has a further benefit of being able to analyze medical data and identify which images are likely to be Noisy (i.e., difficult to assess with certainty), to the extent that it could be used as a potential triage tool to direct clinicians to those cases that warrant additional in-depth clinical assessment.

Embodiments of the UDC method can be used to help clean reference test datasets, which are datasets that are used by AI practitioners to test and report on the efficacy of their AI. Testing and reporting on an unclean dataset can be misleading as to the true efficacy of the AI. A clean dataset following UDC treatment enables a true and realistic representation and reporting of the accuracy, scalability and reliability of the AI, and protect clinicians or patients that may need to rely on it.

Those of skill in the art would understand that information and signals may be represented using any of a variety of technologies and techniques. For example, data, instructions, commands, information, signals, bits, symbols, and chips may be referenced throughout the above description may be represented by voltages, currents, electromagnetic waves, magnetic fields or particles, optical fields or particles, or any combination thereof.

Those of skill in the art would further appreciate that the various illustrative logical blocks, modules, circuits, and algorithm steps described in connection with the embodiments disclosed herein may be implemented as electronic hardware, computer software or instructions, middleware, platforms, or combinations of both. To clearly illustrate this interchangeability of hardware and software, various illustrative components, blocks, modules, circuits, and steps have been described above generally in terms of their functionality. Whether such functionality is implemented as hardware or software depends upon the particular application and design constraints imposed on the overall system. Skilled artisans may implement the described functionality in varying ways for each particular application, but such implementation decisions should not be interpreted as causing a departure from the scope of the present invention.

The steps of a method or algorithm described in connection with the embodiments disclosed herein may be embodied directly in hardware, in a software module executed by a processor, or in a combination of the two, including cloud based systems. For a hardware implementation, processing may be implemented within one or more application specific integrated circuits (ASICs), digital signal processors (DSPs), digital signal processing devices (DSPDs), programmable logic devices (PLDs), field programmable gate arrays (FPGAs), processors, controllers, micro-controllers, microprocessors, or other electronic units designed to perform the functions described herein, or a combination thereof. Various middleware and computing platforms may be used.

In some embodiments the processor module comprises one or more Central Processing Units (CPUs) or Graphical processing units (GPU) configured to perform some of the steps of the methods. Similarly a computing apparatus may comprise one or more CPUs and/or GPUs. A CPU may comprise an Input/Output Interface, an Arithmetic and Logic Unit (ALU) and a Control Unit and Program Counter element which is in communication with input and output devices through the Input/Output Interface. The Input/Output Interface may comprise a network interface and/or communications module for communicating with an equivalent communications module in another device using a predefined communications protocol (e.g., Bluetooth, Zigbee, IEEE 802.15, IEEE 802.11, TCP/IP, UDP, etc.). The computing apparatus may comprise a single CPU (core) or multiple CPU's (multiple core), or multiple processors. The computing apparatus is typically a cloud based computing apparatus using GPU clusters, but may be a parallel processor, a vector processor, or be a distributed computing device. Memory is operatively coupled to the processor(s) and may comprise RAM and ROM components, and may be provided within or external to the device or processor module. The memory may be used to store an operating system and additional software modules or instructions. The processor (s) may be configured to load and executed the software modules or instructions stored in the memory.

Software modules, also known as computer programs, computer codes, or instructions, may contain a number a number of source code or object code segments or instructions, and may reside in any computer readable medium such as a RAM memory, flash memory, ROM memory, EPROM memory, registers, hard disk, a removable disk, a CD-ROM, a DVD-ROM, a Blu-ray disc, or any other form of computer readable medium. In some aspects the computer-readable media may comprise non-transitory computer-readable media (e.g., tangible media). In addition, for other aspects computer-readable media may comprise transitory computer-readable media (e.g., a signal). Combinations of the above should also be included within the scope of computer-readable media. In another aspect, the computer readable medium may be integral to the processor. The processor and the computer readable medium may reside in an ASIC or related device. The software codes may be stored in a memory unit and the processor may be configured to execute them. The memory unit may be implemented within the processor or external to the processor, in which case it can be communicatively coupled to the processor via various means as is known in the art.

Further, it should be appreciated that modules and/or other appropriate means for performing the methods and techniques described herein can be downloaded and/or otherwise obtained by computing device. For example, such a device can be coupled to a server to facilitate the transfer of means for performing the methods described herein. Alternatively, various methods described herein can be provided via storage means (e.g., RAM, ROM, a physical storage medium such as a compact disc (CD) or floppy disk, etc.), such that a computing device can obtain the various methods upon coupling or providing the storage means to the device. Moreover, any other suitable technique for providing the methods and techniques described herein to a device can be utilized.

The methods disclosed herein comprise one or more steps or actions for achieving the described method. The method steps and/or actions may be interchanged with one another without departing from the scope of the claims. In other words, unless a specific order of steps or actions is specified, the order and/or use of specific steps and/or actions may be modified without departing from the scope of the claims.

Throughout the specification and the claims that follow, unless the context requires otherwise, the words "comprise" and "include" and variations such as "comprising" and "including" will be understood to imply the inclusion of a stated integer or group of integers, but not the exclusion of any other integer or group of integers.

The reference to any prior art in this specification is not, and should not be taken as, an acknowledgement of any form of suggestion that such prior art forms part of the common general knowledge.

It will be appreciated by those skilled in the art that the disclosure is not restricted in its use to the particular application or applications described. Neither is the present disclosure restricted in its preferred embodiment with regard to the particular elements and/or features described or depicted herein. It will be appreciated that the disclosure is not limited to the embodiment or embodiments disclosed, but is capable of numerous rearrangements, modifications and substitutions. In general, in the following claims, the terms used should not be construed to limit the claims to the specific embodiments disclosed in the specification and the claims, but should be construed to include all possible embodiments along with the full scope of equivalents to which such claims are entitled.

The invention claimed is:

1. A computation method for cleaning a plurality of training datasets for generating an Artificial Intelligence (AI) model, the method comprising:

testing each training dataset in a plurality of training datasets for positive predictive power and generating a cleansed training dataset if the positive predictive power is within a predefined range, wherein estimating the positive predictive power comprises:

dividing a training dataset into a plurality of validation subsets;

training, for each validation subset, a plurality of Artificial Intelligence (AI) models on two or more of the remaining (k−1) validation subsets;

obtaining a first count of the number of times each sample in the validation dataset is either correctly predicted, incorrectly predicted, or passes a threshold confidence level, by the plurality of trained AI models;

randomly assigning a label or outcome to each sample;

training, for each validation subset, a plurality of Artificial Intelligence (AI) models on two or more of the remaining (k−1) validation subsets;

obtaining a second count of the number of times each sample in the validation dataset is either correctly predicted, incorrectly predicted, or passes a threshold confidence level, by the plurality of trained AI models when random assigned labels are used;

estimating the positive predictive power by comparing the first count and the second count; and generating the cleansed training dataset if the positive predictive power is within a predefined range wherein generating the cleansed training data set comprises:

dividing a training dataset into a plurality (k) of training subsets;

training, for each training subset, a plurality (n) of Artificial Intelligence (AI) models on two or more of the remaining (k−1) training subsets and using the plurality of trained AI models to obtain an estimated label for each sample in the training subset for each trained AI model; and removing or relabeling samples in each training subset which are consistently incorrectly predicted by the plurality of trained AI models;

generating an aggregated dataset using the plurality of cleansed datasets;

cleaning the aggregated dataset to generate a cleansed aggregated training dataset comprising:

dividing the aggregated dataset into a plurality (k) of training subsets;

training, for each training subset, a plurality (n) of Artificial Intelligence (AI) models on two or more of the remaining (k−1) training subsets and using the plurality of trained AI models to obtain an estimated label for each sample in the training subset for each trained AI model;

removing or relabeling samples in each training subset which are consistently incorrectly predicted by the plurality of trained AI models;

generating a final AI model by training one or more AI models using the cleansed aggregated training dataset; and deploying the final AI model.

2. The method as claimed in claim 1, wherein the plurality of Artificial Intelligence (AI) models comprises a plurality of model architectures.

3. The method as claimed in claim 1, wherein training, for each training subset, a plurality of Artificial Intelligence (AI) models on two or more of the remaining (k−1) training subsets comprises:

training, for each training subset, a plurality of Artificial Intelligence (AI) models on all of the remaining (k−1) training subsets.

4. The method as claimed in claim 1, wherein removing or relabeling samples in each training subset comprises:

obtaining a count of the number of times each sample in each training subset is either correctly predicted, incorrectly predicted or passes a threshold confidence level, by the plurality of trained AI models;

removing or relabeling samples in each training subset which are consistently wrongly predicted by comparing the predictions with a consistency threshold.

5. The method as claimed in claim 4, wherein the consistency threshold is estimated from the distribution of counts.

6. The method as claimed in claim 5, wherein the consistency threshold is determined using an optimization method to identify a threshold count that minimizes the cumulative distribution of counts.

7. The method as claimed in claim 6, wherein determining a consistency threshold comprises:

generating a histogram of the counts where each bin of the histogram comprises the number of samples in the training dataset with the same count where the number of bins is the number of training subsets multiplied by number of AI models;

generating a cumulative histogram from the histogram;

calculating a weighted difference between each pair of adjacent bins in the cumulative histogram;

setting the consistency threshold as the bin that minimizes the weighted differences.

8. The method as claimed in claim 1, further comprising:

after generating the cleansed aggregated training dataset and prior to generating a final AI model:

iteratively retraining the plurality of trained AI models using the cleansed aggregated dataset; and generating an updated cleansed aggregated training set until a pre-determined level of performance is achieved or until there are no further samples with a count below the consistency threshold.

9. The method as claimed in claim 1, wherein after cleaning the aggregated dataset, the method further comprises:

for each training dataset where the positive predictive power is outside the predefined range, adding the respective dataset to the aggregated dataset and cleaning the updated aggregated dataset to generate a cleansed updated aggregated training dataset comprising:

dividing the updated aggregated dataset into a plurality (k) of training subsets;

training, for each training subset, a plurality (n) of Artificial Intelligence (AI) models on two or more of the remaining (k−1) training subsets and using the plurality of trained AI models to obtain an estimated label for each sample in the training subset for each trained AI model;

removing or relabeling samples in each training subset which are consistently incorrectly predicted by the plurality of trained AI models; and generating the final AI model by training one or more AI models using the cleansed aggregated training dataset comprises generating a final AI model by training one or more AI models using the cleansed updated aggregated training dataset.

10. The method as claimed in claim 1 further comprising:
identifying one or more noisy classes and one or more correct classes;
and after the step of training the plurality (n) of Artificial Intelligence (AI) models, the method further comprises selecting a set of models where a model is selected if a metric for each correct class exceeds a first threshold, and a metric in each noisy classes is less than a second threshold;
and the step of obtaining a count of the number of times each sample in the training dataset is either correctly predicted or passes a threshold confidence level is performed for each of the selected models;
and the step of removing or relabeling samples in each training set with a count below a consistency threshold comprises is performed separately for each noisy class and each correct class, and the consistency threshold is a per-class consistency threshold.

11. The method claimed in claim 1, further comprising assessing the label noise in each training dataset prior to testing the training dataset for positive predictive power comprising:
splitting the training dataset into a training set, a validation set and a test set;
randomizing the class labels in the training set;
training an AI model on the training set with randomized class labels, and testing the AI model using the validation set and test sets;
estimating a first metric for the validation set and a second metric for the test set;
excluding the training dataset if the first metric and the second metric are not within a predefined range.

12. The method claimed in claim 1, further comprising assessing the transferability of each training dataset in the plurality of training datasets comprising:
splitting the training dataset into a training set, a validation set and a test set;
training an AI model on the training set, and testing the AI model using the validation set and test sets;
for each epoch in a plurality of epochs, estimating a first metric of the validation set and a second metric of the test set; and
estimating the correlation of the first metric and the second metric over the plurality of epochs.

13. A computational method for labeling a dataset for generating an Artificial Intelligence (AI) model, the method comprising:
dividing a labeled training dataset into a plurality (k) of training subsets wherein there are C labels;
training, for each training subset, a plurality (n) of Artificial Intelligence (AI) models on two or more of the remaining (k−1) training subsets;
obtaining a plurality of label estimates for each sample in an unlabeled dataset using the plurality of trained AI models;
repeating the dividing, training and obtaining steps C times; and
assigning a label for each sample in the unlabeled dataset by using a voting strategy to combine the plurality of estimated labels for the sample; and
cleaning the labeled training dataset to generate a cleansed labeled training dataset comprising:
dividing the labeled training dataset into a plurality (k) of training subsets;
training, for each training subset, a plurality (n) of Artificial Intelligence (AI) models on two or more of the remaining (k−1) training subsets and using the plurality of trained AI models to obtain an estimated label for each sample in the training subset for each trained AI model; and
removing or relabeling samples in each training subset which are consistently incorrectly predicted by the plurality of trained AI models.

14. The method as claimed in claim 13, wherein the plurality of Artificial Intelligence (AI) models comprises a plurality of model architectures.

15. The method as claimed in claim 13, wherein training, for each training subset, a plurality of Artificial Intelligence (AI) models on two or more of the remaining (k−1) training subsets comprises:
training, for each training subset, a plurality of Artificial Intelligence (AI) models on all of the remaining (k−1) training subsets.

16. The method as claimed in claim 13 wherein dividing, training, obtaining and repeating the dividing and training steps C times comprises:
generating C temporary datasets from the unlabeled dataset, wherein each sample in the temporary dataset is assigned a temporary label from the C labels, such that each of the plurality of temporary datasets are distinct datasets, and
repeating the dividing, training and obtaining steps C times comprises performing the dividing, training and obtaining steps for each of the temporary datasets, such that for each temporary datasets the dividing step comprises combining the temporary dataset with the labeled training dataset and then dividing into a plurality (k) of training subsets, and
the training and obtaining step comprises training, for each training subset, a plurality (n) of Artificial Intelligence (AI) models on two or more of the remaining (k−1) training subsets and using the plurality of trained AI models to obtain an estimated label for each sample in the training subset for each trained AI model.

17. The method as claimed in claim 16 wherein assigning a temporary label from the C labels is assigned randomly.

18. The method as claimed in claim 16 wherein assigning a temporary label from the C labels is estimated by an AI model trained on the training data.

19. The method as claimed in claim 16 wherein assigning a temporary label from the C labels is assigned from the set of C labels in random order such that each label occurs once in the set of C temporary datasets.

20. The method as claimed in claim 16 wherein the steps of combining the temporary dataset with the labeled training dataset further comprises splitting the temporary dataset into a plurality of subsets, and combining each subset with the labeled training dataset and dividing into a plurality (k) of training subsets and performing the training step.

21. The method as claimed in claim 20 wherein the size of each subset is less than the 20% of the size of the training set.

22. The method as claimed in claim 13 wherein Cis 1 and the voting strategy is a majority inferred strategy.

23. The method as claimed in claim 13 wherein Cis 1 and the voting strategy is a maximum confidence strategy.

24. The method as claimed in claim 13, wherein C is greater than 1, and the voting strategy is a consensus based strategy based on the number of times each label is estimated by plurality of models.

25. The method as claimed in claim 24 wherein C is greater than 1 and the voting strategy counts the number of times each label is estimated for a sample, and assigns the label with the highest count that is more than a threshold amount of the second highest count.

26. The method as claimed in claim 13 wherein C is greater than 1 and the voting strategy is configured to estimate the label which is reliably estimated by a plurality of models.

27. The method as claimed in claim 13, wherein the dataset is a healthcare dataset.

28. The method as claimed in claim 27 wherein the healthcare dataset comprises a plurality of healthcare images.

29. A computational system comprising one or more processors, one or more memories, and a communications interface, wherein the one or more memories store instructions for configuring the one or more processors to generate a final trained AI model by:

testing each training dataset in a plurality of training datasets for positive predictive power and generating a cleansed training dataset if the positive predictive power is within a predefined range, wherein estimating the positive predictive power comprises:

dividing a training dataset into a plurality of validation subsets;

training, for each validation subset, a plurality of Artificial Intelligence (AI) models on two or more of the remaining (k−1) validation subsets;

obtaining a first count of the number of times each sample in the validation dataset is either correctly predicted, incorrectly predicted, or passes a threshold confidence level, by the plurality of trained AI models;

randomly assigning a label or outcome to each sample;

training, for each validation subset, a plurality of Artificial Intelligence (AI) models on two or more of the remaining (k−1) validation subsets;

obtaining a second count of the number of times each sample in the validation dataset is either correctly predicted, incorrectly predicted, or passes a threshold confidence level, by the plurality of trained AI models when random assigned labels are used;

estimating the positive predictive power by comparing the first count and the second count; and generating the cleansed training dataset if the positive predictive power is within a predefined range wherein generating a cleansed training data set comprises:

dividing a training dataset into a plurality (k) of training subsets;

training, for each training subset, a plurality (n) of Artificial Intelligence (AI) models on two or more of the remaining (k−1) training subsets and using the plurality of trained AI models to obtain an estimated label for each sample in the training subset for each trained AI model; and removing or relabeling samples in each training subset which are consistently incorrectly predicted by the plurality of trained AI models;

generating an aggregated dataset using the plurality of cleansed datasets;

cleaning the aggregated dataset to generate a cleansed aggregated training dataset comprising:

dividing the aggregated dataset into a plurality (k) of training subsets;

training, for each training subset, a plurality (n) of Artificial Intelligence (AI) models on two or more of the remaining (k−1) training subsets and using the plurality of trained AI models to obtain an estimated label for each sample in the training subset for each trained AI model;

removing or relabeling samples in each training subset which are consistently incorrectly predicted by the plurality of trained AI models; and generating a final trained AI model by training one or more AI models using the cleansed aggregated training dataset.

30. A computational system comprising one or more processors, one or more memories, and a communications interface, wherein the one or more memories are configured to:

store a final trained AI model, wherein the final AI model is generated by a computational system configured to:

test each training dataset in a plurality of training datasets for positive predictive power and generating a cleansed training dataset if the positive predictive power is within a predefined range, wherein estimating the positive predictive power comprises:

dividing a training dataset into a plurality of validation subsets;

training, for each validation subset, a plurality of Artificial Intelligence (AI) models on two or more of the remaining (k−1) validation subsets;

obtaining a first count of the number of times each sample in the validation dataset is either correctly predicted, incorrectly predicted, or passes a threshold confidence level, by the plurality of trained AI models;

randomly assigning a label or outcome to each sample;

training, for each validation subset, a plurality of Artificial Intelligence (AI) models on two or more of the remaining (k−1) validation subsets;

obtaining a second count of the number of times each sample in the validation dataset is either correctly predicted, incorrectly predicted, or passes a threshold confidence level, by the plurality of trained AI models when random assigned labels are used;

estimating the positive predictive power by comparing the first count and the second count; and generating the cleansed training dataset if the positive predictive power is within a predefined range wherein generate a cleansed training data set comprises:

dividing a training dataset into a plurality (k) of training subsets;

training, for each training subset, a plurality (n) of Artificial Intelligence (AI) models on two or more of the remaining (k−1) training subsets and using the plurality of trained AI models to obtain an estimated label for each sample in the training subset for each trained AI model; and removing or relabeling samples in each training subset which are consistently incorrectly predicted by the plurality of trained AI models;

generate an aggregated dataset using the plurality of cleansed datasets; and cleaning the aggregated dataset to generate a cleansed aggregated training dataset comprising:

dividing the aggregated dataset into a plurality (k) of training subsets;

training, for each training subset, a plurality (n) of Artificial Intelligence (AI) models on two or more of the remaining (k−1) training subsets and using the plurality of trained AI models to obtain an estimated label for each sample in the training subset for each trained AI model; and removing or relabeling samples in each training subset which are consistently incorrectly predicted by the plurality of trained AI models; and generate a final trained AI model by training one or more AI models using the cleansed aggregated training dataset, wherein the one or more processors are configured to receive input data via the communications interface, process the input data using the stored final trained AI model to generate a model result, and the communications interface is configured to send the model result to a user interface or data storage device.

31. A computational system comprising one or more processors, one or more memories, and a communications interface, wherein the one or more memories store instructions for configuring the one or more processors to label a dataset for generating an Artificial Intelligence (AI) model comprising:

dividing a labeled training dataset into a plurality (k) of training subsets wherein there are C labels;

training, for each training subset, a plurality (n) of Artificial Intelligence (AI) models on two or more of the remaining (k−1) training subsets;

obtaining a plurality of label estimates for each sample in an unlabeled dataset using the plurality of trained AI models;

repeating the dividing, training and obtaining steps C times; and assigning a label for each sample in the unlabeled dataset by using a voting strategy to combine the plurality of estimated labels for the sample, wherein the one or more memories store instructions for configuring the one or more processors to clean the labeled training dataset to generate a cleansed labeled training dataset comprising:

dividing the labeled training dataset into a plurality (k) of training subsets;

training, for each training subset, a plurality (n) of Artificial Intelligence (AI) models on two or more of the remaining (k−1) training subsets and using the plurality of trained AI models to obtain an estimated label for each sample in the training subset for each trained AI model;

removing or relabeling samples in each training subset which are consistently incorrectly predicted by the plurality of trained AI models.

* * * * *